United States Patent [19]

Chakravarty et al.

[11] Patent Number: 5,412,097
[45] Date of Patent: May 2, 1995

[54] HETEROCYCLIC COMPOUNDS BEARING ACIDIC FUNCTIONAL GROUPS AS ANGIOTENSIN II ANTAGONISTS

[75] Inventors: Prasun K. Chakravarty, Edison; William J. Greenlee, Teaneck; Dooseop Kim, Scotch Plains; Nathan B. Mantlo; Arthur A. Patchett, both of Westfield; Ralph A. Rivero, Tinton Falls, all of N.J.

[73] Assignee: Merck & Co., Inc., Rahway, N.J.

[21] Appl. No.: 940,267

[22] Filed: Sep. 2, 1992

Related U.S. Application Data

[63] Continuation-in-part of Ser. No. 832,781, Feb. 14, 1992, abandoned, which is a continuation-in-part of Ser. No. 666,534, Mar. 8, 1991, abandoned.

[51] Int. Cl.$^6$ .................. C07D 471/04; C07D 473/00; A61K 31/52; A61K 31/435
[52] U.S. Cl. .................................... 546/118; 546/120; 546/23
[58] Field of Search ................................ 546/118, 120

[56] References Cited

FOREIGN PATENT DOCUMENTS 400974 12/1990 European Pat. Off. ............ 546/118
0533058A1 9/1991 European Pat. Off. ............ 546/118

*Primary Examiner*—Robert T. Bond
*Attorney, Agent, or Firm*—Valerie J. Camara; Mark R. Daniel; Joseph F. DiPrima

[57] ABSTRACT

Heterocyclic compounds of structural formula:

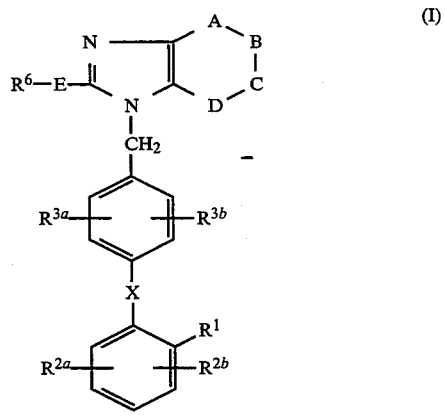

wherein A, B, C, and D are independently carbon atoms or nitrogen atoms are angiotensin II antagonists useful in the treatment of hypertension and congestive heart failure.

15 Claims, No Drawings

HETEROCYCLIC COMPOUNDS BEARING ACIDIC FUNCTIONAL GROUPS AS ANGIOTENSIN II ANTAGONISTS

The present application is a continuation-in-part of Ser. No. 07/832,781 filed on Feb. 14, 1992, now abandoned, which is a continuation-in-part of Ser. No. 07/666,534 filed on Mar. 8, 1991, now abandoned.

SUMMARY OF THE INVENTION

This invention relates to novel compounds of structural formula I which are angiotensin II antagonists useful in the treatment of hypertension, congestive heart failure, and elevated intraocular pressure.

It also relates to processes for preparing the novel compounds; pharmaceutical formulations comprising one or more of the compounds as active ingredient; and, a method of treatment of hypertension, congestive heart failure, and elevated intraocular pressure.

BACKGROUND OF THE INVENTION

Renin-angiotensin system (RAS) plays a central role in the regulation of normal blood pressure and seems to be critically involved in hypertension development and maintenance as well as congestive heart failure. Angiotensin II (AII), an octapeptide hormone is produced mainly in the blood during the cleavage of angiotensin I by angiotensin converting enzyme (ACE) localized on the endothelium of blood vessels of lung, kidney, and many other organs, and is the end product of the RAS. AII is a powerful arterial vasoconstricter that exerts its action by interacting with specific receptors present on cell membranes. One of the possible modes of controlling the RAS is angiotensin II receptor antagonism. Several peptide analogs of A II are known to inhibit the effect of this hormone by competitively blocking the receptors, but their experimental and clinical applications have been limited by the partial agonist activity and lack of oral absorption [M. Antonaccio. *Clin. Exp. Hypertens.* A4, 27–46 (1982); D. H. P. Streeten and G. H. Anderson, Jr.—*Handbook of Hypertension, Clinical Pharmacology of Antihypertensive Drugs*, ed. A. E. Doyle, Vol. 5, pp. 246–271, Elsevier Science Publisher, Amsterdam, The Netherlands, 1984].

Recently, several non-peptide compounds have been described as A II antagonists. Illustrative of such compounds are those disclosed in U.S. Pat. Nos. 4,207,324; 4,340,598; 4,576,958; 4,582,847; and 4,880,804; in European Patent Applications 028,834 245,637; 253,310; and 291,969; and in articles by A. T. Chiu, et al. [*Eur. J. Pharm. Exp. Therap*, 157, 13–21 (1988)] and by P. C. Wong, et al. [*J. Pharm. Exp. Therap*, 247, 1–7(1988)]. All of the U.S. Patents, European Patent Applications 028,834, 253,310,324,377, 403,158 and 403,159 and the two articles disclose substituted imidazole compounds which are generally bonded through a lower alkyl bridge to a substituted phenyl. European Patent Application 245,637 discloses derivatives of 4,5,6,7-tetrahydro-2H-imidazo[4,5-c]pyridine-6-carboxylic acid and analogs thereof as antihypertensive agents. U.S. Pat. No. 4,880,804 and European Patent Applications 392,317, 399,732 and 400,835 disclose derivatives of benzimidazole attached via a bridge to a biphenyl moiety as antihypertensive agents. European Patent Applications 399,732 and 400,974 disclose derivatives of imidazopyridines attached via a bridge to a biphenyl moiety as antihypertensive agents.

DETAILED DESCRIPTION OF THE INVENTION

This invention relates to substituted imidazo-fused 6-membered ring heterocycles of the formula I shown below which are angiotensin II antagonists and are useful in the treatment of hypertension, congestive heart failure, and elevated intraocular pressure.

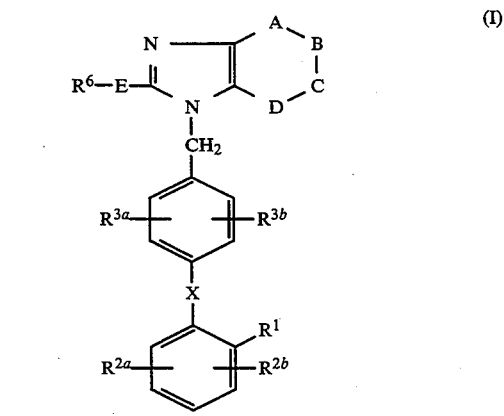

wherein:

$R^1$ is (a) $-SO_2N(R^{24})-OR^{24}$, (b) $-SO_2NHSO_2R^{23}$, (c) $-SO_2NH-\overset{\overset{O}{\|}}{P}(R^{25})_2$, (d) $-CONH-\overset{\overset{O}{\|}}{P}(R^{25})_2$, (e) $-SO_2NHCN$, (f) $-SO_2NHCO_2R^{23}$, (g) $-SO_2NHSO_2-N\overset{\frown}{\underset{\smile}{\phantom{N}}}Z$, (h) $-NHSO_2NHSO_2R^{23}$, (i) $-NHSO_2NH\overset{\overset{O}{\|}}{P}(R^{25})_2$, (j) 
$$-N\underset{\underset{O}{\overset{\|}{S}}\overset{\|}{\underset{O}{}}}{\overset{R^{26}\;\;R^{26}}{\diagup\!\!\diagdown}}\overset{O}{\underset{NH}{\diagdown\!\!\diagup}}$$, (k)
$$-N\underset{\underset{O}{\diagdown\!\!\diagup}}{\overset{R^{26}\;\;R^{26}}{\diagup\!\!\diagdown}}\underset{NH}{\overset{\overset{O}{\diagup\!\!\!\!S}}{\diagdown\!\!\!\!\diagup}}O,$$

-continued

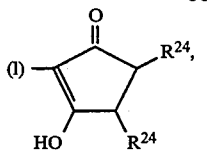
(l)

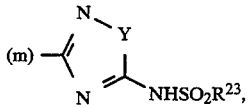
(m)

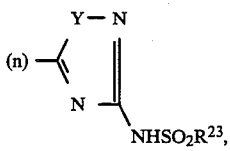
(n)

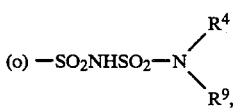
(o) —SO₂NHSO₂—N⟨R⁴/R⁹,

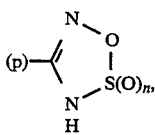
(p)

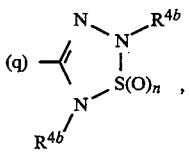
(q)

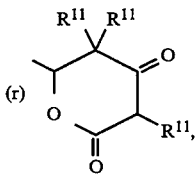
(r)

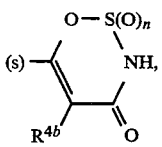
(s)

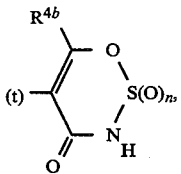
(t)

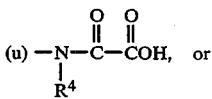
(u) or (v) —NHSO₂R²³;

wherein
Y is O or S;
R²ᵃ and R²ᵇ are independently H, Cl, Br, I, F, —NO₂, —NH₂, C₁–C₄-alkylamino, di(C₁–C₄ alkyl)amino, —SO₂NHR⁹, CF₃, C₁–C₆-alkyl, or C₁–C₆-alkoxy,
C₁–C₆-polyfluoroalkoxy, CH₂—C₁–C₆-alkoxy, CH₂—S—C₁–C₆-alkyl, CH₂NR⁹R⁹, (CH₂)-aryl, aryl, C₁–C₆-polyfluoroalkyl, O(CH₂)t-aryl, (CH₂)ᵣ-aryl, O(CH₂)ᵣ—C₁–C₆-alkoxy, O-aryl, —NR⁴R⁴ᵇ, C₁–C₆-thioalkoxy, S(O)ₛ—(CH₂)ᵣ-aryl, CH₂N(CH₂CH₂)₂O; C₁–C₆-alkyl, optionally substituted with: C₁–C₃-alkyl, s is: 0–2;
t is: 1–3;
R³ᵃ i
(a) H,
(b) Cl, Br, I, or F,
(c) C₁–C₆-alkyl,
(d) C₁–C₆-alkoxy, or
(e) C₁–C₆-alkoxyalkyl;

R³ᵇ is
(a) H,
(b) Cl, Br, I, or F,
(c) NO₂,
(d) C₁–C₆-alkyl,
(e) C₁–C₆-acyloxy,
(f) C₁–C₆-cycloalkyl
(g) C₁–C₆-alkoxy,
(h) —NHSO₂R⁴,
(i) hydroxy C₁–C₄-alkyl,
(j) aryl C₁–C₄-alkyl,
(k) C₁–C₄-alkylthio,
(l) C₁–C₄-alkyl sulfinyl,
(m) C₁–C₄-alkyl sulfonyl,
(n) NH₂,
(o) C₁–C₄-alkylamino,
(p) C₁–C₄-dialkylamino,
(q) fluoro C₁–C₄-alkyl,
(r) —SO₂—NHR⁹,
(s) aryl, or
(t) furyl;

wherein aryl is phenyl or naphthyl or substituted phenyl or naphthyl with one or two substituents selected from the group consisting of Cl, Br, I, F, C₁–C₄-alkyl, C₁–C₄-alkoxy, NO₂, CF₃, C₁–C₄-alkylthio, OH, NH₂, NH(C₁–C₄-alkyl), N(C₁–C₄-alkyl)₂, CO₂H, and CO₂—C₁–C₄-alkyl;

R⁴ is:
(a) H,
(b) aryl, wherein aryl is as defined above, or
(c) C₁–C₆-alkyl, substituted or unsubstituted with aryl, furyl, thienyl, pyridyl, C₃–C₆-cycloalkyl, and F;

R⁴ᵃ is
(a) aryl, wherein aryl is as defined above, or
(b) C₁–C₆-alkyl, substituted or unsubstituted with aryl, furyl, thienyl, pyridyl, C₃–C₆-cycloalkyl, and F;

R⁴ᵇ is H, C₁–C₆ alkyl, aryl, —CH₂-aryl, —CO—C₁–C₆-alkyl, —CO—C₃–C₆-cycloalkyl, —CO-aryl, —CO₂—C₁–C₆-alkyl, —CO₂—C₃–C₆-cycloalkyl, —CO₂-aryl, —CONR⁴—C₁–C₆-alkyl, —SO₂-aryl, —SO₂—C₁–C₆-alkyl, —CO—heteroaryl, —SO₂NR⁴—C₁–C₆-alkyl, or —SO₂NR⁴-aryl;

R⁵ is

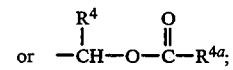
or

E is a single bond, —NR$^{13}$(CH$_2$)$_s$—, —S(O)$_n$—, (CH$_2$)$_s$— where n is 0 to 2 and s is 0 to 5, —CH(OH)—, —O—, or —CO—;

R$^6$ is
(a) aryl or substituted aryl with 1 or 2 substituents selected from the group consisting of Cl, Br, I, F —O—C$_1$–C$_4$-alkyl, C$_1$–C$_4$-alkyl, —NO$_2$, —CF$_3$, —SO$_2$NR$^9$R$^{10}$, —S—C$_1$–C$_4$-alkyl, —OH, —NH$_2$, C$_3$–C$_7$-cycloalkyl, C$_3$–C$_{10}$-alkenyl;
(b) C$_1$–C$_9$-alkyl, C$_2$–C$_6$-alkenyl or C$_2$–C$_6$-alkynyl, or substituted C$_1$–C$_9$ alkyl, C$_2$–C$_6$ alkenyl or C$_2$–C$_6$ alkynyl with a substituent selected from the group consisting of aryl as defined above, C$_3$–C$_7$-cycloalkyl, Cl, Br, I, F, —OH, —NH$_2$, —NH(C$_1$–C$_4$-alkyl), —CF$_2$CF$_3$, —N(C$_1$–C$_4$-alkyl)$_2$, —NH—SO$_2$R$^4$, COOR$^4$, —CF$_3$, —CF$_2$CH$_3$, —SO$_2$NHR$^9$; or
(c) an unsubstituted, monosubstituted or disubstituted aromatic 5 or 6 membered cyclic ring which contains one or two members selected from the group consisting of N, O, S, and wherein the substituents are members selected from the group consisting of —OH, —SH, C$_1$–C$_4$-alkyl, C$_1$–C$_4$-alkyloxy, —CF$_3$, Cl, Br, I, F, or NO$_2$, or
(d) perfluoro-C$_1$–C$_4$-alkyl, or
(e) C$_3$–C$_7$-cycloalkyl or mono- or disubstituted C$_3$–C$_7$ cycloalkyl with a C$_1$–C$_4$-alkyl or —CF$_3$ substituent;

R$^9$ is H, C$_1$–C$_5$-alkyl, aryl or —CH$_2$-aryl;
R$^{10}$ is H, C$_1$–C$_4$-alkyl;
R$^{11}$ is H, C$_1$–C$_6$-alkyl, C$_2$–C$_4$-alkenyl, C$_1$–C$_4$-alkoxy-C$_1$–C$_4$-alkyl, or

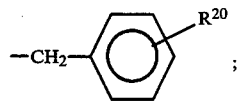

R$^{13}$ is H, —CO(C$_1$–C$_4$-alkyl), C$_1$–C$_6$-alkyl, allyl, C$_3$–C$_6$-cycloalkyl, phenyl or benzyl;
R$^{14}$ is H, C$_1$–C$_8$-alkyl, C$_1$–C$_8$-perfluoroalkyl, C$_3$–C$_6$-cycloalkyl, phenyl or benzyl;
R$^{15}$ is H, C$_1$–C$_6$-alkyl;
R$^{16}$ is H, C$_1$–C$_6$-alkyl, C$_3$–C$_6$-cycloalkyl, phenyl or benzyl;
R$^{17}$ is —NR$^9$R$^{10}$, —OR$^{10}$, —NHCONH$_2$, —NHCSNH$_2$,

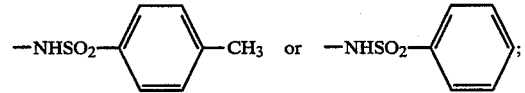

R$^{18}$ and R$^{19}$ are independently C$_1$–C$_4$-alkyl or taken together are —(CH$_2$)$_q$— where q is 2 or 3;
R$^{20}$ is H, —NO$_2$, —NH$_2$, —OH or —OCH$_3$;
R$^{23}$ is
(a) aryl,
(b) heteroaryl, wherein heteroaryl is an unsubstituted, monosubstituted or disubstituted five- or six-membered aromatic ring which contains 1 to 3 heteroatoms selected from the group consisting of O, N or S and wherein the substituents are members selected from the group consisting of —OH, —SH, —C$_1$–C$_4$-alkyl, —C$_1$–C$_4$-alkoxy, Cl, Br, F, I, —NO$_2$, —CO$_2$H, —CO$_2$—C$_1$–C$_4$-alkyl, —NH$_2$, —NH(C$_1$–C$_4$-alkyl) and —N(C$_1$–C$_4$-alkyl)$_2$;
(c) C$_3$–C$_7$-cycloalkyl,
(d) C$_1$–C$_6$-alkyl or substituted C$_1$–C$_6$ alkyl with a substituent that is a member selected from the group consisting of aryl, heteroaryl, —OH, —SH, —C$_1$–C$_4$-alkyl, —C$_3$–C$_7$-cycloalkyl, —O(C$_1$–C$_6$-alkyl), —S(O)$_n$(C$_1$–C$_6$-alkyl), —CF$_3$, Cl, Br, F, I, —NO$_2$, —CO$_2$H, —CO$_2$—C$_1$–C$_4$-alkyl, —NH$_2$, —NH(C$_1$–C$_4$-alkyl), —NHCOR$^{4a}$, —N(C$_1$–C$_4$-alkyl)$_2$, —PO(OH)(C$_1$–C$_4$-alkyl), —PO(OH)(aryl), or —PO(OH)(O—C$_1$–C$_4$-alkyl); where n is 0 to 2, or
(e) polyfluoro-C$_1$–C$_6$-alkyl, except when R$^1$ is —NHSO$_2$R$^{23}$;

R$^{24}$ is
(a) H,
(b) aryl as defined above, or
(c) C$_1$–C$_6$-alkyl optionally substituted with aryl, F, Cl, Br, —OH, —NH$_2$, —NH(C$_1$–C$_4$-alkyl), —N(C$_1$–C$_4$-alkyl)$_2$, CF$_3$, O—C$_1$–C$_4$-alkyl, or O(CH$_2$)$_{n+1}$—O—C$_1$–C$_4$-alkyl, or
(d) C$_3$–C$_7$-cycloalkyl;

R$^{25}$ is
(a) aryl and substituted aryl as defined above,
(b) C$_1$–C$_6$-alkyl optionally substituted with aryl, F, Cl, Br, —OH, —NH$_2$, —NH(C$_1$–C$_4$-alkyl), —N(C$_1$–C$_4$-alkyl)$_2$, CF$_3$, —COOR$^4$, or CN,
(c) —CH(R$^4$)—O—CO—R$^{4a}$, or
(d) —OH, —O—C$_1$–C$_6$-alkyl wherein alkyl is as defined in (b);

R$^{26}$ is
(a) H,
(b) C$_1$–C$_6$-alkyl optionally substituted with aryl, F, Cl, Br, —OH, —NH$_2$, —NH(C$_1$–C$_4$-alkyl), —N(C$_1$–C$_4$-alkyl)$_2$, CF$_3$, —COOR$^4$, or CN,
(c) F, Cl, Br, or
(d) —O—C$_1$–C$_4$-alkyl wherein alkyl is defined as in (b);

X is
(a) a carbon-carbon single bond,
(b) —CO—,
(c) —O—,
(d) —S—,
(e)

(f)

(g)

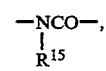

(h) —OCH$_2$—,
(i) —CH$_2$O—
(j) —SCH$_2$—,
(k) —CH$_2$S—,
(l) —NHC(R$^9$)(R$^{10}$),
(m) —NR$^9$SO$_2$—, (n) —SO$_2$NR$^9$—,
(o) —C(R$^9$)(R$^{10}$)NH—,
(p) —CH=CH—,
(q) —CF=CF—,
(r) —CH=CF—,
(s) —CF=CH—,
(t) —CH$_2$CH$_2$—,
(u) —CF$_2$CF$_2$—,
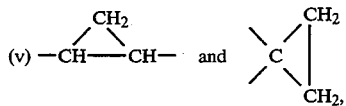
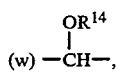
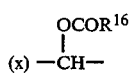
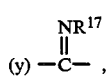
or
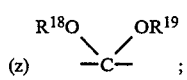
Z is CH$_2$, O, NR$^{13}$ or S;
—A—B—C—D— represents the constituent atoms of a 6-member saturated or unsaturated heterocyclic ring with the imidazole to which they are attached containing 1 to 3 nitrogen atoms and includes the following:
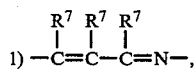
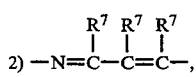
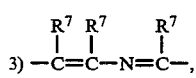
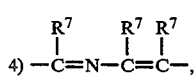
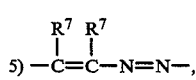
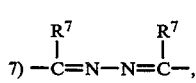
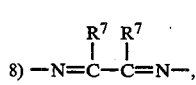
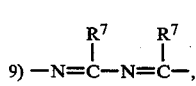
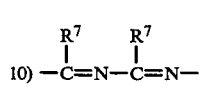
-continued
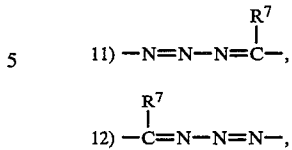
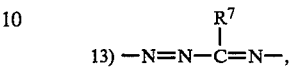
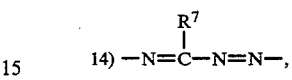
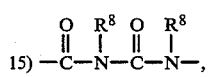
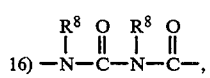
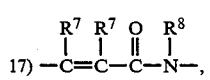
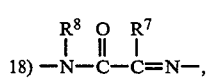
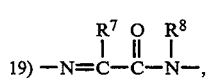
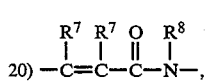
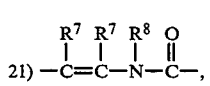
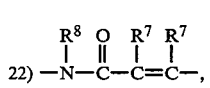
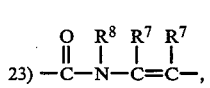
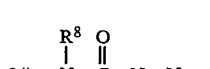
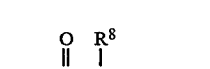
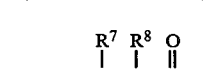
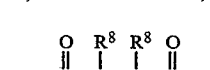
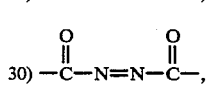

-continued

31) 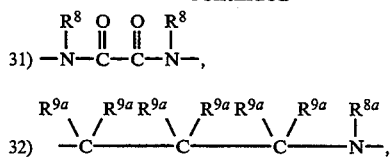

32) 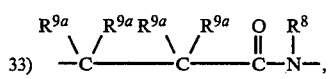

33) 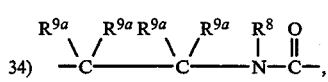

34) 

35) 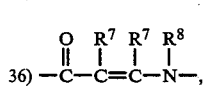

36) 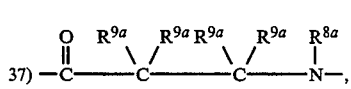

37) 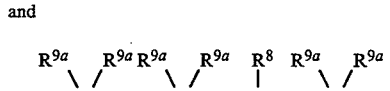

and

38) 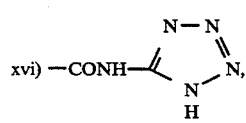

$R^7$ groups can be the same or different and represent:
a) hydrogen,
b) $C_1$–$C_6$ alkyl, or $C_2$–$C_6$ alkenyl, or $C_2$–$C_6$ alkynyl each of which is unsubstituted or substituted with:
 i) —OH
 ii) $C_1$–$C_4$-alkoxy,
 iii) —$CO_2R^4$ or —$CO_2R^5$,
 iv) —$OCOR^4$,
 v) 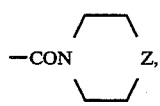
 vi) —$CON(R^4)_2$, $R^4$ O
 vii) —N—$CR^{23}$,
 viii) —$N(R^4)R^{23}$,
 ix) aryl,
 x) heteroaryl as defined in (o) below,
 xi) —$S(O)_nR^{23}$,
 xii) tetrazol-5-yl,
 xiii) —$CONHSO_2R^{23}$,
 xiv) —$SO_2NHR^{23}$,
 xv) —$SO_2NHCOR^{23}$,
 xvi) —CONH—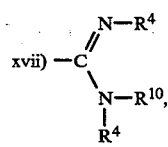
 xvii) 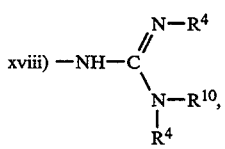

xviii) 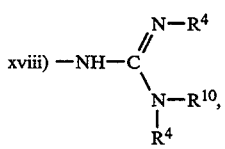

xix) —$PO(OR^4)_2$, or
 xx) —$PO(OR^4)R^9$,
c) fluoro, chloro, bromo or iodo,
d) perfluoro-$C_1$–$C_4$-alkyl,
e) —OH,
f) —$NH_2$,
g) 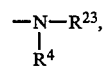

h) 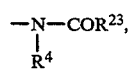

i) —$OR^{23}$,
j) —$CO_2R^4$ or —$CO_2R^{23}$,
k) —$CON(R^4)R^{23}$,
l) —NH—$C_3$–$C_7$-cycloalkyl,
m) $C_3$–$C_7$-cycloalkyl,
n) aryl,
o) heteroaryl which is a five- or six-membered saturated or unsaturated ring containing up to three heteroatoms selected from the group consisting of O, N or S wherein S may in the form of sulfoxide or sulfone and which may be substituted with one or two substituents which are members selected from the group consisting of Cl, Br, F, I, $C_1$–$C_4$-alkyl, $C_1$–$C_4$-alkoxy, $C_1$–$C_4$—$S(O)_n$—, $CF_3$, $NO_2$, OH, $CO_2H$, $CO_2$—$C_1$–$C_4$-alkyl, $NH_2$, $NH(C_1$–$C_4$-alkyl), or —$N(R^4)_2$;
p) —CN,
q) 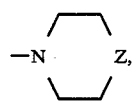

r) —$SO_2N(R^4)_2$,
s) tetrazol-5-yl,
t) —$CONHSO_2R^{23}$,
u) —$PO(OR^4)_2$,
v) —$SO_2NHR^{23}$,
w) —$SO_2NHCOR^{23}$,
x) —$S(O)_n$—$R^{23}$,
y) 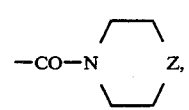

z) —$PO(OR^4)R^9$ or —$PO(OR^5)R^9$,
aa) —$SO_2NHCON(R^{23})_2$,
bb) —$NHSO_2NHR^{23}$, cc) —NHSO$_2$NHCOR$^{23}$,
dd) —NHCONHSO$_2$R$^{23}$,
ee) —N(R$^4$)CO$_2$R$^{23}$, R$^4$ R$^4$
ff) —N—CON—R$^{23}$,
gg) —CO-aryl,
hh)

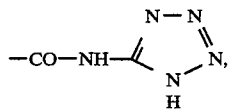

ii) —CO—C$_1$-C$_4$-alkyl,
jj) —SO$_2$NH—CN,
kk) —NHSO$_2$R$^{23}$,
ll)

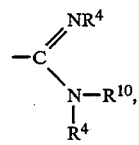

mm)

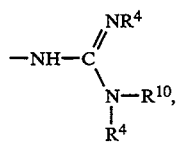

nn)

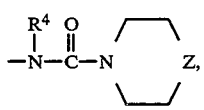

or
oo)

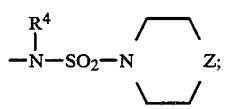

R$^8$ groups can be the same or different and represent:
  a) hydrogen,
  b) C$_1$-C$_6$-alkyl or C$_2$-C$_6$ alkenyl either unsubstituted or substituted with hydroxy, C$_1$-C$_4$-alkoxy, —N(R$^4$)$_2$, —CO$_2$R$^4$, or C$_3$-C$_5$-cycloalkyl, or
  c) C$_3$-C$_5$-cycloalkyl;
R$^{8a}$ is R$^8$ or C$_1$-C$_4$-acyl;
R$^{9a}$ groups can be the same or different and represent:
  a) hydrogen, or
  b) C$_1$-C$_6$-alkyl either unsubstituted or substituted with
    i) hydroxy,
    ii) —CO$_2$R$^4$,
    iii) —CONHR$^4$, or
    iv) —CON(R$^4$)$_2$; and,
the pharmaceutically acceptable salts thereof.

The terms "alkyl," "alkenyl," "alkynyl," and the like include both the straight chain and branched chain species of these generic terms wherein the number of carbon atoms in the species permit. Unless otherwise noted, the specific names for these generic terms shall mean the straight chain species. For example, the term "butyl" shall mean the normal butyl substituent, n-butyl.

The heteroaryl substituent recited above represents any 5- or 6-membered aromatic ring containing from one to three heteroatoms selected from the group consisting of nitrogen, oxygen, and sulfur, for example, pyridyl, thienyl, furyl, pyrazolyl, pyrrolyl, imidazolyl, pyridazinyl, pyrimidinyl, pyrazinyl, isoxazolyl, isothiazolyl, oxazolyl, triazolyl and thiazolyl.

One embodiment of the novel compounds of this invention is the class compounds of Formula I wherein:
R$^1$ is:

(a) —SO$_2$N(R$^{24}$)—OR$^{24}$, (b) —SO$_2$NHSO$_2$R$^{23}$,

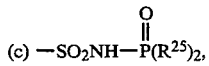

(d) —SO$_2$NHCN, (e) —SO$_2$NHCO$_2$R$^{23}$,

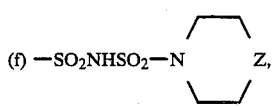

(g) —SO$_2$NHSO$_2$—N(R$^4$)(R$^9$), (h) —NHSO$_2$NHSO$_2$R$^{23}$, or

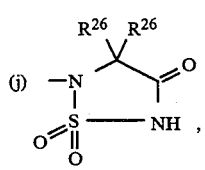

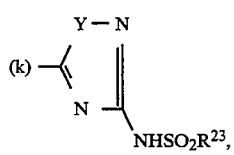

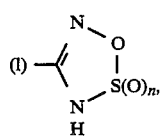

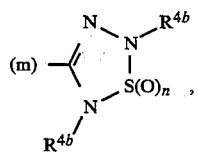

(n) 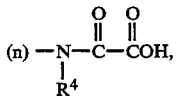

or (o) —NHSO$_2$R$^{23}$;

X is a single bond;
R$^{2a}$ and R$^{2b}$ are independently:
a) C$_1$–C$_6$-alkyl,
b) halogen,
c) hydrogen,
d) CH$_2$—C$_1$–C$_6$-alkoxy,
e) C$_1$–C$_6$-alkoxy,
f) —CH$_2$—S—C$_1$–C$_6$-alkyl,
g) CH$_2$NR$^9$R$^9$,
h) 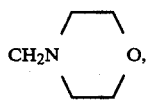

i) CH$_2$-aryl, or
j) aryl;
R$^{3a}$ and R$^{3b}$ are independently:
a) C$_1$–C$_6$-alkyl,
b) halogen,
c) C$_1$–C$_6$-alkoxy, or
d) hydrogen;
R$^4$ is H, or C$_1$–C$_4$-alkyl;
E is a single bond or —S—;
R$^6$ is C$_1$–C$_6$-alkyl, C$_3$–C$_7$-cycloalkyl, C$_2$–C$_6$-alkenyl or C$_2$–C$_6$-alkynyl each of which is either unsubstituted or substituted with C$_1$–C$_4$-alkylthio, C$_1$–C$_4$-alkoxy, CF$_3$, CF$_2$CF$_3$ or —CF$_2$CH$_3$; and
A—B—C—D— represents:

1) 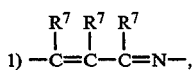

2) 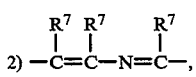

3) 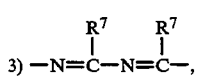

4) 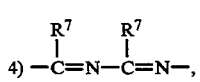

5) 

6) 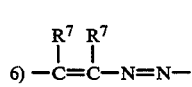

7) 

8) 

9) 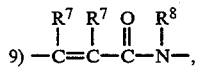

10) 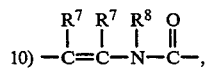

11) 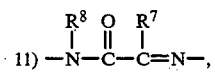

12) 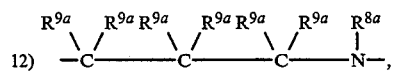

13) 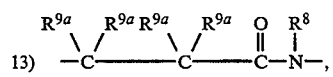

14) 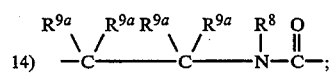

R$^7$ groups are the same or different and represent:
a) hydrogen,
b) C$_1$–C$_6$-alkyl, either unsubstituted or substituted with:
  i) —OH,
  ii) —CO$_2$R$^4$ or —CO$_2$R$^5$,
  iii) —NH$_2$,
  iv) (C$_1$–C$_4$ alkyl)amino,
  v) di(C$_1$–C$_4$-alkyl)amino,
c) —F, —Cl, —Br, or —I,
d) —CF$_3$,
e) —OH,
f) —N(R$^4$)R$^{23}$,
g) —C$_1$–C$_4$-alkoxy,
h) —CO$_2$R$^4$ or —CO$_2$R$^{23}$,
i) —CON(R$^4$)R$^{23}$,
j) —C$_3$–C$_7$-cycloalkyl,
k) aryl,
l) heteroaryl, R$^4$O
m) —N—C—R$^{23}$,
n) —N(R$^4$)CO$_2$R$^{23}$, R$^4$ R$^4$
o) —N—CON—R$^{23}$,
p) —NHSO$_2$R$^{23}$,
q) —NHSO$_2$NHR$^{23}$,
r) —CF$_3$,
s) tetrazol-5-yl,
t) —CONHSO$_2$R$^{23}$, u) 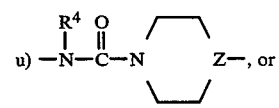 , or v) 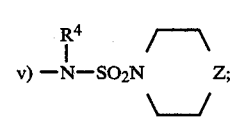 ;

R$^8$ groups are the same or different and represent,
a) hydrogen, or
b) C$_1$–C$_4$-alkyl either unsubstituted or substituted with —OH or —CO$_2$R$^4$;
R$^{8a}$ represents
a) hydrogen, or
b) C$_1$–C$_4$ alkyl, or
c) (C$_1$–C$_4$-alkyl)CO—; and $R^{9a}$ groups are the same or different and represent:
a) hydrogen, or
b) $C_1$-$C_4$-alkyl.

A class of this embodiment include those compounds of Formula I wherein:
$R^1$ is (a) —$SO_2N(R^{24})$—$OR^{24}$,
(b) —$SO_2NHSO_2R^{23}$, (c) —$SO_2NH$—$\overset{\overset{O}{\|}}{P}(R^{25})_2$, (d) —$SO_2NHCN$,
(e) —$SO_2NHCO_2R^{23}$, (f) —$SO_2NHSO_2$—N⟨ ⟩Z, (g) —$SO_2NHSO_2$—N⟨$R^4 \atop R^9$⟩, (h) —$NHSO_2NHSO_2R^{23}$, or (i) —$NHSO_2NH\overset{\overset{O}{\|}}{P}(R^{25})_2$;

(j) 
$$-\underset{\underset{\underset{O}{\|}}{S}}{\overset{R^{26}\ R^{26}}{N}}\diagdown\overset{O}{\diagup}\diagdown NH$$

(k) 
$$\overset{Y-N}{\underset{N}{\diagdown\diagup}}\diagdown NHSO_2R^{23}$$

(l) 
$$\overset{N-O}{\underset{N-S(O)_n}{\diagdown\diagup}}\\\phantom{xxx}H$$

(m) 
$$\overset{N\diagdown N\diagup R^{4b}}{\underset{N\diagup S(O)_n}{\phantom{x}}}\\\phantom{xx}R^{4b}$$

(n) —$\underset{R^4}{N}$—$\overset{\overset{O}{\|}}{C}$—$\overset{\overset{O}{\|}}{C}$—OH, or (o) —$NHSO_2R^{23}$;

E is a single bond;
A—B—C—D represents:

1) —$\overset{R^7}{\underset{|}{C}}$=$\overset{R^7}{\underset{|}{C}}$—$\overset{R^7}{\underset{|}{C}}$=N—, 2) —$\overset{R^7}{\underset{|}{C}}$=N—$\overset{R^7}{\underset{|}{C}}$=N— or 3) —$\overset{R^8}{\underset{|}{N}}$—$\overset{\overset{O}{\|}}{C}$—$\overset{R^8}{\underset{|}{N}}$—$\overset{\overset{O}{\|}}{C}$—.

A particular subclass of this embodiment includes the compounds of Formula (II);

(II)

[Structure: imidazopyridine with $R^{7a}$, $R^6$, $R^{7b}$ substituents; N—$CH_2$— linker to biphenyl system with $R^{3a}$, $R^{2a}$, $R^1$ substituents]

wherein:
$R^1$ is:

(a) —$SO_2N(R^{24})$—$OR^{24}$,
(b) —$SO_2NHSO_2R^{23}$, (c) —$SO_2NH$—$\overset{\overset{O}{\|}}{P}(R^{25})_2$, (d) —$SO_2NHCN$,
(e) —$SO_2NHCO_2R^{23}$, (f) —$SO_2NHSO_2$—N⟨ ⟩Z, (g) —$SO_2NHSO_2$—N⟨$R^4 \atop R^9$⟩, (h) —$NHSO_2NHSO_2R^{23}$, or (i) —$NHSO_2NH\overset{\overset{O}{\|}}{P}(R^{25})_2$;

(j) 
$$-\underset{\underset{\underset{O}{\|}}{S}}{\overset{R^{26}\ R^{26}}{N}}\diagdown\overset{O}{\diagup}\diagdown NH$$

(k) 
$$\overset{Y-N}{\underset{N}{\diagdown\diagup}}\diagdown NHSO_2R^{23}$$

(l) 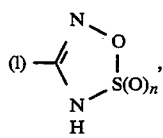, (m) 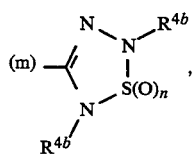, (n) 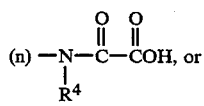, or (o) —NHSO$_2$R$^{23}$;

R$^{2a}$ is:
(a) H,
(b) C$_1$–C$_6$-alkyl,
(c) C$_1$–C$_6$-alkoxy, 

(d) CH$_2$—C$_1$–C$_6$-alkoxy,
(e) CH$_2$—S—C$_1$–C$_6$-alkyl,
(f) CH$_2$NR$^9$R$^9$, or
(g)

CH$_2$N⟨O⟩;

R$^{3a}$ is:
(a) H, or
(b) Cl, Br, I, or F;

R$^6$ is C$_1$–C$_6$-alkyl, C$_2$–C$_6$-alkenyl, —O—C$_1$–C$_4$-alkyl, or C$_3$–C$_7$-cycloalkyl; and R$^{7a}$ and R$^{7b}$ independently are:
(a) hydrogen,
(b) C$_1$–C$_6$-alkyl or C$_2$–C$_6$-alkenyl,
(c) —CO$_2$R$^4$ or —CO$_2$R$^{23}$,
(d) —CON(R$^4$)$_2$, or
(e) —NR$^4$R$^{4b}$.

Exemplifying this subclass are the following compounds of the Formula II wherein R$^{3a}$ is defined as a H or 3-F and all other substitutents are as defined in Table A below:

TABLE A

| Compound No | R$^1$ | R$^6$ | R$^{7a}$ | R$^{7b}$ | R$^{2a}$ |
|---|---|---|---|---|---|
| A1 | —SO$_2$NHOH | Et | Me | Me | n-Pr |
| A2 | —SO$_2$NHSO$_2$Ph | Et | Me | Me | Et |
| A3 | —SO$_2$NHSO$_2$Me | Et | Me | Me | CH$_2$SCH$_3$ |
| A4 | —SO$_2$NHSO$_2$—⟨i-Pr⟩ | Pr | CO$_2$H | Me | OCH$_3$ |
| A5 | (isoxathiazoline, NH) | Et | Me | Me | Et |
| A6 | (N-Ph thiadiazoline, NH) | Et | Me | Me | OEt |
| A7 | —NH—C(O)—CO$_2$H | Et | CO$_2$H | Me | t-Bu |
| A8 | —SO$_2$NHSO$_2$—⟨i-Pr⟩ | Et | Me | Me | i-Pr |
| A9 | —SO$_2$NHP(O)(O—CH$_2$Ph)$_2$ | Et | Me | Me | i-Bu |
| A10 | (cyclic sulfamide-oxo) | Et | Me | Me | CH$_2$N(CH$_3$)$_2$ |
| A11 | (isoxazole —NHSO$_2$Ph) | Et | Me | Me | Et |

TABLE A-continued

| Compound No | R¹ | R⁶ | R⁷ᵃ | R⁷ᵇ | R²ᵃ |
|---|---|---|---|---|---|
| A12 | (structure: 5-membered ring with N, O, N-S(=O)₂, NH, methyl) | Et | Me | Me | n-Pr |
| A13 | —SO₂NHCOOC₂H₅ | Et | Me | Me | n-Pr |
| A14 | —SO₂NHCOOCH₂Ph | Et | Me | Me | Et |
| A15 | —SO₂NHCOOBu | Et | Me | Me | OEt |
| A16 | —SO₂NHCOOCH₂c-Pr | Et | Me | Me | CH₂SCH₃ |
| A17 | —SO₂NHOH | Pr | Me | CONH₂ | t-Bu |
| A18 | —SO₂NHCOO-tBu | Et | Me | COOH | CH₂N[CH₂CH₂]₂O |
| A19 | —SO₂NHCOO-tBu | Et | Me | Me | i-Bu |
| A20 | —SO₂NHCOO-Et | Et | Me | NMe₂ | Et |
| A21 | —SO₂NHCOO-Bu | Et | Me | COOH | n-Pr |
| A22 | —SO₂NHOH | Et | Me | NMe₂ | n-Pr |
| A23 | —SO₂NHCO₂(CH₂)₂OEt | Et | Me | Me | n-Pr |
| A24 | —SO₂NHCO₂(CH₂)₂OEt | Et | Me | Me | i-Bu |
| A25 | —SO₂NHCO₂(CH₂)₂OEt | Et | Me | Me | OEt |
| A26 | —SO₂NHCO₂Bu | Et | Me | Me | OCH₂CF₃ |
| A27 | —SO₂NHCO₂CH₂Ph | Et | Me | Me | n-Pr |
| A28 | —SO₂NHCO₂CH₂Ph | Et | Me | Me | OEt |
| A29 | —SO₂NHCO₂CH₂Ph | Et | Me | Me | i-Bu |
| A30 | —SO₂NHCO₂CH₂Ph | Et | Me | Me | n-Bu |
| A31 | —SO₂NHCO₂Bu | Et | Me | Me | Et |
| A32 | —SO₂NHOH | Et | Me | Me | H |
| A33 | —SO₂NHSO₂Ph | Et | Me | Me | H |
| A34 | —SO₂NHSO₂Me | Et | Me | Me | H |
| A35 | —SO₂NHSO₂—⟨i-Pr⟩ | Pr | CO₂H | Me | H |
| A36 | (structure: 5-membered ring N-O-S(=O)-N(H), methyl) | Et | Me | Me | H |
| A37 | (structure: 5-membered ring with N-Ph, N-S(=O), NH, methyl) | Et | Me | Me | H |
| A38 | —NH—C(=O)—CO₂H | Et | CO₂H | Me | H |
| A39 | —SO₂NHSO₂—⟨i-Pr⟩ | Et | Me | Me | H |
| A40 | —SO₂NHP(=O)(O—CH₂Ph)₂ | Et | Me | Me | H |
| A41 | (structure: 5-membered ring with N, C=O, S(=O)₂, N-H) | Et | Me | Me | H |
| A42 | (structure: N—O, N ring with —NHSO₂Ph) | Et | Me | Me | H |
| A43 | (structure: 5-membered ring N-O-S(=O)₂-N(H), methyl) | Et | Me | Me | H |

TABLE A-continued

| Compound No | R¹ | R⁶ | R⁷ᵃ | R⁷ᵇ | R²ᵃ |
|---|---|---|---|---|---|
| A44 | —SO₂NHCO₂Bu | Et | Me | Me | N—Bu |
| A45 | —SO₂NHCO₂Bu | Et | Me | Me | N—Pr. |

Further illustrating this particular subclass are the compounds of Formula (II) wherein $R^1$ is:
(a) —SO₂N(R²⁴)—OR²⁴,
(b) —SO₂NHSO₂R²³,
(c)

(d) —SO₂NHCN,
(e) —SO₂NHCO₂R²³, (f) 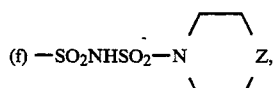

(g) 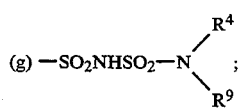

$R^{2a}$ is:
(a) H,
(b) $C_1$–$C_6$-alkyl, or
(c) $CH_2$—$C_1$–$C_6$-alkoxy;

$R^6$ is $C_1$–$C_6$-alkyl; and $R^{7a}$ and $R^{7b}$ independently are hydrogen, $C_1$–$C_6$-alkyl or $CO_2R^4$.

A particular subclass of this embodiment includes the compounds of Formula (III);

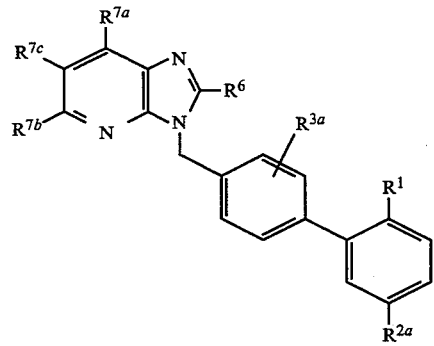

III wherein:
$R^1$ is:

(a) —SO₂N(R²⁴)—OR²⁴,
(b) —SO₂NHSO₂R²³, (c) 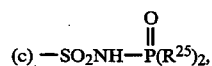

(d) —SO₂NHCN,
(e) —SO₂NHCO₂R²³, (f) 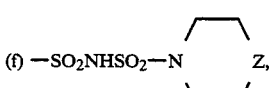

(g) 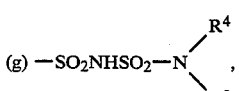

(h) —NHSO₂NHSO₂R²³, (i) 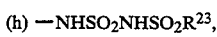

(j) 

(k) 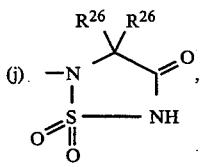

(l) 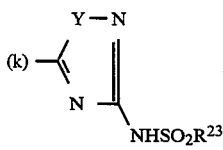

(m) 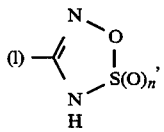

(n) 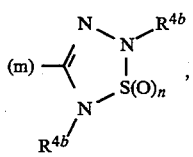

(o) —NHSO₂R²³;

$R^{2a}$ is:
(a) H,
(b) $C_1$–$C_6$-alkyl,
(c) $C_1$–$C_6$-alkoxy,
(d) $CH_2$—$C_1$–$C_6$-alkoxy,
(e) $CH_2$—S—$C_1$–$C_6$-alkyl,
(f) $CH_2NR^9R^9$, or
(g)

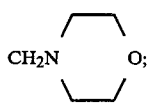

and
R$^{3a}$ is:
(a) H, or
(b) Cl, Br, I, or F;
R$^6$ is C$_1$-C$_6$-alkyl, C$_2$-C$_6$-alkenyl, —O—C$_1$-C$_4$-alkyl or C$_3$-C$_7$-cycloalkyl; and
R$^{7a}$ and R$^{7b}$ independently are:
(a) hydrogen,
(b) C$_1$-C$_6$ alkyl or C$_2$-C$_6$ alkenyl,
(c) —CO$_2$R$^4$ or —CO$_2$R$^{23}$, or
(d) —CON(R$^4$)R$^{23}$; and
R$^{7c}$ is:

(a) 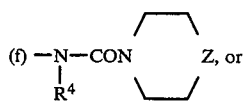

(b) —NHSO$_2$NHR$^{23}$,
(c) —N(R$^4$)CO$_2$R$^{23}$, (d) 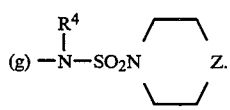

(e) —NHSO$_2$R$^{23}$, (f) 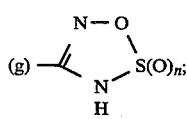

(g) 
$$-\underset{\underset{R^4}{|}}{N}-SO_2N\diagup\diagdown Z.$$

Illustrating this particular subclass are the compounds of Formula (III) wherein
R$^1$ is:
(a) —SO$_2$NHCO$_2$R$^{23}$,
(b) —SO$_2$NH(R$^{24}$)OR$^{23}$,
(c) —NHSO$_2$R$^{23}$,
(d) —SO$_2$NHSO$_2$R$^{23}$,
(e) —NHSO$_2$NHSO$_2$R$^{23}$
(f) —SO$_2$NHCN, or (g) 
$$\begin{array}{c}N-O\\ \diagup\phantom{xx}\diagdown\\ \phantom{xx}N\phantom{xx}S(O)_n;\\ \phantom{xx}H\end{array}$$

R$^{2a}$ is:
(a) H,
(b) C$_1$-C$_6$-alkyl, or
(c) CH$_2$—C$_1$-C$_6$-alkoxy;
R$^6$ is C$_1$-C$_6$-alkyl; and
R$^{7a}$ and R$^{7b}$ independently are hydrogen, C$_1$-C$_6$-alkyl or CO$_2$R$^4$.

Exemplifying this subclass are the following compounds of the Formula III shown in Tables B-E below:

TABLE B

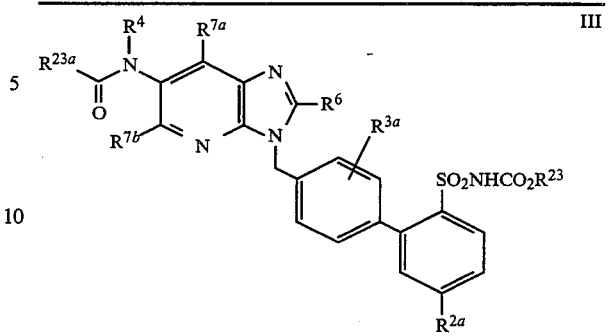

III wherein: R$^{7a}$ is H, or Me; and R$^{7b}$ is H, Me, or CO$_2$H; and R$^6$ is Et, Pr, or Bu; and R$^{2a}$ is H, Et, Pr, n-Bu, or i-Bu; and R$^{3a}$ is H or 3-F; and R$^4$ is H, or CH$_3$ and R$^{23}$ and R$^{23a}$ are as defined below:

| R$^{23}$ | R$^{23a}$ |
|---|---|
| -n-Pr | -n-Bu |
| -n-Bu | -n-Bu |
| -n-Hexyl | -n-Bu |
| —CH$_2$CH(CH$_3$)$_2$ | -n-Bu |
| —CH$_2$CH$_2$CH(CH$_3$)$_2$ | -n-Bu |
| —CH$_2$CH(CH$_3$)CH(CH$_3$)$_2$ | -n-Bu |
| —CH$_2$(C$_5$H$_9$) | -n-Bu |
| —CH$_2$CH$_2$(C$_5$H$_9$) | -n-Bu |
| —CH$_2$(C$_6$H$_{11}$) | -n-Bu |
| —CH$_2$CH$_2$(C$_6$H$_{11}$) | -n-Bu |
| —CH$_2$(C$_6$H$_5$) | -n-Bu |
| —CH$_2$CH$_2$C$_6$H$_5$ | -n-Bu |
| —CH(CH$_3$)CH$_2$CH$_3$ | -n-Bu |
| —CH(CH$_3$)CH$_2$CH$_2$CH$_3$ | -n-Bu |
| —C(CH$_3$)$_2$CH$_2$CH$_3$ | -n-Bu |
| —C(CH$_3$)$_2$CH$_2$CH$_2$CH$_3$ | -n-Bu |
| —CHC(CH$_3$)$_2$ | -n-Bu |
| —CH$_2$CH$_2$OCH$_3$ | -n-Bu |
| —CH$_2$CH$_2$OCH$_2$CH$_3$ | -n-Bu |
| —CH$_2$CH$_2$OCH(CH$_3$)$_2$ | -n-Bu |
| -cyclopropane | -n-Bu |
| 2,2-dimethylcyclopropane-1-yl | -n-Bu |
| —C$_5$H$_9$ | -n-Bu |
| —C$_6$H$_5$ | -n-Bu |
| —C$_6$H$_{11}$ | -n-Bu |
| —CH$_2$-thiophene-2-yl | -n-Bu |
| —CH$_2$-thiophene-3-yl | -n-Bu |
| —CH$_2$-furan-2-yl | -n-Bu |
| —CH$_2$-furan-3-yl | -n-Bu |
| -n-Pr | Pr |
| -n-Bu | Pr |
| -n-Hexyl | Pr |
| —CH$_2$CH(CH$_3$)$_2$ | Pr |
| —CH$_2$CH$_2$CH(CH$_3$)$_2$ | Pr |
| —CH$_2$(C$_5$H$_9$) | Pr |
| —CH$_2$CH$_2$(C$_5$H$_9$) | Pr |
| —CH$_2$(C$_6$H$_{11}$) | Pr |
| —CH$_2$CH$_2$(C$_6$H$_{11}$) | Pr |
| —CH$_2$(C$_6$H$_5$) | Pr |
| —CH$_2$CH$_2$(C$_6$H$_5$) | Pr |
| —CH$_2$CH$_2$OCH$_3$ | Pr |
| -n-Pr | Et |
| -n-Bu | Et |
| -n-Hexyl | Et |
| —CH$_2$CH(CH$_3$)$_2$ | Et |
| —CH$_2$CH$_2$CH(CH$_3$)$_2$ | Et |
| —CH$_2$(C$_5$H$_9$) | Et |
| —CH$_2$CH$_2$(C$_5$H$_9$) | Et |
| —CH$_2$(C$_6$H$_{11}$) | Et |
| —CH$_2$CH$_2$(C$_6$H$_{11}$) | Et |
| —CH$_2$(C$_6$H$_5$) | Et |
| —CH$_2$CH$_2$(C$_6$H$_5$) | Et |
| —CH$_2$CH$_2$OCH$_3$ | Et |
| -n-Pr | Ph |
| -n-Bu | Ph |
| -n-Hexyl | Ph |
| —CH$_2$CH(CH$_3$)$_2$ | Ph |
| —CH$_2$CH$_2$CH(CH$_3$)$_2$ | Ph |
| —CH$_2$(C$_5$H$_9$) | Ph |
| —CH$_2$CH$_2$(C$_5$H$_9$) | Ph |
| —CH$_2$(C$_6$H$_{11}$) | Ph |

TABLE B-continued

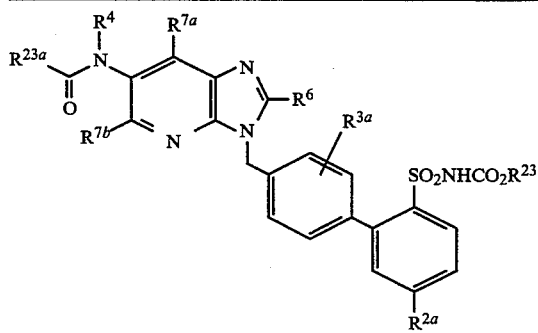

wherein: $R^{7a}$ is H, or Me; and $R^{7b}$ is H, Me, or $CO_2H$; and $R^6$ is Et, Pr, or Bu; and $R^{2a}$ is H, Et, Pr, n-Bu, or i-Bu; and $R^{3a}$ is H or 3-F; and $R^4$ is H, or $CH_3$ and $R^{23}$ and $R^{23a}$ are as defined below:

| $R^{23}$ | $R^{23a}$ |
|---|---|
| —$CH_2CH_2(C_6H_{11})$ | Ph |
| —$CH_2(C_6H_5)$ | Ph |
| —$CH_2CH_2(C_6H_5)$ | Ph |
| —$CH_2CH_2OCH_3$ | Ph |
| -n-Bu | -2-pyridyl |
| —$CH_2(C_5H_9)$ | -2-pyridyl |
| -n-Bu | -3-pyridyl |
| —$CH_2(C_5H_9)$ | -3-pyridyl |
| -n-Bu | -4-pyridyl |
| —$CH_2(C_5H_9)$ | -4-pyridyl |
| -n-Bu | -2-thienyl |
| —$CH_2(C_5H_9)$ | -2-thienyl |
| -n-Bu | -2-furyl |
| —$CH_2(C_5H_9)$ | -2-furyl. |

TABLE C

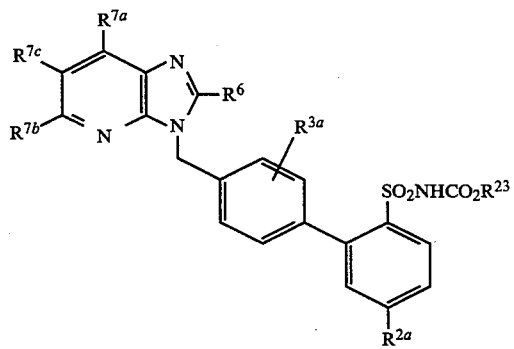

wherein $R^{7a}$ is H, or Me; and $R^{7b}$ is H, Me, or $CO_2H$; and $R^6$ is Et, Pr, or Bu; and $R^{2a}$ is H, Et, Pr, n-Bu, or i-Bu; and $R^{3a}$ is H or 3-F; and $R^4$ is H, or $CH_3$ and $R^{23}$ and $R^{23a}$ are as defined in the table below:

| $R^{23}$ | $R^{7c}$ |
|---|---|
| -n-Pr | —$NR^4CON(H)$-n-Pr |
| -n-Bu | —$NR^4CON(H)$-n-Pr |
| -n-Hexyl | —$NR^4CON(H)$-n-Pr |
| —$CH_2CH(CH_3)_2$ | —$NR^4CON(H)$-n-Pr |
| —$CH_2CH_2CH(CH_3)_2$ | —$NR^4CON(H)$-n-Pr |
| —$CH_2(C_5H_9)$ | —$NR^4CON(H)$-n-Pr |
| —$CH_2CH_2(C_5H_9)$ | —$NR^4CON(H)$-n-Pr |
| —$CH_2(C_6H_{11})$ | —$NR^4CON(H)$-n-Pr |
| —$CH_2CH_2(C_6H_{11})$ | —$NR^4CON(H)$-n-Pr |
| —$CH_2(C_6H_5)$ | —$NR^4CON(H)$-n-Pr |
| —$CH_2CH_2(C_6H_5)$ | —$NR^4CON(H)$-n-Pr |
| —$CH_2CH_2OCH_3$ | —$NR^4CON(H)$-n-Pr |
| -n-Pr | —$NR^4CON(H)$-i-Pr |
| -n-Bu | —$NR^4CON(H)$-i-Pr |
| -n-Hexyl | —$NR^4CON(H)$-i-Pr |
| —$CH_2CH(CH_3)_2$ | —$NR^4CON(H)$-i-Pr |
| —$CH_2CH_2CH(CH_3)_2$ | —$NR^4CON(H)$-i-Pr |
| —$CH_2(C_5H_9)$ | —$NR^4CON(H)$-i-Pr |
| —$CH_2CH_2(C_5H_9)$ | —$NR^4CON(H)$-i-Pr |
| —$CH_2(C_6H_{11})$ | —$NR^4CON(H)$-i-Pr |
| —$CH_2CH_2(C_6H_{11})$ | —$NR^4CON(H)$-i-Pr |

TABLE C-continued

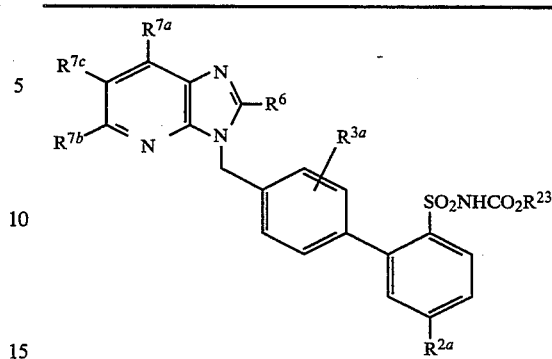

wherein $R^{7a}$ is H, or Me; and $R^{7b}$ is H, Me, or $CO_2H$; and $R^6$ is Et, Pr, or Bu; and $R^{2a}$ is H, Et, Pr, n-Bu, or i-Bu; and $R^{3a}$ is H or 3-F; and $R^4$ is H, or $CH_3$ and $R^{23}$ and $R^{23a}$ are as defined in the table below:

| $R^{23}$ | $R^{7c}$ |
|---|---|
| —$CH_2(C_6H_5)$ | —$NR^4CON(H)$-i-Pr |
| —$CH_2CH_2(C_6H_5)$ | —$NR^4CON(H)$-i-Pr |
| —$CH_2CH_2OCH_3$ | —$NR^4CON(H)$-i-Pr |
| -n-Pr | —$NR^4CON(Me)$-i-Pr |
| -n-Bu | —$NR^4CON(Me)$-i-Pr |
| -n-Hexyl | —$NR^4CON(Me)$-i-Pr |
| —$CH_2CH(CH_3)_2$ | —$NR^4CON(Me)$-i-Pr |
| —$CH_2CH_2CH(CH_3)_2$ | —$NR^4CON(Me)$-i-Pr |
| —$CH_2(C_5H_9)$ | —$NR^4CON(Me)$-i-Pr |
| —$CH_2CH_2(C_5H_9)$ | —$NR^4CON(Me)$-i-Pr |
| —$CH_2(C_6H_{11})$ | —$NR^4CON(Me)$-i-pr |
| —$CH_2CH_2(C_6H_{11})$ | —$NR^4CON(Me)$-i-Pr |
| —$CH_2(C_6H_5)$ | —$NR^4CON(Me)$-i-Pr |
| —$CH_2CH_2(C_6H_5)$ | —$NRN(Me^4CO)$-i-Pr |
| —$CH_2CH_2OCH_3$ | —$NR^4CON(Me)$-i-Pr |
| -n-Bu | —$NR^4CONHMe$ |
| —$CH_2(C_5H_9)$ | —$NR^4CONHMe$ |
| -n-Bu | —$NR^4CONHEt$ |
| —$CH_2(C_5H_9)$ | —$NR^4CONHEt$ |
| -n-Bu | —$NR^4CONMe_2$ |
| —$CH_2(C_5H_9)$ | —$NR^4CONMe_2$ |
| -n-Bu | —$NR^4CONEt_2$ |
| —$CH_2(C_5H_9)$ | —$NR^4CONEt_2$ |
| —$CH_2CH_2OCH_3$ | —$NR^4CONEt_2$ |
| -n-Bu | —$NR^4CO$-morpholine-4-yl |
| —$CH_2(C_5H_9)$ | —$NR^4CO$-morpholine-4-yl |
| -n-Bu | —$NR^4CO$-pyrrolidine-1-yl |
| —$CH_2(C_5H_9)$ | —$NR^4CO$-pyrrolidine-1-yl. |

TABLE D

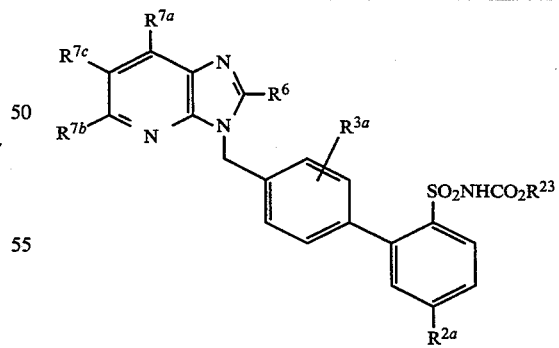

wherein $R^{7a}$ is H, or Me; and $R^{7b}$ is H, Me, or $CO_2H$; and $R^6$ is Et, Pr, or Bu; and $R^{2a}$ is H, Et, Pr, n-Bu, or i-Bu; and $R^{3a}$ is H or 3-F; and $R^{7c}$ and $R^{23}$ are as defined in the table below:

| $R^{7c}$ | $R^{23}$ |
|---|---|
| —$NHSO_2Pr$ | -n-Bu |
| —$NHSO_2Pr$ | —$CH_2CH(CH_3)_2$ |
| —$NHSO_2Pr$ | —$CH_2(C_6H_5)$ |
| —$NHSO_2Bu$ | -n-Bu |
| —$NHSO_2Bu$ | —$CH_2CH(CH_3)_2$ |
| —$NHSO_2Bu$ | —$CH_2(C_6H_5)$ |

TABLE D-continued

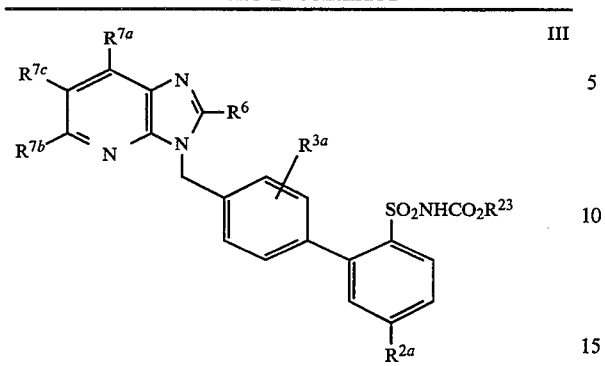

III wherein $R^{7a}$ is H, or Me; and $R^{7b}$ is H, Me, or $CO_2H$; and $R^6$ is Et, Pr, or Bu; and $R^{2a}$ is H, Et, Pr, n-Bu, or i-Bu; and $R^{3a}$ is H or 3-F; and $R^{7c}$ and $R^{23}$ are as defined in the table below:

| $R^{7c}$ | $R^{23}$ |
|---|---|
| —$NHSO_2$-morpholine-4-yl | -n-Bu |
| —$NHSO_2$-morpholine-4-yl | —$CH_2CH(CH_3)_2$ |
| —$NHSO_2$-morpholine-4-yl | —$CH_2(C_6H_5)$ |
| —$NHSO_2NHEt$ | -n-Bu |
| —$NHSO_2NHEt$ | —$CH_2CH(CH_3)_2$ |
| —$NHSO_2NHEt$ | —$CH_2(C_6H_5)$. |

TABLE E

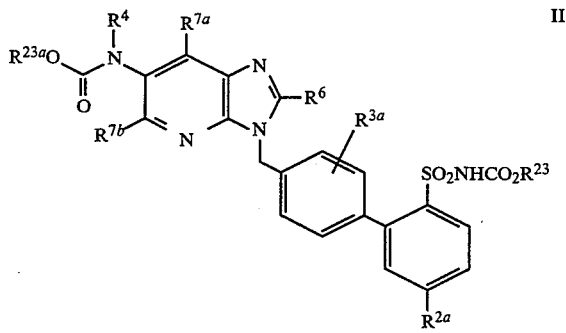

III wherein $R^{7a}$ is H, or Me; and $R^{7b}$ is H, Me, or $CO_2H$; and $R^6$ is Et, Pr, or Bu; $R^{2a}$ is H, Et, Pr, n-Bu or i-Bu; and $R^{3a}$ is H or 3-F; and $R^4$ is H, or $CH_3$ and $R^{23}$ and $R^{23a}$ are as defined in the table below:

| $R^{23}$ | $R^{23a}$ |
|---|---|
| -n-Bu | Et |
| —$CH_2CH(CH_3)_2$ | Et |
| —$CH_2(C_6H_5)$ | Et |
| -n-Bu | Pr |
| —$CH_2CH(CH_3)_2$ | Pr |
| —$CH_2(C_6H_5)$ | Pr |
| -n-Bu | Ph |
| —$CH_2CH(CH_3)_2$ | Ph |
| —$CH_2(C_6H_5)$ | Ph |
| -n-Bu | -i-Pr |
| —$CH_2CH(CH_3)_2$ | -i-Pr |
| —$CH_2(C_6H_5)$ | -i-Pr |
| —$CH_2CH_2OCH_3$ | Ph |
| —$CH_2CH_2OCH_3$ | -i-Pr. |

A third subclass of this embodiment includes the compounds of Formula (IV):

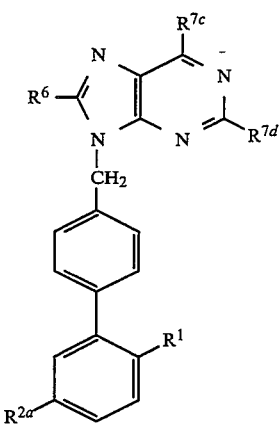

wherein:
$R^1$ is:

(a) —$SO_2NR^{24}OR^{24}$, (b) —$SO_2NHSO_2R^{23}$, (c) 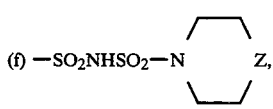

(d) —$SO_2NHCN$, (e) —$SO_2NHCO_2R^{23}$, (f) 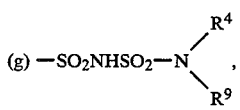

(g) 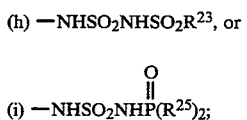

(h) —$NHSO_2NHSO_2R^{23}$, or (i) 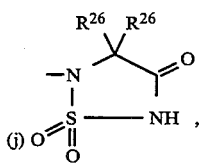

(j) 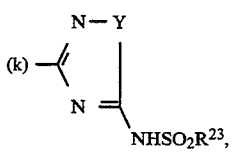

(k) 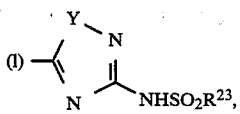

(l)

-continued (m) 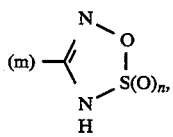

(n) 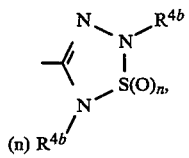

(o) —NHSO$_2$R$^{23}$;

R$^6$ is a C$_1$-C$_6$-alkyl or C$_2$-C$_6$ alkenyl or C$_3$-C$_7$-cycloalkyl; and R$^{7c}$ and R$^{7d}$ independently are:
(a) hydrogen,
(b) C$_1$-C$_6$ alkyl or C$_2$-C$_6$ alkenyl,
(c) —CO$_2$R$^4$,
(d) —CON(R$^4$)$_2$,
(e) —NH$_2$,
(f)

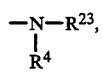

wherein R$^{23}$ is C$_1$-C$_4$-alkyl, phenyl or polyfluoro C$_1$-C$_4$-alkyl, or (g) 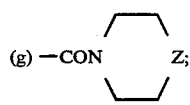

wherein Z is CH$_2$, O, or S.

Illustrating this third subclass are the compounds of Formula (IV) wherein
R$^1$ is:

(a) —SO$_2$N(R$^{24}$)—OR$^{24}$, (b) —SO$_2$NHSO$_2$R$^{23}$, (c) 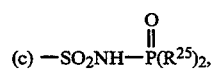

(d) —SO$_2$NHCN, (e) —SO$_2$NHCO$_2$R$^{23}$, (f) 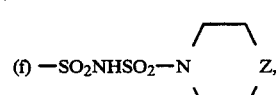

(g) 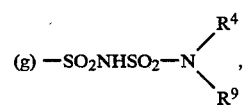

-continued (h) 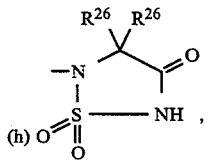

(i) 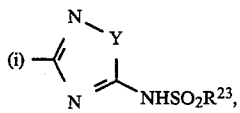

(j) 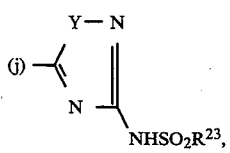

(k) 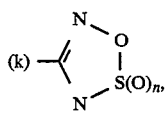

(l) 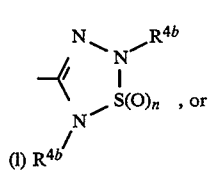

(m) —NHSO$_2$R$^{23}$;

R$^6$ is C$_1$-C$_6$-alkyl; and
R$^{7c}$ and R$^{7d}$ independently are hydrogen, C$_1$-C$_6$ alkyl, CO$_2$R$^4$ or N(R$^4$)R$^{23}$.

Exemplifying this third subclass are the following compounds of the Formula (IV), wherein R$^{2a}$ is H, Et, Pt, n-Bu or i-Bu, shown in Table F;

TABLE F

| Compound No. | R$^1$ | R$^6$ | R$^{7c}$ | R$^{7d}$ |
|---|---|---|---|---|
| F1 | —SO$_2$NHOH | Pr | Me | —NHCH$_3$ |
| F2 | —SO$_2$NHOH | Pr | Me | —N⏜O |
| F3 | —SO$_2$NHSO$_2$—⟨ | Pr | Me | —N⏜O |
| F4 | —SO$_2$NH—SO$_2$Ph | Et | Me | —NHCH$_3$ |
| F5 | —SO$_2$NHP(O)(OCH$_2$Ph)(OCH$_2$Ph) | Pr | Me | —N⏜O |
| F6 | (cyclic sulfonamide) | Et | Me | —N⏜O |

TABLE F-continued

| Compound No. | R¹ | R⁶ | R⁷ᶜ | R⁷ᵈ |
|---|---|---|---|---|
| F7 | " | Pr | Me | —NHCH₃ |
| F8 | [structure: N-O ring with NHSO₂Ph] | Pr | Me | [morpholine ring] |
| F9 | [structure: N-N-Ph ring with S=O, NH] | Pr | Me | —NHCH₃ |
| F10 | [structure: N-O-S=O ring with NH] | Et | Me | [morpholine ring] |
| F11 | [structure: O-N ring with NHSO₂CF₃] | Pr | Me | [morpholine ring] |
| F12 | —SO₂NHCO₂Bu | Pr | Me | Me |
| F13 | —SO₂NHCO₂Bu | Pr | Me | [morpholine ring] |

A fourth subclass of this embodiment includes the compounds of Formula (V)

[Chemical structure of Formula (V): imidazo-fused pyrimidinedione with R⁶, R⁸ᵇ, R⁸ᶜ substituents and a CH₂-biphenyl group bearing R¹ and R²ᵃ]

wherein:
R¹ is:
(a) —SO₂NR²⁴OR²³,
(b) —SO₂NHSO₂R²³,
(c) —SO₂NHP(O)(R²⁵)₂,
(d) —SO₂NHCN,
(e) —SO₂NHCO₂R²³, (f) —SO₂NHSO₂—N⌒Z, (piperazine-like ring)

(g) —SO₂NHSO₂—NR⁴R⁹, (h) —NHSO₂NHSO₂R²³, (i) —NHSO₂NHP(O)(R²⁵)₂, (j) [structure with R²⁶, S(O)₂, NH, C=O]

(k) [structure with N=Y ring, NHSO₂R²³], or (l) —NHSO₂R²³;

R²ᵃ is:
(a) H,
(b) C₁-C₆-alkyl,
(c) C₁-C₆-alkoxy,
(d) CH₂—C₁-C₆-alkoxy,
(e) CH₂—S—C₁-C₆-alkyl,
(f) CH₂NR⁹R⁹, or
(g) CH₂N⌒O (morpholine);

and
R⁶ is C₁-C₆-alkyl or C₂-C₆-alkenyl or C₃-C₇-cycloalkyl; and
R⁸ᵇ and R⁸ᶜ independently are:
(a) hydrogen, or
(b) C₁-C₆ alkyl or C₂-C₆ alkenyl.

Illustrating this forth subclass are the compounds of Formula (V) wherein
R¹ is:

(a) —SO₂NR²⁴OR²³, (b) —SO₂NHSO₂R²³, (c) —SO₂NHP(O)(R²⁵)₂, (d) —SO₂NHCN, (e) —SO₂NHCO₂R²³, (f) —SO₂NHSO₂—N⌒Z, (g) 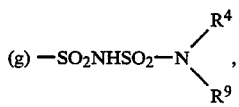

(j) 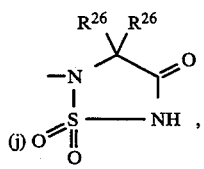

(k) 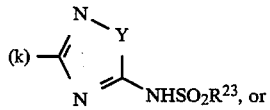

(l) —NHSO₂R²³;

$R^6$ is $C_1$–$C_6$-alkyl; and
$R^{8b}$ and $R^{8c}$ independently are hydrogen, or $C_1$–$C_6$-alkyl.

Exemplifying this forth subclass are the following compounds of the Formula (V) wherein $R^{2a}$ is H, Et, Pt, n-Bu or i-Bu shown in Table G.

TABLE G

| Compound No. | $R^1$ | $R^6$ | $R^{8b}$ | $R^{8c}$ |
|---|---|---|---|---|
| G1 | —SO₂NHOH | nPr | Me | Me |
| G2 | —SO₂NHOH | nBu | Me | Me |
| G3 | —SO₂NHSO₂Ph | nPr | Me | Me |
| G4 | 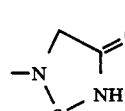 | nPr | Me | Me |
| G5 | 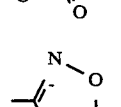 | nBu | Me | Me |
| G6 | —SO₂NHCO₂Et | nBu | Me | Me. |

The following numbering system has been used to name the compounds of the invention:

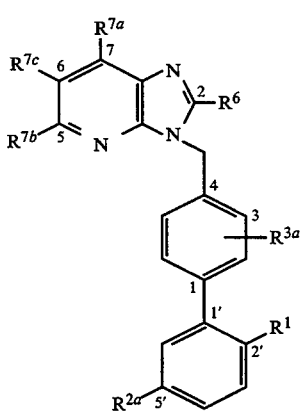

The compounds of Formula (I) can be synthesized using the reactions and techniques described herein below. The reactions are performed in a solvent appropriate to the reagents and materials employed and suitable for the transformation being effected. It is understood by those skilled in the art of organic synthesis that the functionality present on the heterocycle and in the reactants being employed should be consistent with the chemical transformations being conducted. Depending upon the reactions and techniques employed, optimal yields may require changing the order of synthetic steps or use of protecting groups followed by deprotection.

| ABBREVIATIONS USED IN REACTION SCHEMES | |
|---|---|
| Reagents: | |
| NBS | N-bromosuccinimide |
| AIBN | Azo(bis)isobutyronitrile |
| DDQ | Dichlorodicyanoquinone |
| Ac₂O | acetic anhydride |
| TEA | triethylamine |
| DMAP | 4-dimethylaminopyridine |
| PPh₃ | triphenylphosphine |
| TFA | trifluoroacetic acid |
| TMS-Cl | trimethylsilyl chloride |
| Im | imidazole |
| AcSK | potassium thioacetate |
| p-TsOH | p-toluenesulfonic acid |
| Solvents: | |
| Et₂O | diethyl ether |
| DMF | dimethylformamide |
| HOAc (AcOH) | acetic acid |
| EtOAc (EtAc) | ethyl acetate |
| Hex | hexane |
| THF | tetrahydrofuran |
| DMSO | dimethylsulfoxide |
| MeOH | methanol |
| iPrOH | isopropanol |
| DBU | 1,8-diazabicyclo-[5.4.0]undec-7-ene |
| Me₃SnCl | trimethylstannyl chloride |
| Others: | |
| rt | room temperature |
| TBDMS | t-butyldimethylsilyl |
| OTf | OSO₂CF₃ |
| OTs | OSO₂-(4-methyl)phenyl |
| OMs | OSO₂CH₃ |
| Ph | phenyl |
| FAB-MS (FABMS) | Fast atom bombardment mass spectroscopy |
| NOE | Nuclear Overhauser Effect |
| SiO₂ | silica gel |
| trityl | triphenylmethyl |

As shown in Scheme 1, compounds of Formula (I) can be prepared by carrying out direct alkylation of alkali-metal salts of heterocycles (1) using appropriately protected benzyl halide, tosylate (OTs) or mesylate (OMs) derivatives (2). The salt is prepared preferably using MH (where M is lithium, sodium or potassium) or K₂CO₃ or CsCO₃ in anhydrous dimethylformamide (DMF), or by treating it with a metal alkoxide such as sodium or potassium methoxide, ethoxide or t-butoxide in an appropriate alcohol such as methanol, ethanol or t-butanol as the solvent. The alkylation is generally carried out by dissolving the metal salt of the heterocycle in a dipolar aprotic solvent such as DMF or dimethylsulfoxide (DMSO) and reacting it with the alkylating agent at 20° C. to reflux temperature of the solvent for 1–24 hours.

SCHEME 1

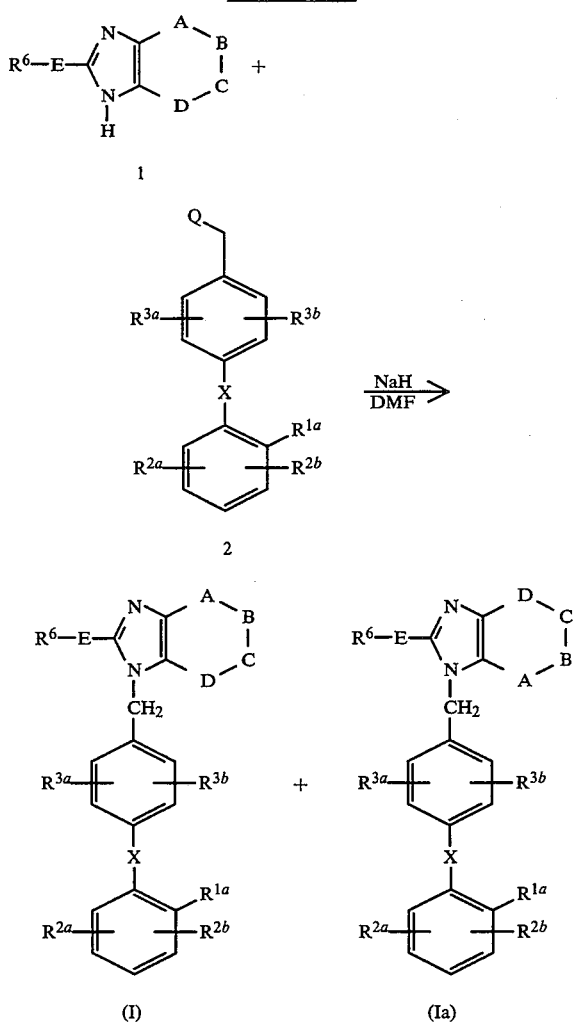

where Q = I, Br, Cl, —O-tosyl, —O-mesyl and
$R^{1a}$ = —NO$_2$, —CN, —COOC(CH$_3$)$_3$, —SO$_2$NHC(CH$_3$)$_3$ If substituents and/or the heteroatom positions in the six-membered ring are not symetrically disposed, the alkylation on the imidazole nitrogen(s) generally produces a mixture of two regioisomers as products arising from $N^1$ and $N^3$ alkylation. These regioisomers I and Ia possess distinct physiochemical and biological properties and in most cases can be separated and purified by using conventional separation techniques such as chromatography (flash column chromatography, medium-pressure liquid chromatography, high performance liquid chromatography) and/or crystallization. In those cases where separation of regioisomers is difficult by conventional techniques, the mixture can be transformed into suitable derivatives that can be separated by the above separation methods. The structural assignments of the isomers can be made using Nuclear Overhauser Effect (NOE), $^1$H-$^{13}$C coupled NMR experiments or X-ray crystallography.

When there is potential for alkylation on the 6-membered heterocyclic ring, this can be avoided by the use of suitable protecting groups.

The substituted benzyl halides (2) including the more preferred alkylating agents (8a and 8b and 8c, Scheme 2) can be prepared as described in European Patent Applications 253,310 and 291,969 and the references cited therein. In addition a preferred method to prepare the biphenyl precursors 7a, 7b using Ni(O) or Pd(O) catalyzed cross-coupling reaction [E. Negishi, T. Takahashi, and A. O. King, Org. Synthesis, 66, 67 (1987)] is outlined in Scheme 2. As shown in Scheme 2, treatment of 4-bromotoluene (3) with t-BuLi, followed by the addition of a solution of ZnCl$_2$, produces the organo-zinc compound (5). Compound (5) is then coupled with (6a) or (6b) in the presence of Ni(PPh$_3$)Cl$_2$ catalyst to produce the desired biphenyl compound (7a) or (7b). Similarly, 1-bromo-2-nitrobenzene (6c) is coupled with organo-zinc compound (5) in the presence of Pd(PPh$_3$)$_4$ catalyst [prepared by treating Cl$_2$Pd(PPh$_3$)$_2$ with (i-Bu)$_2$AlH (2 equiv.)] to give the biphenyl compound (7c). These precursors, (7a), (7b) and (7c), are then transformed into halomethylbiphenyl derivatives (8a), (8b) and (8c), respectively, according to procedures described in European Patent Applications 253,310 and 291,969.

When there is additional substitution on the second phenyl ring ($R^2$ not hydrogen) the preferred method to prepare the biphenyl precursors (7d) and (7e), using the Pd(O) catalyzed cross-coupling reaction [J. K. Stille, Angew. Chem. Int. Ed. Engl., 25, 508 (1986)], is outlined in reaction Scheme 2a. As shown in Scheme 2a, p-tolyl-trimethyltin (5a) is coupled with (6d) or (6e) in refluxing toluene in the presence of 5 mole % of Pd(PPh$_3$)$_4$ to produce the desired biphenyl compounds (7d) and (7e). Table I illustrates the synthetic utility of this protocol. Compounds (7d) ($R^2$=NO$_2$) and (7e) ($R^2$=NO$_2$) could be converted to their respective chlorides by catalytic hydrogenation, diazotization and treatment with copper (I) chloride. The biphenyl fluorides which could not be obtained by direct coupling to a fluoro arylbromide were prepared from (7d) ($R^2$=NO$_2$) and (7e) ($R^2$=NO$_2$) via reduction, formation of the diazonium tetrafluoroborate salt and thermal decomposition. These precursors (7d) ($R^2$=NO$_2$ or F or Cl) and (7e) ($R^2$=NO$_2$ or F or Cl) are then transformed into the halomethyl biphenyl derivatives (8d) and (8e), respectively according to the procedures described in European Patent Applications 253,310 and 292,969.

SCHEME 2

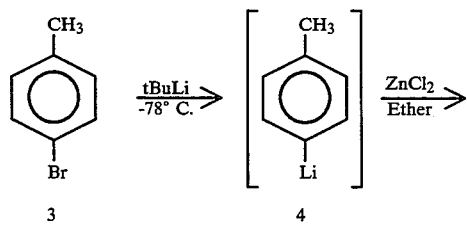

-continued
SCHEME 2

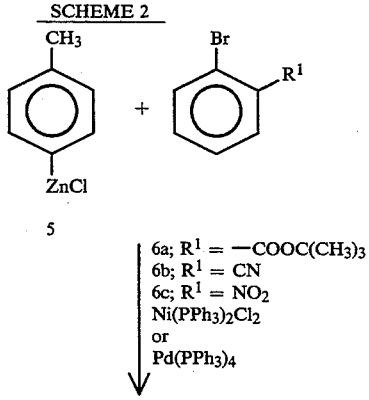

6a; $R^1 = -COOC(CH_3)_3$
6b; $R^1 = CN$
6c; $R^1 = NO_2$
$Ni(PPh_3)_2Cl_2$
or
$Pd(PPh_3)_4$

-continued
SCHEME 2a

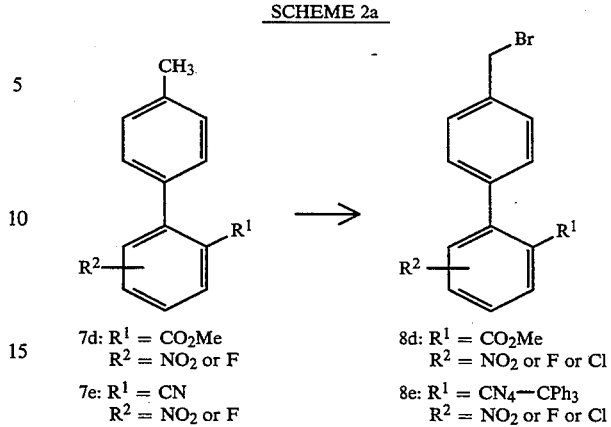

7d: $R^1 = CO_2Me$
$R^2 = NO_2$ or F

7e: $R^1 = CN$
$R^2 = NO_2$ or F

8d: $R^1 = CO_2Me$
$R^2 = NO_2$, F or Cl

8e: $R^1 = CN_4-CPh_3$
$R^2 = NO_2$, F or Cl

TABLE I

Biphenyl Synthesis

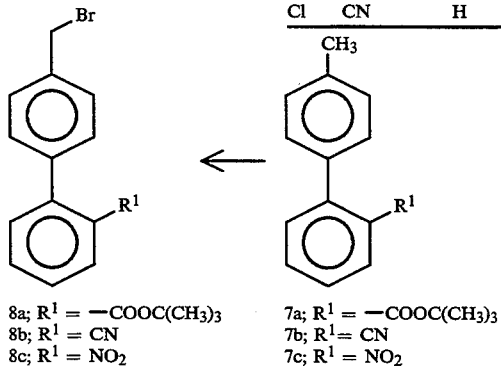

| X | $R^1$ | $R^a$ | $R^b$ | $R^c$ | $R^d$ | Product ($R^2$) | Rf (solvent) | Yield |
|---|---|---|---|---|---|---|---|---|
| Br | $CO_2Me$ | $NO_2$ | H | H | H | 7d (3'-nitro) | 0.35(15:1 Hex/EtOAc) | 71% |
| Br | CN | H | $NO_2$ | H | H | 7e (4'-nitro) | 0.62(2x 6:1 Hex/EtOAc) | 74% |
| Br | $CO_2Me$ | H | F | H | E | 7d (4'-fluoro) | 0.43(15:1 Hex/EtOAc) | 83% |
| Cl | $CO_2Me$ | H | H | $NO_2$ | H | 7d (5'-nitro) | 0.22(15:1 Hex/EtOAc) | 70% |
| Br | $CO_2Me$ | H | H | H | $NO_2$ | 7d (6'-nitro) | 0.24(15:1 Hex/EtOAc) | 79% |
| Br | CN | H | F | H | H | 7e (4'-fluoro) | 0.44(15:1 Hex/EtOAc) | 64% |
| Cl | CN | H | H | F | H | 7e (5'-fluoro) | 0.40(15:1 Hex/EtOAc) | 62% |

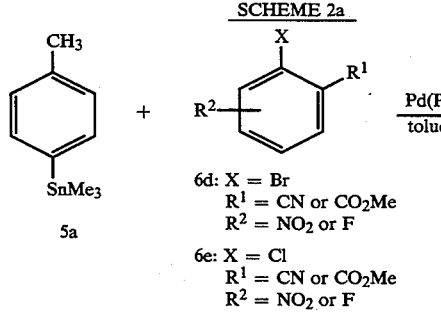

8a; $R^1 = -COOC(CH_3)_3$
8b; $R^1 = CN$
8c; $R^1 = NO_2$

7a; $R^1 = -COOC(CH_3)_3$
7b; $R^1 = CN$
7c; $R^1 = NO_2$

SCHEME 2a

[structure with 5a + 6d/6e → Pd(PPh_3)_4 / toluene Δ]

6d: X = Br
$R^1 = CN$ or $CO_2Me$
$R^2 = NO_2$ or F

6e: X = Cl
$R^1 = CN$ or $CO_2Me$
$R^2 = NO_2$ or F

The heterocycles of type (1) can be prepared by any of the standard procedures described in the literature [J. A. Montgomery and J. A. Secrist III in "Comprehensive Heterocyclic Chemistry," Vol. 5, A. R. Katritsky and C. W. Rees eds., Pergamon Press 1984; pp 567–597 and 631–656 and references cited therein]. As shown in Scheme 3, the most widely used starting materials are six member heterocyclic vicinal diamines (9). Fused imidazoles (10) can be prepared by condensation of (9) with an appropriate carboxylic acid, nitrile, imidate ester, or orthoesters, either neat, or in a solvent appropriate and compatible with the starting materials and reagents, such as polyphosphoric acid, ethanol, methanol, hydrocarbon solvents, and with a catalytic amount of acid if required. Oxidation of an imine formed by reaction of diamine (9) with an appropriate aldehyde using oxidants such as Cu (II), nitrobenzene, or 2,3-dichloro-5,6-dicyano-1,4-benzoquinone (DDQ) also affords heterocycles (10). Aminoamides (11, W=H) or diamides (11, W=$R^6$CO) can be converted to fused imidazoles (10) by heating neat, or at an elevated temperature in a solvent such as xylene under acidic or neutral conditions.

SCHEME 3

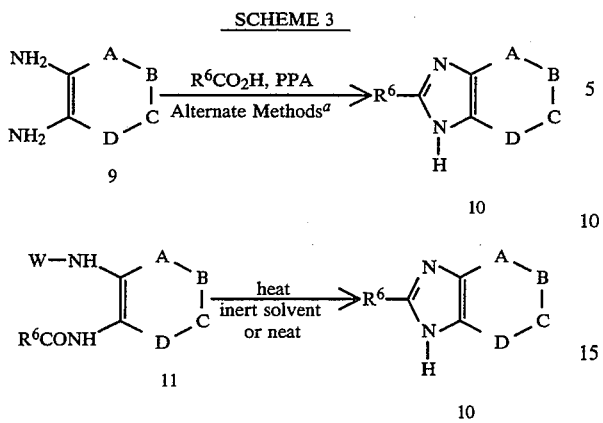

W = H or R⁶CO

ᵃAlternate reagents and reaction conditions:
R⁶C≡N, PPA;

$$R^6-\underset{\underset{OC_2H_5}{|}}{C}=NH \cdot HCl,\ C_2H_5OH,\ \Delta;$$

R⁶C(OCH₃)₃, toluene, H⁺, Δ; and
R⁶CHO, C₂H₅OH, Cu(OCOCH₃)₂.

As shown in Scheme 4, methods of preparing heterocycles of types (12 and 13) involve treatment of diamines (9) with reagents such as urea, phosgene, potassium cyanate, alkyl chloroformates, dialkylcarbonate, or carbon disulfide in the presence of bases such as potassium hydroxide or potassium carbonate. Amino acids (14) or (15) can be converted to (13) via Curtius or Hoffman rearrangement on suitable derivatives such as acyl azides, hydroxyamides, or N-haloamides. Bicyclic compounds of type (16, E=sulfur or oxygen) are formed from (12) by reaction under neutral or basic conditions with alkyl halides, alkylmesylates, alkyltosylates, trialkyloxonium salts, or with an appropriate diazoalkane. Compounds of type (16; E=oxygen or sulfur) are prepared by displacement reactions using alkoxides or alkyl mecaptides with chloro intermediates as indicated.

Diamines of type (9) can be prepared by a wide variety of methods such as hydrolysis of bis-amides or amino amides, reduction of dinitro or aminonitro or hydrazino or azido groups, displacement of heteroaromatic halides or alkoxy or thio or alkylthio or hydroxy or alkyl sulfonyl groups with ammonia or amines, or rearrangement of acyl azides or amides or acids (Curtius, Hoffman, or Schmidt rearrangements). [A. S. Tomcufcik, L. N. Starker in "Heterocyclic Compounds, Pyridine and it's Derivatives" Pt 3, E. Klingsberg Ed., Wiley Interscience, 1962, pp 59–62, and references cited there in; T. Nakagome in "Heterocyclic Compounds, Pyridazines" Vol. 28, R. N. Castle, Ed., Wiley Interscience, 1973, pp 597–601, and references cited therein; "Heterocyclic Compounds, The Pyrimidines" Vol. 16, D. J. Brown ed., Wiley Interscience 1985, pp 299–325; E. Schipper, and A. R. Day J. Am. Chem. Soc. (1952) 74, 350; "Comprehensive Heterocyclic Chemistry," Vol. 5, A. R. Katritsky and C. W. Rees Eds., Pergamon Press 1984; pp 567–597 and 631–656 and references cited therein].

SCHEME 4

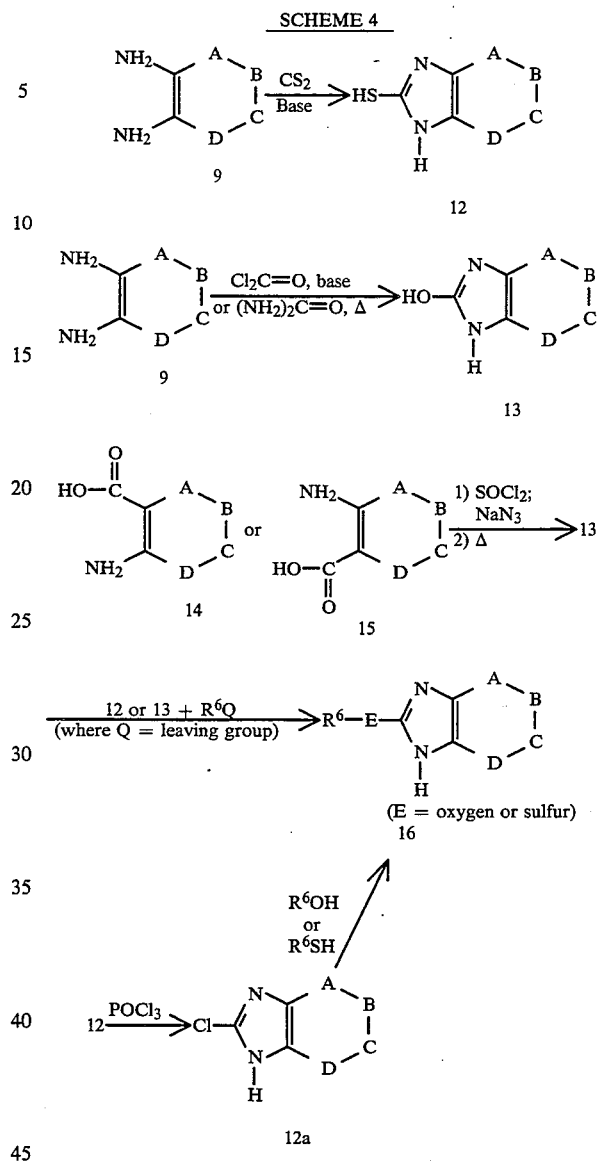

In cases wherein heterocycles of type (10) or (16) are not easily prepared from their corresponding diamines, or when these diamines cannot be prepared then alternative routes, involving fusion of the six member heterocycle onto an appropriately substituted imidazole, are used. Two of these routes are illustrated in Scheme 5. For example, imidazo[4,5-d][1,2,3]triazines (18) are preferentially prepared by treatment of amino carboxamido imidazoles (17) with sodium nitrite in aqueous acid. Precursor imidazoles (17) are prepared by degradation of an appropriately substituted xanthine or by condensation of an appropriate imidate ester with aminocyanoacetamide. Imidazo[4,5-b]pyridazines (20) can be prepared from imidazodicarboxylate esters (19) by treatment with hydrazine. Oxidation of (20) gives pyridazindiones (21). The oxygen(s) in (20) or (21) can be converted to other functionalities such as halides or thiones, which are themselves precursors for the synthesis of more elaborate systems ["Comprehensive Heterocyclic Chemistry," Vol. 5, A. R. Katritsky and C. W. Rees, eds., Pergamon Press 1984; pp 567–597 and 631–656 and references cited therein].

SCHEME 5
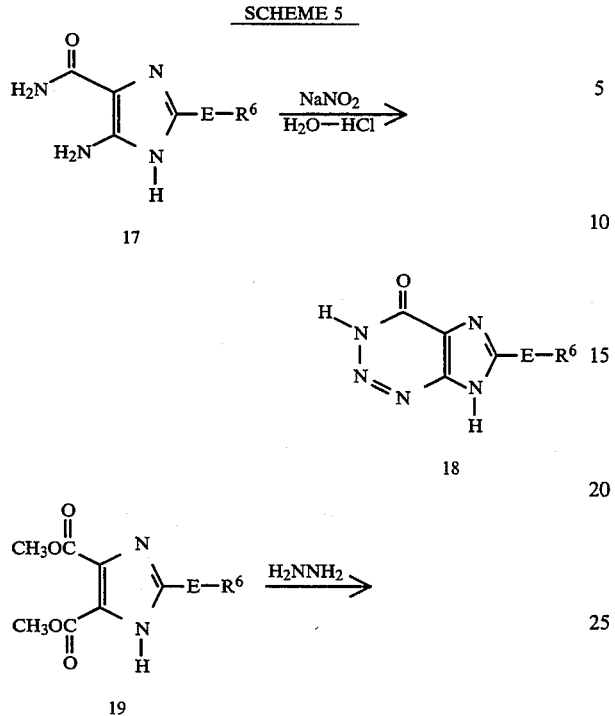
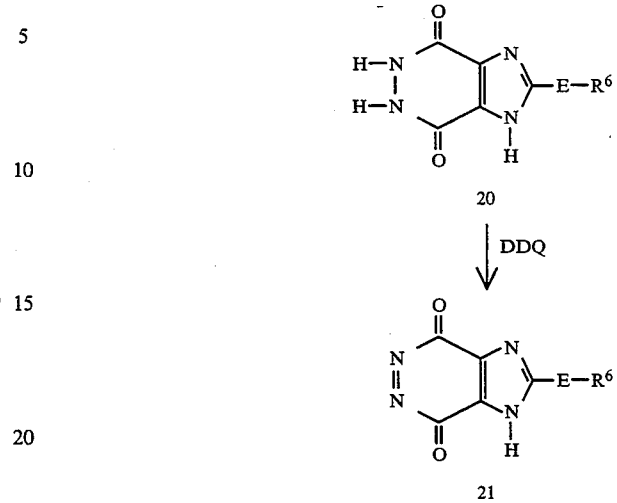
Moreover, as shown in Scheme 6, amino imidazole esters and amides are versatile intermediates for the preparation of purines. This scheme also illustrates the synthesis of the 6-membered heterocyclic ring after the alkylating agent (2) has been reacted with a suitably substituted imidazole to afford (22) or (24).
SCHEME 6
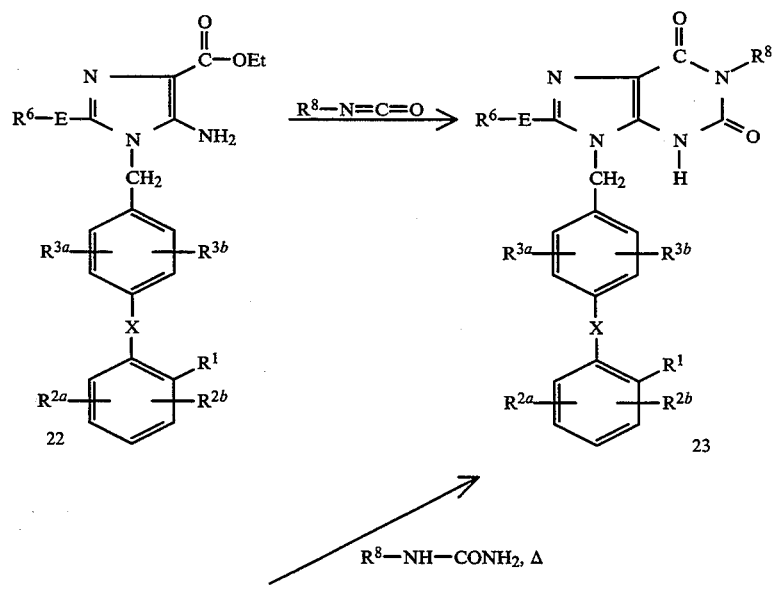

SCHEME 6

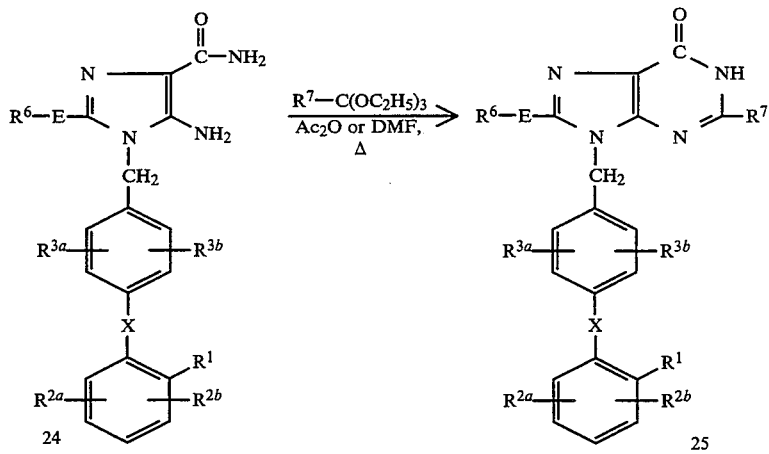

The preparation of reduced forms of heterocycles can be achieved by catalytic reduction, or by synthesis from a suitable imidazole precursor. For example, histidine and derivatives thereof react with formaldehyde to afford partially saturated imidazo(4,5-c)pyridines [cf. Neuberger, A. Biochem. J., (1944), 58,309].

Halogenation of the imidazo[4,5-b]pyridine ring at the 6-position can be accomplished using $Br_2$, or N-bromosuccinimide. Halogenation of the 7-position can be accomplished by reaction of the corresponding imidazopyridine-4-oxide (prepared by reaction of the imidazopyridine with peracids such as m-chloroperbenzoic acid) with $POCl_3$. When the 7-position is substituted with other than hydrogen, halogenation at the 5-position of the 4(N)-oxide precursor occurs upon treatment with $POCl_3$. Chlorides may be substisuted by bromides or iodides by treatment with either HBr or HI, respectively, in a solvent such as HOAc.

2-Alkyl-imidazo[4,5-b]pyridines can be substituted at the 5, 6, or 7 positions by displacement of a halogen at that position by nucleophiles such as cyanide, amines, copper alkoxides, trialkylphosphites, and thiolates. Also, substitution of the halogens, in particular bromides or iodides, can be accomplished by reaction with a coupling partner such as alkylzinc or arylzinc halides, or monoalkylarylphosphonites in the presence of an appropriate metal catalyst such as nickle, palladium, ruthenium, or platinum. In cases where the reaction is sluggish or complicated due to an acidic proton, the imidazopyridine may be protected at the 1, 3, or 4 positions by benzyl or other arylmethyl groups.

Compounds of formula I where $R^1$ is

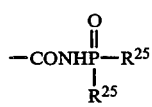

may be prepared from the corresponding carboxylic acid derivatives (I) as outlined in Scheme 7. The carboxylic acid (I), obtained as described in Scheme 1, can be converted into the corresponding amide by treatment with carbonyldiimidazole and then with ammonia. The resulting amide then can be treated with sodium hydride or n-butyllithium in THF at $-20°$ C. followed by an appropriately substituted phosphonyl or phosphinyl halide to form the desired compounds (26).

SCHEME 7

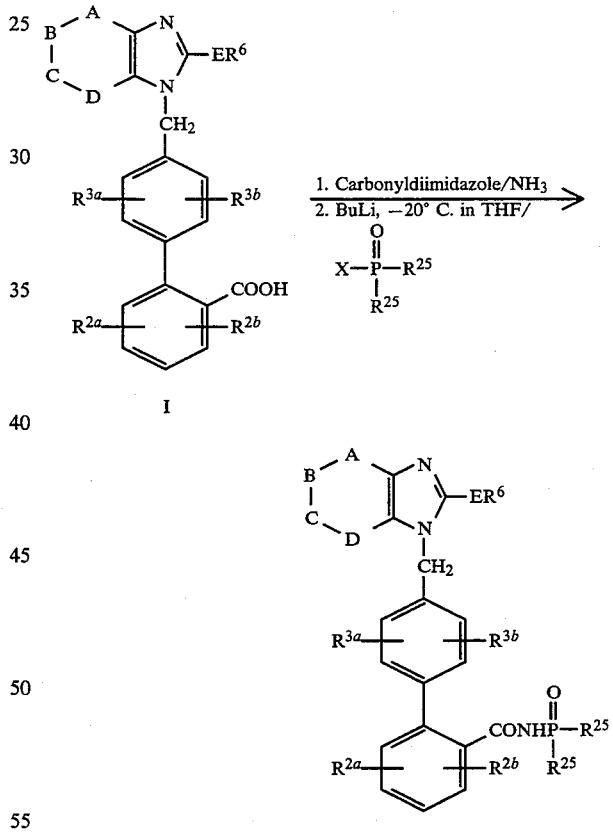

The biaryl sulfonamides (32) and (37), precursors for the alkylating agent 33, can be prepared from appropriate aryl-organotin precursors using palladium(O) catalyzed cross-coupling reactions [J. K. Stille, Pure Appl. Chem., 57, 1771 (1985); T. R. Baiely, Tetra Lett., 27, 4407 (1986); D. A. Widdowson and Y. Z. Zhang, Tetrahedron, 42, 2111 (1986)], as outlined in Schemes 8 and 9. The organotin compound (29) [S. M. Moerlein, J. Organometallic Chem., 319, 29 (1987)], obtained from the aromatic precursors (27 or 28), may be coupled with aryl sulfonamide (31) using $Pd(PPh_3)_4$ or $(PPh_3)_2PdCl_2$ as catalysts to give biaryl sulfonamide 32. Similarly, the biphenylmethyl bromide (33) may be alternatively prepared from the appropriate organotin precursor (36) using the Pd(O) catalyzed cross-coupling reaction as outlined in Scheme 9.

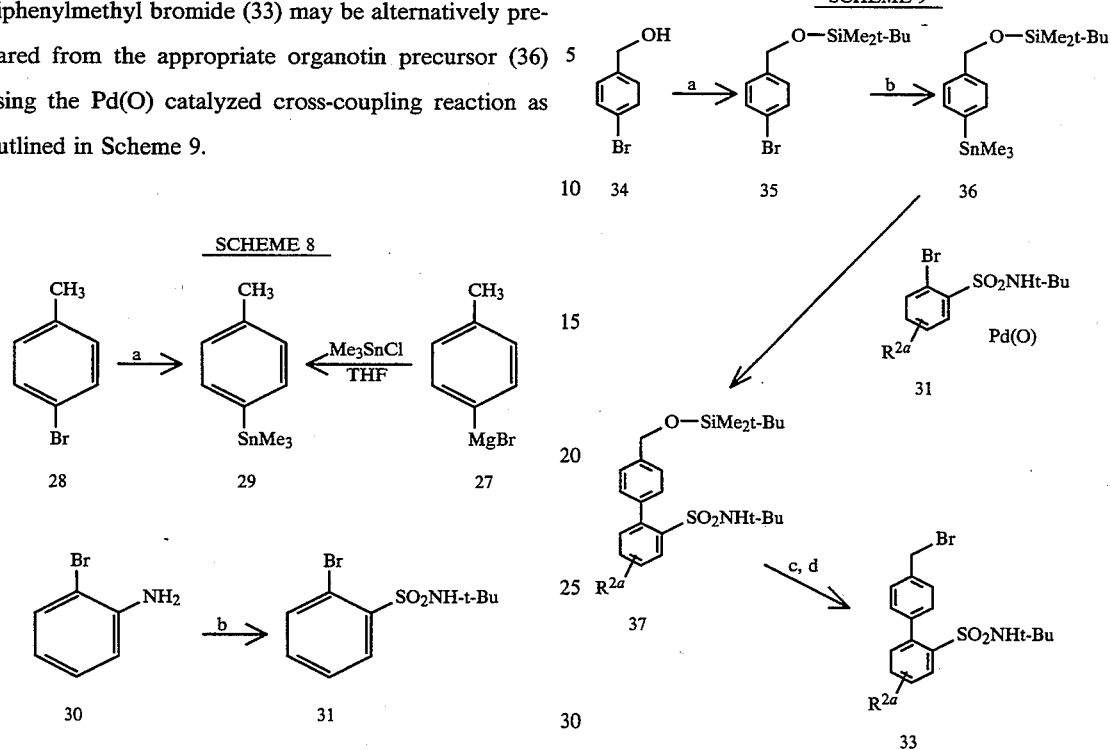

a. t-BuMe₂Si—Cl/Imidazole, DMF
b. t-BuLi, −78° C., Me₃SnCl
c. Tetrabutylammonium fluoride
d. CBr₄/Ph₃P.

Compounds of formula I where $R^1$ is —SO₂N-HSO₂$R^{23}$ may be prepared from the key sulfonamide intermediate 38 as outlined in Scheme 10. The intermediate 38 may be prepared by the alkylation of appropriate heterocycles with the alkylating agent 33 as outlined in Scheme 1. Treatment of 38 with trifluoroacetic acid followed by acylation of the resulting sulfonamide 39 with appropriate sulfonyl chlorides may produce the desired compounds (40).

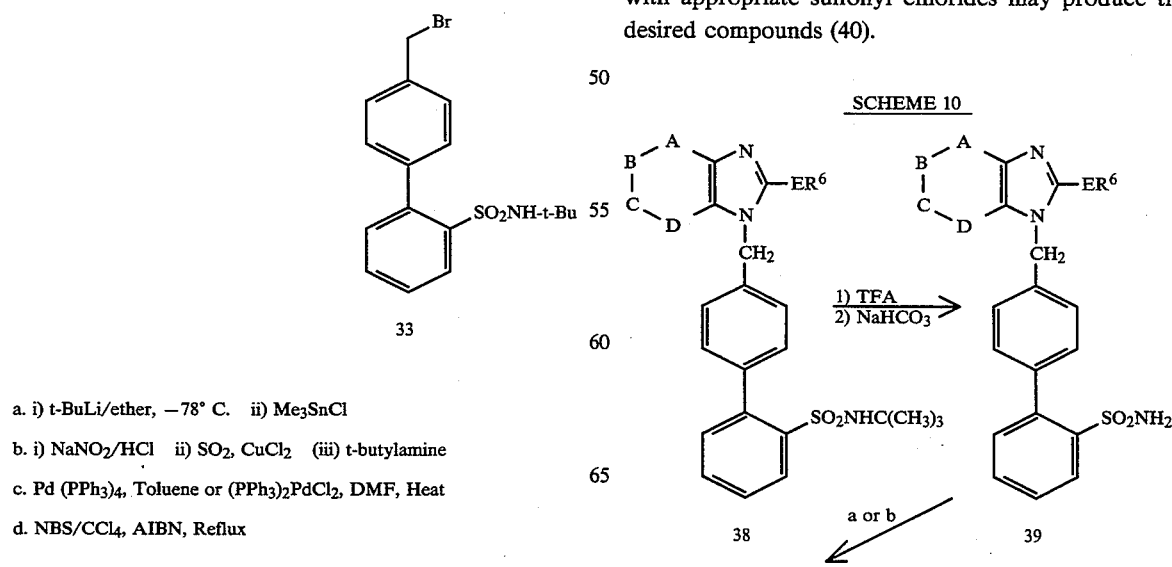

a. i) t-BuLi/ether, −78° C.  ii) Me₃SnCl
b. i) NaNO₂/HCl  ii) SO₂, CuCl₂  (iii) t-butylamine
c. Pd (PPh₃)₄, Toluene or (PPh₃)₂PdCl₂, DMF, Heat
d. NBS/CCl₄, AIBN, Reflux -continued
SCHEME 10

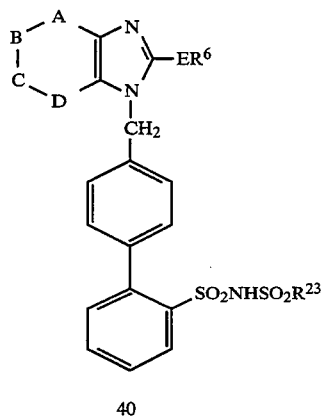

40 a. i) NaH/THF or DMF  (ii) R²³SO₂Cl
b. R²³SO₂Cl, DBU, THF

Compounds of Formula (I) wherein R¹ is —SO₂NH-CO₂R²⁴ may be prepared by reacting an appropriate chloroformate with the sulfonamide (29) in pyridine or in the presence of DBU in THF to afford the desired compound (41), as outlined in Scheme 11.

SCHEME 11

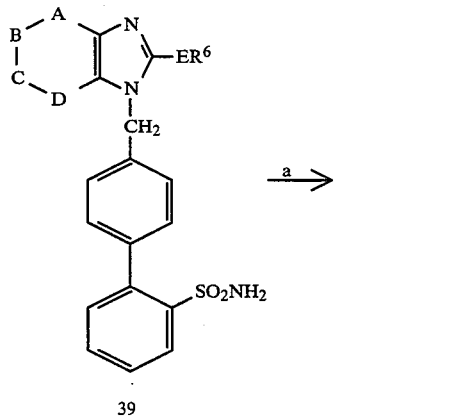

39

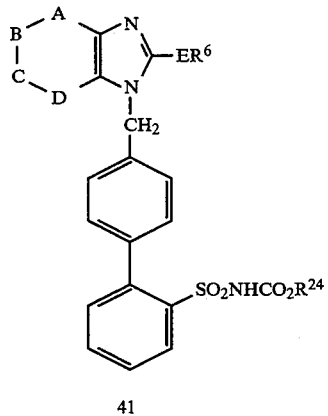

41 a. R²⁴OCCl, pyridine or DBU, THF

Compounds of Formula (I) wherein R¹ is

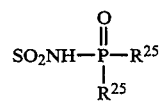

may be prepared by treating sulfonamide (39) with n-butyllithium in THF followed by the treatment of the resulting anion with an appropriately substituted phosphonyl or phosphinyl halide to form the desired compounds (42). (Scheme 12)

SCHEME 12

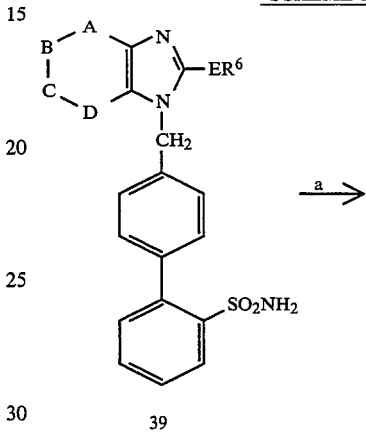

39

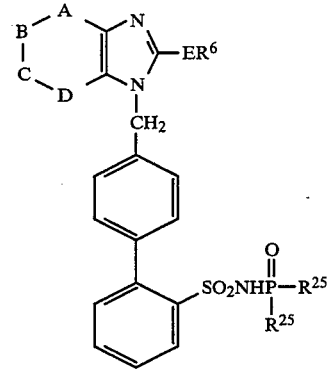

42

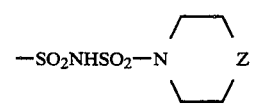

Compounds of Formula (I) wherein R¹ is SO₂N-HSO₂N(R²⁵)₂ or $$-SO_2NHSO_2-N\diagup\diagdown Z$$

may also be prepared from sulfonamide (39) as outlined in Scheme 13. Treatment of 39 with n-butyllithium in THF at −25° C. and then with an appropriate sulfamoyl halide may produce the desired product (43) or (44).

SCHEME 13

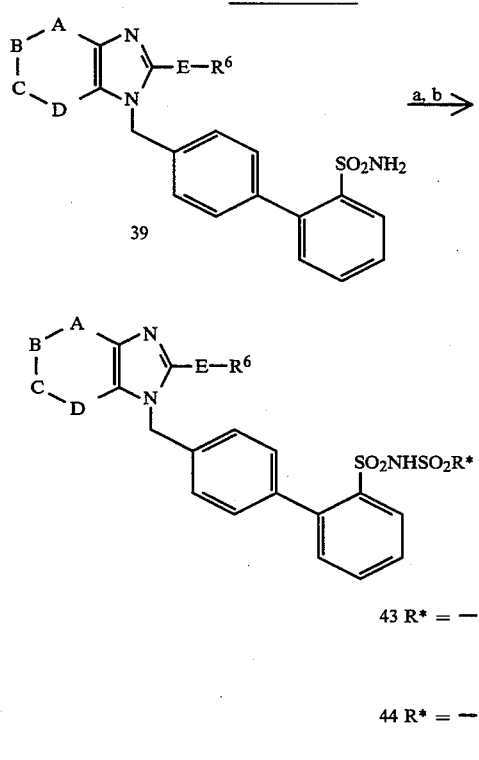

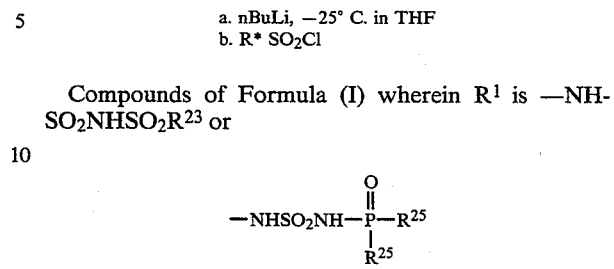

a. nBuLi, −25° C. in THF
b. R* SO₂Cl

Compounds of Formula (I) wherein R¹ is —NH-SO₂NHSO₂R²³ or $$-NHSO_2NH-\overset{\overset{O}{\|}}{\underset{R^{25}}{P}}-R^{25}$$

may be prepared from arylamine (46) as outlined in Scheme 14. The arylamine (46) obtained from the corresponding nitro compound 45 can be treated with t-butylsulfamoyl chloride to afford the protected amino sulfonamide (47). The amino sulfonamide (48) obtained after removal of the t-butyl protecting group may then be reacted with an appropriate acylating agent in the presence of a base such as pyridine or DBU in an organic solvent such as THF or DMF to form the desired products (49a) or (49b).

Compounds of the Formula (I) wherein R¹ is —NH-SO₂R²³ may be prepared by the reaction of an appropriate sulfonyl halide (R²³SO₂Cl) or sulfonyl imidazole derivative with the aryl amine 46 in the presence of an appropriate base such as pyridine, triethylamine or DBU.

SCHEME 14

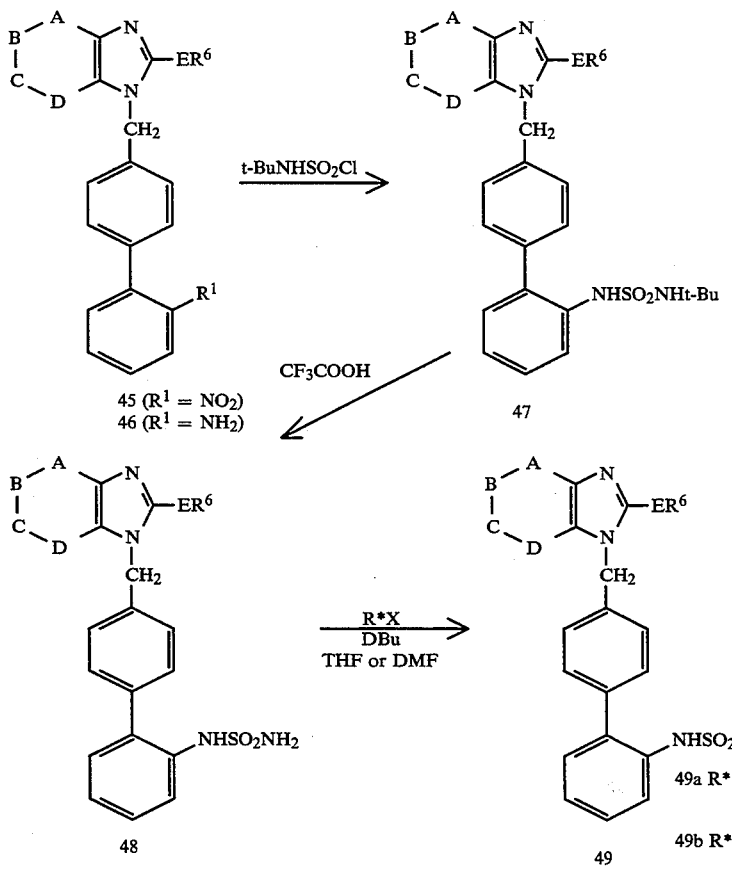

Compounds of Formula (I) and the benzyl halides of the formula (55) wherein $R^1$ is 1,2,3,5-oxathiadiazole-2-oxide may be prepared from the corresponding cyano derivative (50) or cyano precursor (7b) as outlined in Schemes 15 and 16, respectively utilizing procedures described in U.S. Pat. No. 4,910,019. The cyano derivatives (50), obtained as described in Scheme 1, can be converted into the corresponding amidoxime (51) by treatment with hydroxylamine hydrochloride and sodium methoxide in an organic solvent, such as methanol or DMSO. The amidoxime (51) then can be treated with base and thionyl chloride in an aprotic solvent to form the desired 1,2,3,5-oxathiadiazole-2-oxide (52). Similarly, the oxathiadiazole-2,2-dioxide 52a can be prepared by treatment of amidoxime 51 with a base and sulfuryl chloride. As shown in Scheme 16, the cyano precursor (7b) may be converted into the desired 1,2,3,5-oxathiadiazole (54) which is then protected with the trityl group prior to the formation of the desired benzyl halide (55). The protecting group is removed subsequent to the alkylation of heterocycle (1) to give the desired product (52).

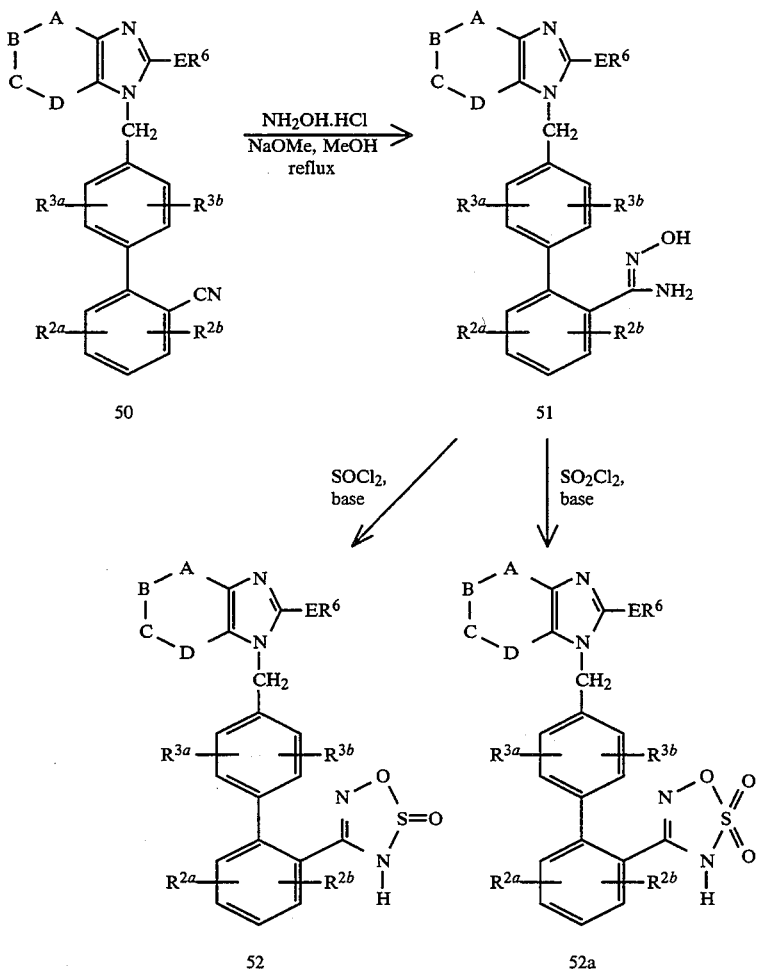

SCHEME 15

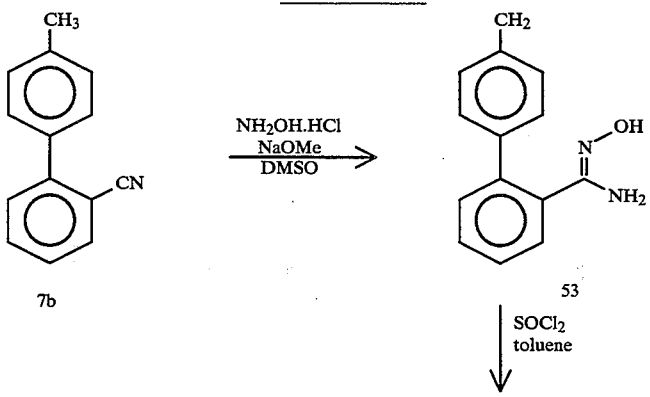

SCHEME 16

SCHEME 16

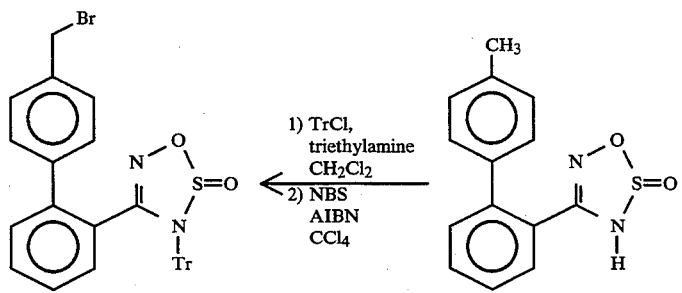

Compounds of Formula (I) and the benzyl halides of the formula (2) wherein $R^1$ is 1,2,3,5-thiatriazole-1-oxide may be prepared from the corresponding carboxamido precursor or cyano precursor as outlined in Scheme 17 and 18, respectively. Intermediates (57) and (61) can be treated with $SOCl_2$ (see procedures in: *Ber. Deutsch. Chem. Ges.* 1971, 104 pp 639) to give intermediates, (58) and (62), each of which may be protected with a trityl group, and subsequently brominated to give (60) and (64), respectively. Alternatively, (60) and (64) may be prepared as shown in Scheme 19 and 20. Treatment of (65) with $SOCl_2$ (see procedures in: *Ber. Deutsch. Chem. Ges.* 1971, 104 pp 639) provides (66), which under mild hydrolytic conditions provides (58). The conversion of (58) to (60) is as described for Scheme 17. Alkylation of the trityl protected analog (67) by treatment with a base such as NaH and an alkyl halide would provide (59), which then may be converted to (64) as previously described.

Compounds of Formula (I) wherein $R^1$ is 1,2,3,5-thiatriazole-1-oxide may also be prepared as exemplified in Example 14.

SCHEME 17

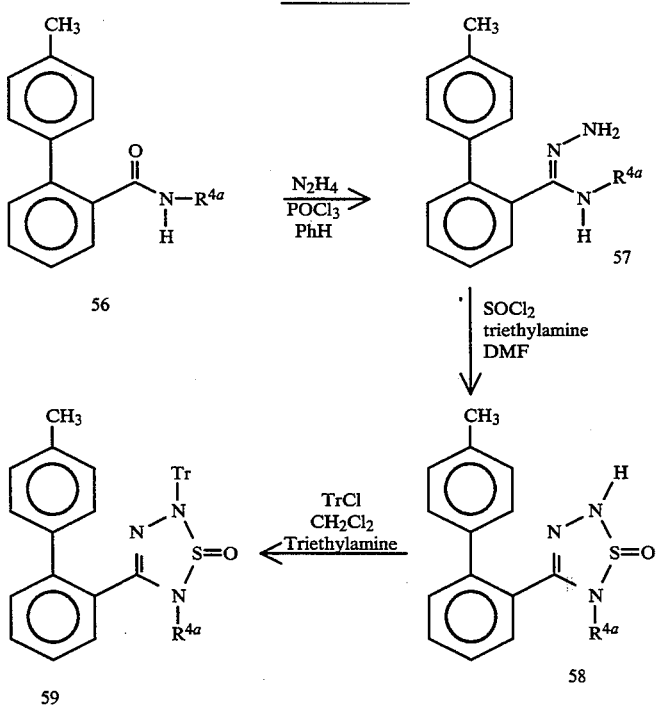

-continued
SCHEME 17
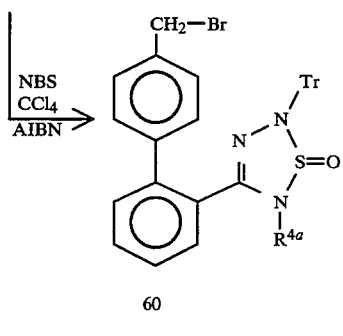
SCHEME 18
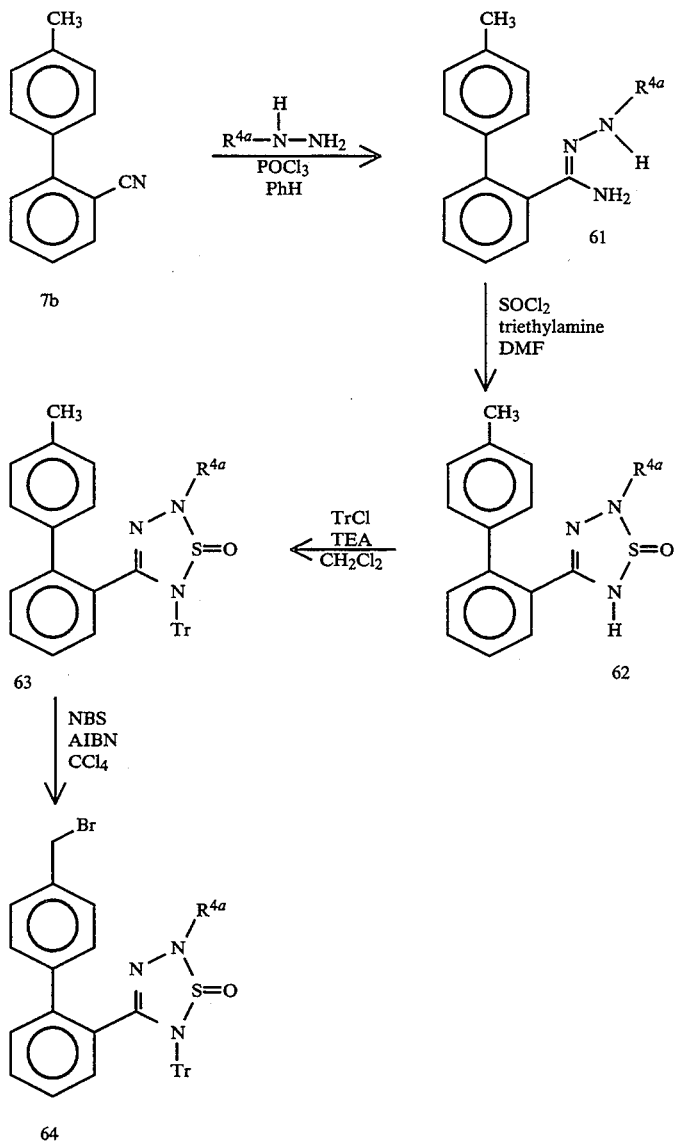

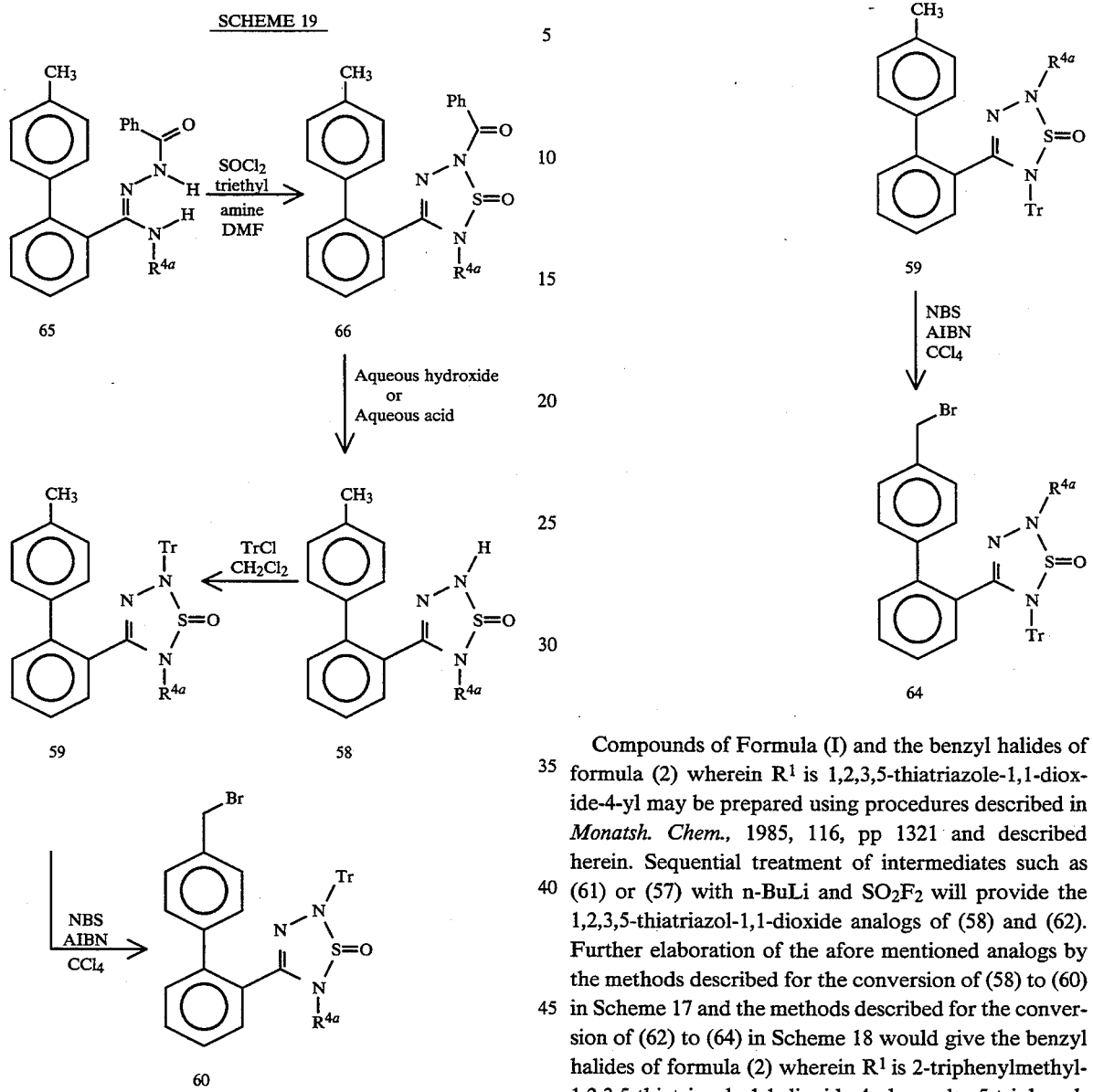

Compounds of Formula (I) and the benzyl halides of formula (2) wherein $R^1$ is 1,2,3,5-thiatriazole-1,1-dioxide-4-yl may be prepared using procedures described in *Monatsh. Chem.*, 1985, 116, pp 1321 and described herein. Sequential treatment of intermediates such as (61) or (57) with n-BuLi and $SO_2F_2$ will provide the 1,2,3,5-thiatriazol-1,1-dioxide analogs of (58) and (62). Further elaboration of the afore mentioned analogs by the methods described for the conversion of (58) to (60) in Scheme 17 and the methods described for the conversion of (62) to (64) in Scheme 18 would give the benzyl halides of formula (2) wherein $R^1$ is 2-triphenylmethyl-1,2,3,5-thiatriazole-1,1-dioxide-4-yl and 5-triphenyl-methyl-1,2,3,5-thiatriazole-1,1-dioxide-4-yl, respectively.

Compound of Formula (I) wherein $R^1$ is 3-oxo-1,2,4-thiadiazolidine-1,1-dioxide may be prepared from the nitro derivative (7c) as outlined in Scheme 21. The amino compound 6.8. obtained from 7c may be reacted with t-butyl sulfamoylchloride to form the intermediate 69, which then can be alkylated with an appropriate bromoacetic acid derivative to give 70. Treatment of 70 with trifluoroacetic acid followed by the treatment with an appropriate base such as sodium or potassium alkoxide may produce the desired compound 71, which can be elaborated further to give the key alkylating agent 73 as outline in the scheme. Alkylation of an appropriate heterocyclic compound with 73 may then furnish the desired antagonist.

SCHEME 21

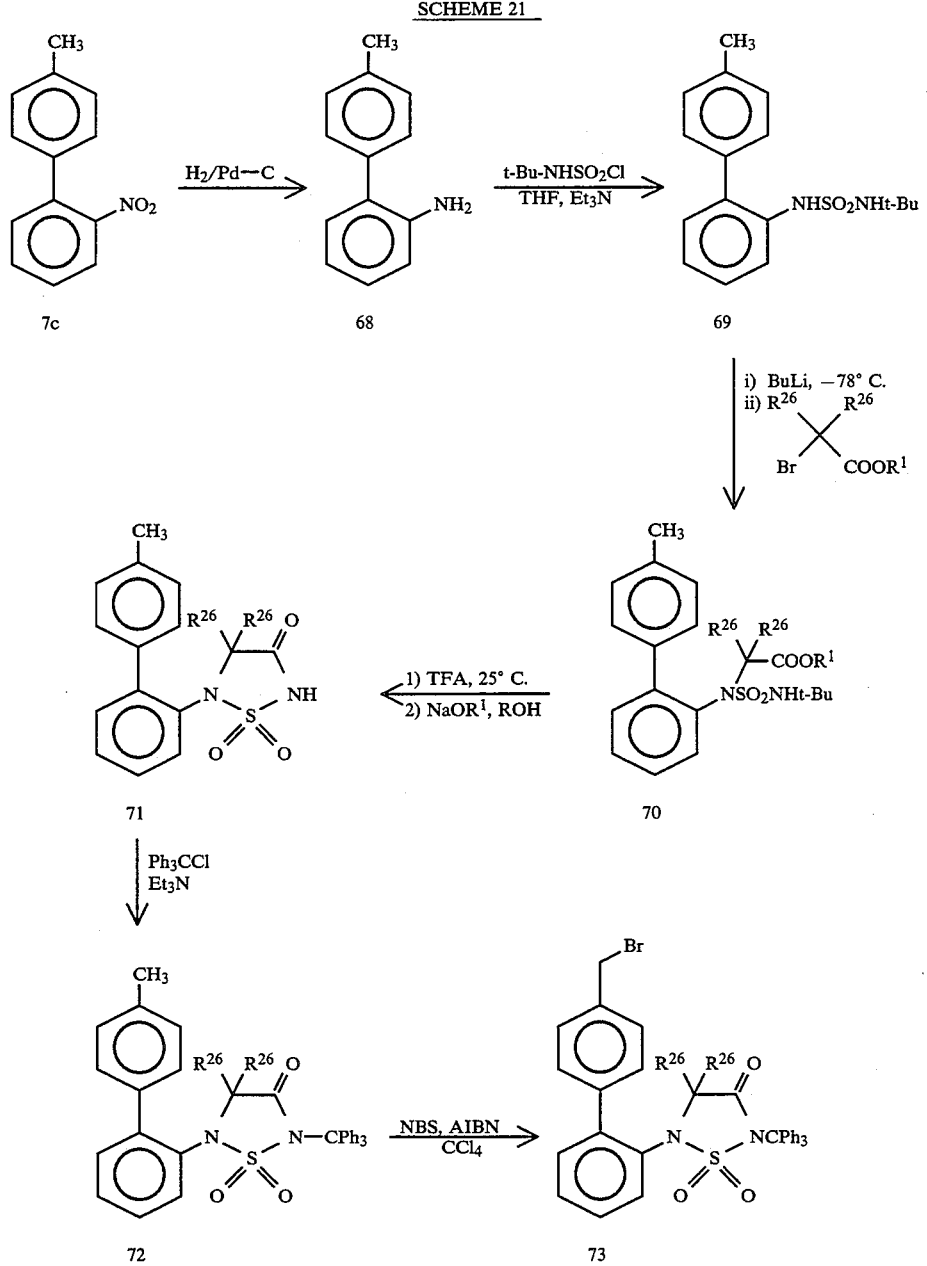

Compound of Formula (I) wherein $R^1$ is 5-aminosulfonyl-1,2,4-oxadiazole may be prepared using the bromomethyl biphenyl derivative 77 and an appropriate heterocyclic compound. The synthesis of 77 can be accomplished as outlined in Scheme 22. The amidoxime 53 may be reacted with S-methylisothiourea to form the 5-amino-1,2,4-oxadiazole 74, which can be then treated with an appropriate sulfonylchloride to give the corresponding 5-aminosulfonyl-1,2,4-oxadiazole 75. The appropriately protected derivative 76 then can be brominated to form the desired alkylating agent 77.

SCHEME 22

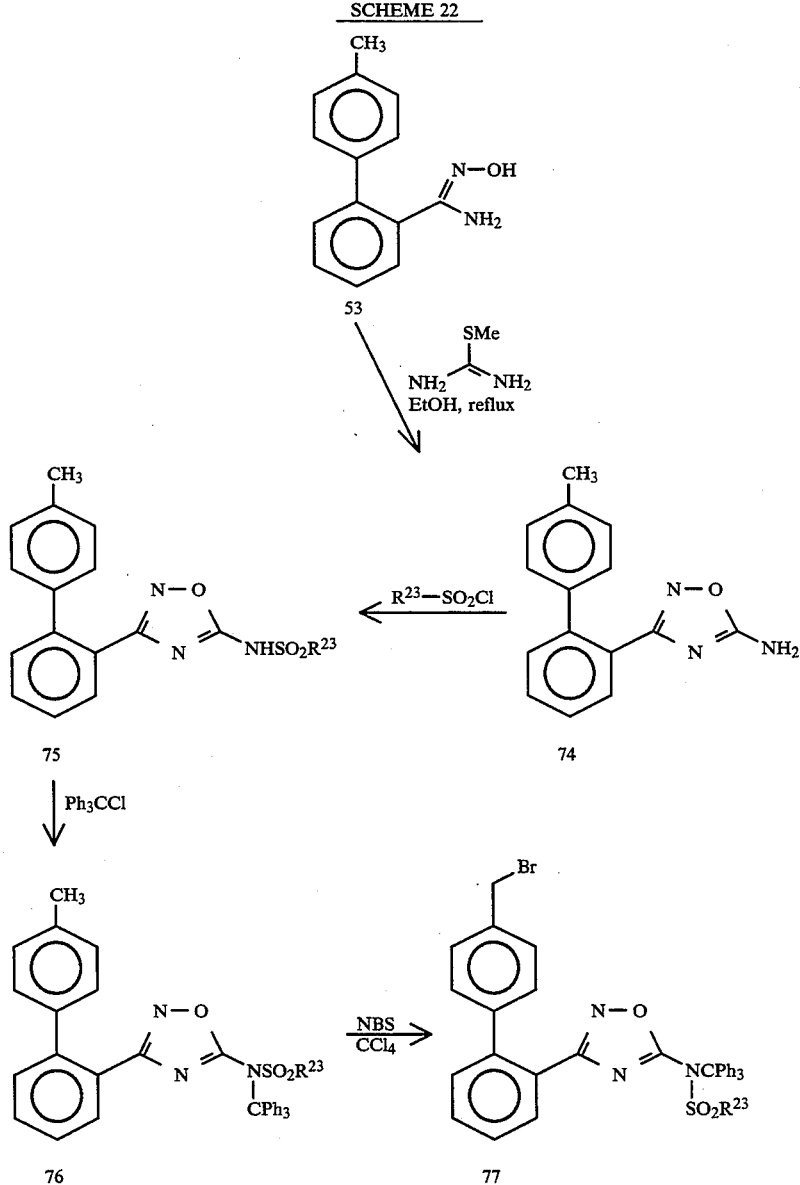

Compounds of Formula (I) wherein $R^1$ is 3-aminosulfonyl-1,2,4-oxadiazole can be prepared starting from the carboxylate derivative (7a) as outlined in Scheme 23. The ester derivative 78 obtained from 7a is treated with N-hydroxy guanidine sulfate in the presence of an alkoxide base to form the 3-amino-1,2,4-oxadiazole derivative 79, which may be reacted with an appropriate sulfonyl chloride to give the 3-aminosulfonyl-1,2,4-oxadiazole compound 80. The compound 81 can be prepared from 80 as outlined in Scheme 23.

SCHEME 23

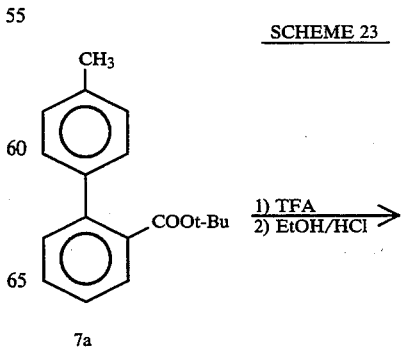

-continued
SCHEME 23

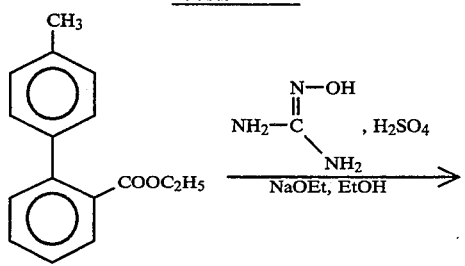

78

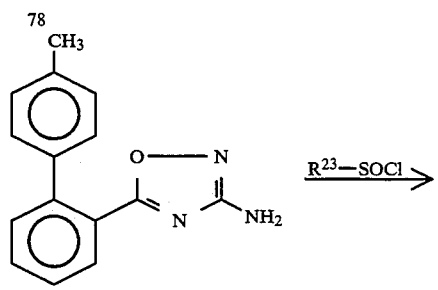

79

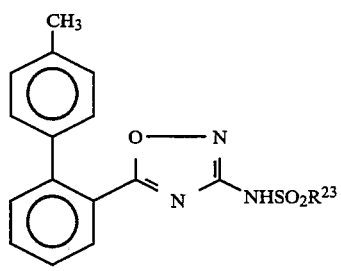

80

1) Ph$_3$CCl/W$_3$M
2) NBS/CCl$_4$

-continued
SCHEME 23

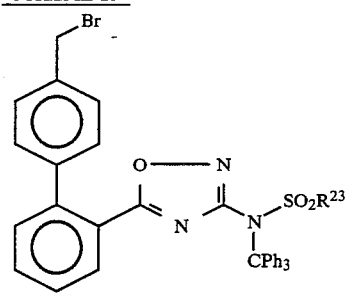

81

Compounds of Formula (I) and the benzyl halides of formula (2) wherein R$^1$ is 1,2,3-oxathiazin-4(3H)-one-2,2-dioxide-6-yl may be prepared as outlined in Scheme 24. As shown and according to procedures in *Angew. Chem. Int. Edn.*, (1973), 12, pp 869, the beta-ketoester (82) is treated with fluorosulphonyl isocyanate, heated to extrude CO$_2$ and iso-butene, then treated with base such as KOH to form the oxathiazolinone dioxide intermediate (83). Treatment of (83) with triphenylmethyl chloride and triethylamine in CH$_2$Cl$_2$ gives (84) which in turn is converted to benzyl halide (85) by treatment with N-bromosuccinimide, AIBN, in CCl$_4$ at reflux.

SCHEME 24

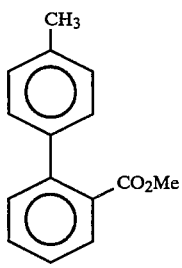

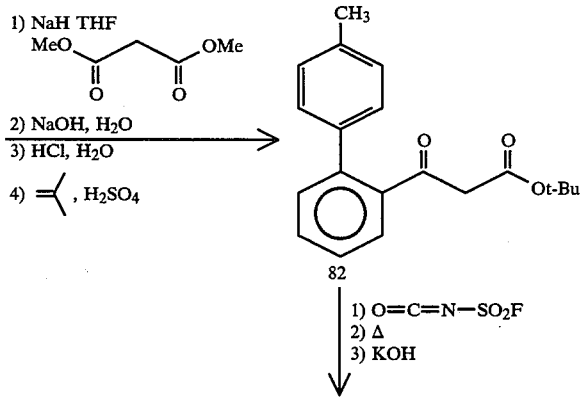

82

1) O=C=N—SO$_2$F
2) Δ
3) KOH

SCHEME 24

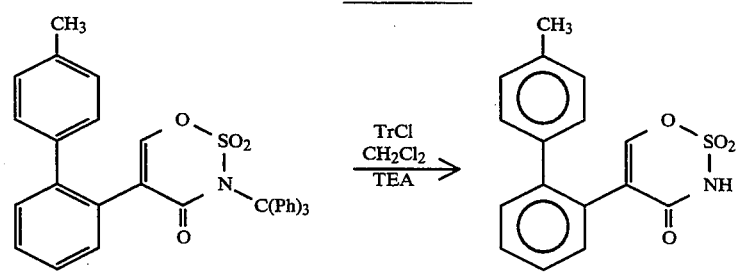

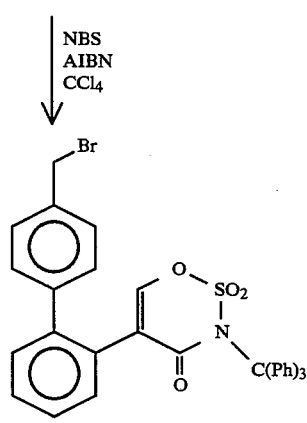

Compounds of Formula (I) wherein R¹ is oxamic acid may be prepared utilizing procedures described in J. Med. Chem., 1981, 24, pp 742–748 and as outlined in Scheme 25. The amine (46) is reacted with ethyl oxalyl chloride in the presence of a base such as pyridine or triethylamine and a solvent such as $CH_2Cl_2$ to form the intermediate oxalyl ester which is subsequently saponified with hydroxide to form oxamic acid (86).

SCHEME 25

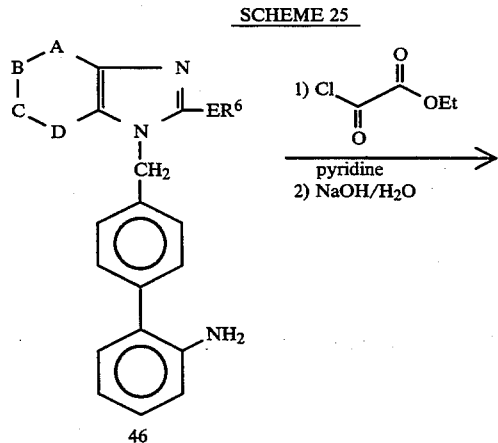

-continued
SCHEME 25

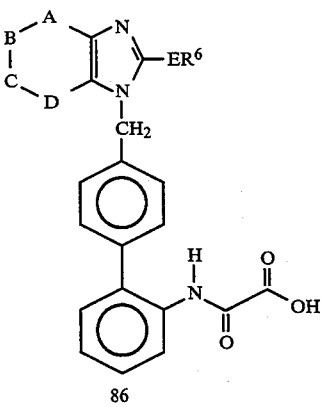

Compounds of Formula (I) wherein R¹ is —$SO_2NR^{24}OR^{24}$ may be prepared as outlined in Scheme 26. The key intermediate 89 is prepared by the reaction of an appropriate heterocyclic compound (1), preferably as an alkali metal salt, with the alkylating agent 87 (prepared from 36). The compound 91, prepared from the sulfonyl chloride 90 and O-t-butylhydroxylamine, is then reacted with 89 in the presence of a Pd(O) catalyst to give 92. Removal of the t-butyl protecting group produces the desired N-hydroxy sulfonamide 93.

SCHEME 26

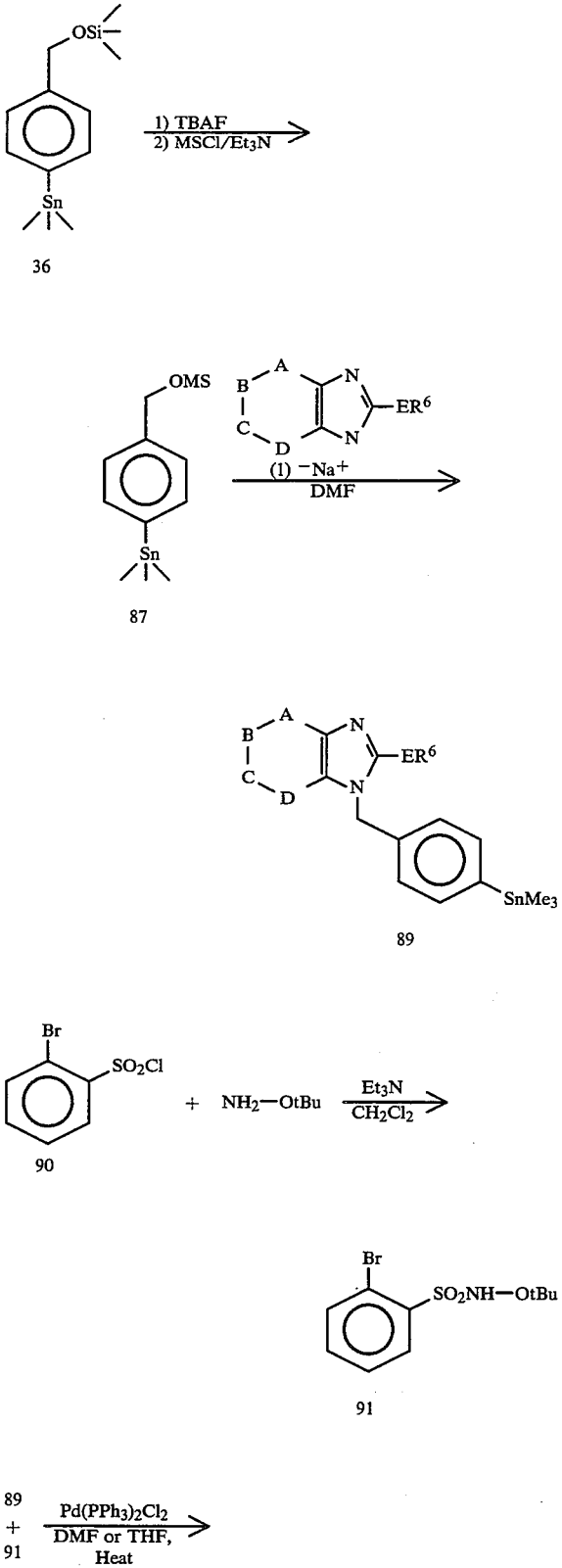

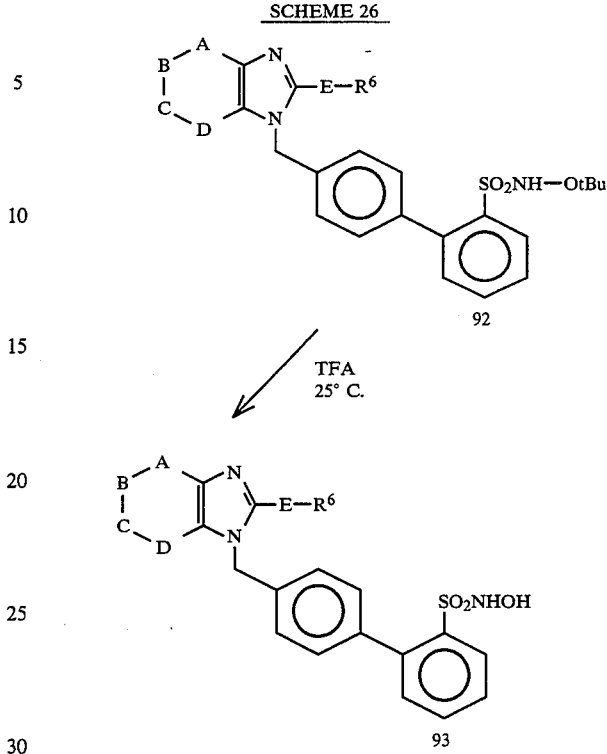

The general procedure used to prepare many of the 5'-substituted derivatives is illustrated in Scheme 27. Commercially available 4-substituted benzenesulfonyl chlorides ($R^{2a}$=i-Pr, n-BuO, tert-amyl, Me, Et, n-Pt, t-Bu) are reacted with t-BuNH$_2$ to provide derivative 94 in good yield. Dianion generation, with 2.5 equivalents of n-BuLi, followed by quench with triisopropyl borate provides boric acid derivative 95 in excellent yield, after hydrolysis with dilute acid. Palladium catalyzed coupling of boric acid 95 and 4-bromobenzyl derivative 96 in the presence of 1.25N NaOH, EtOH and toluene, affords an excellent yield of the desired coupled product. The 4-bromobenzyl derivative 94 can be prepared by alkylating the substituted imidazo[4,5-b]pyridine with the appropriately substituted benzylbromide. Deprotection using TFA is followed by coupling by reaction with an appropriate alkyl chloroformate in pyridine in the presence of DMAP.

When the desired 4-substituted benzenesulfonyl chlorides are not commercially available, the necessary t-butylsulfonamide 94 derivatives can be prepared using procedures outlined in Scheme 28 (A–F).

Antagonists with 5'-alkoxy methyl derivatives are best prepared using the protocol outlined in Scheme 29. Palladium catalyzed coupling of 5-methyl-2-t-butylsulfonamide phenylboric acid with methyl 4-iodobenzoate affords derivative 107. Benzylic bromination, utilizing NBS, provides the desired bromomethyl derivative that is then reacted with the appropriate sodium alkoxide to afford derivative 109. Reduction of the ester to the primary alcohol with LAH is followed by conversion to the bromomethyl derivative (111) with PBr$_3$. Alkylation of the sodium salt of the heterocycle with 16 in DMF provides derivative 98 ($R^{2a}$=CH$_2$OR). The antagonist is completed as previously illustrated in Scheme 27.

Scheme 30 illustrates how new sulfonylcarbamates (113) can be prepared from a previously prepared sulfonylcarbamate (112). Simple heating of the substrate in neat alcohol for several hours provides clean conversion to the new sulfonylcarbamate.
SCHEME 27
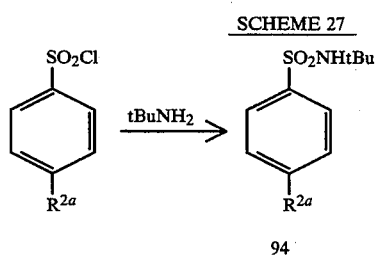
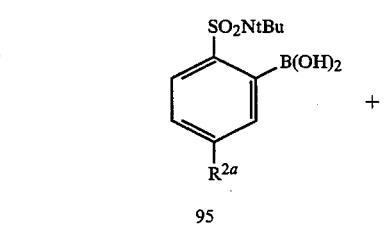
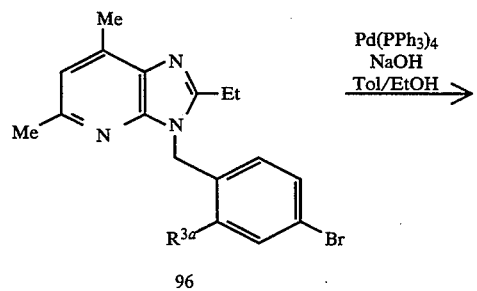
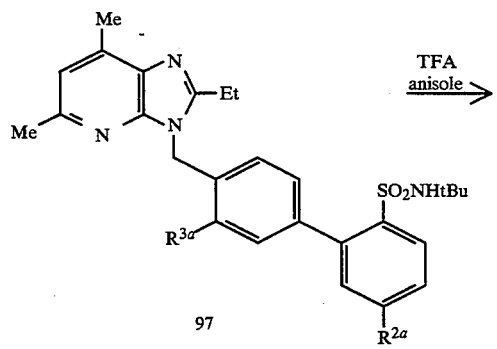
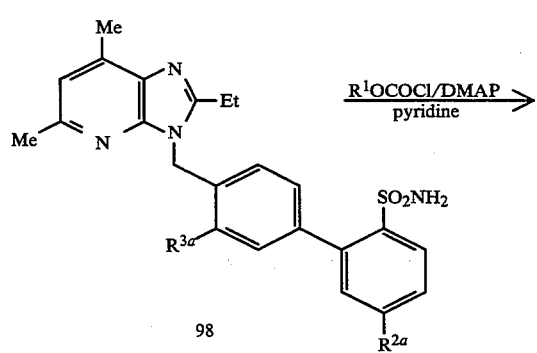
SCHEME 27 -continued
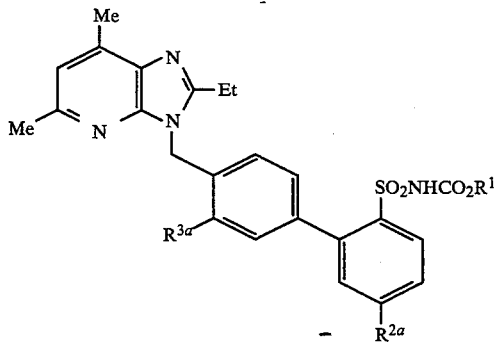
SCHEME 28
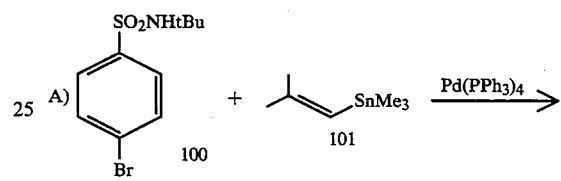
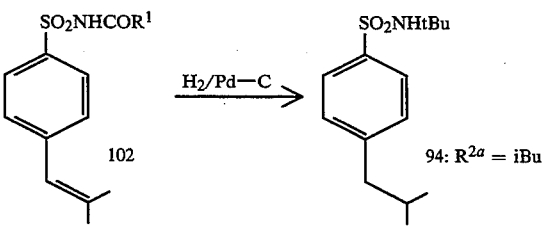
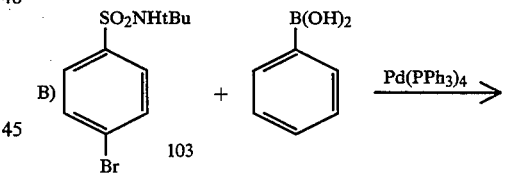
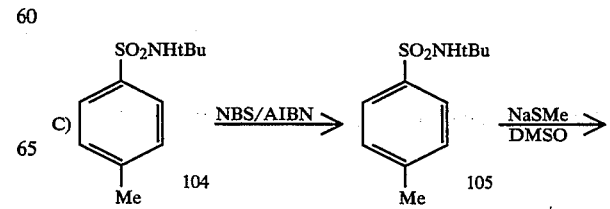

-continued
SCHEME 28
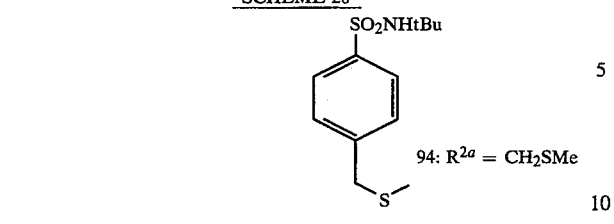
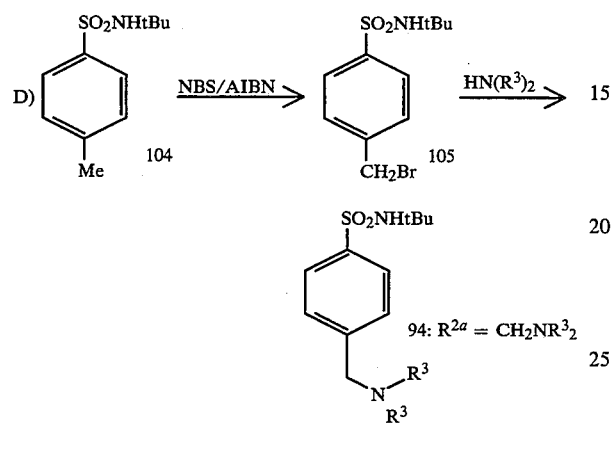
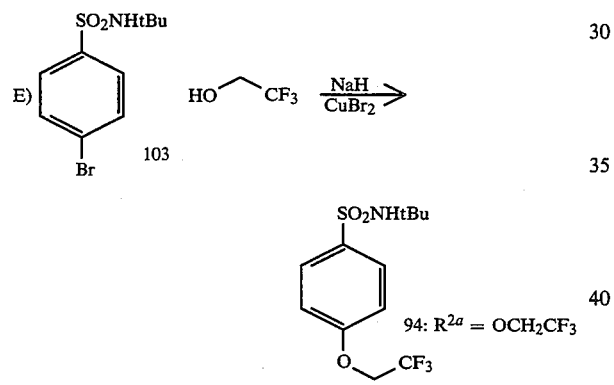
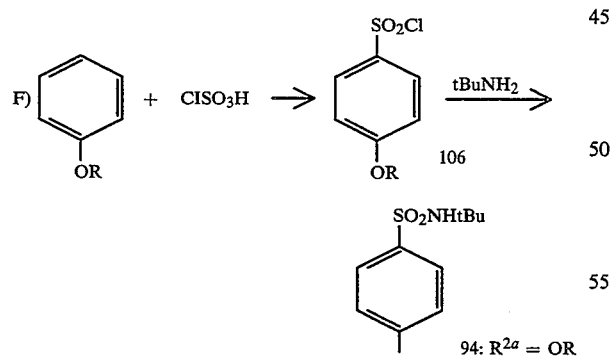
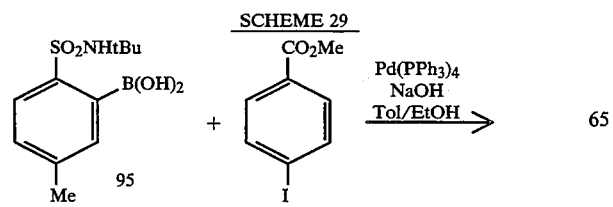
-continued
SCHEME 29
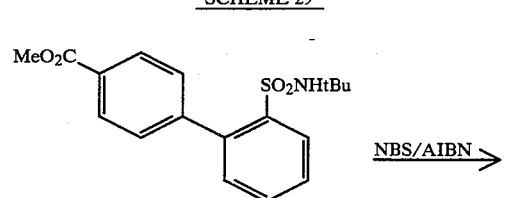
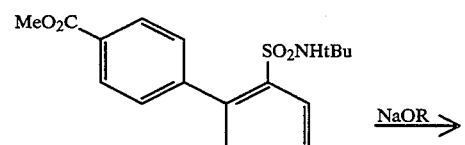
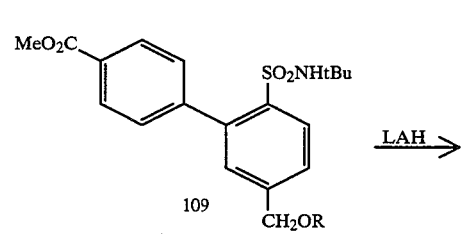
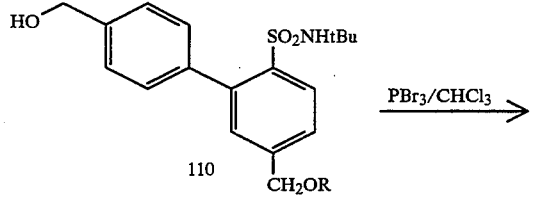
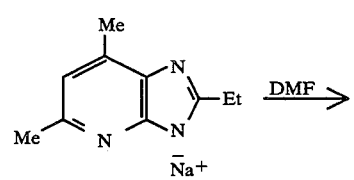

SCHEME 30

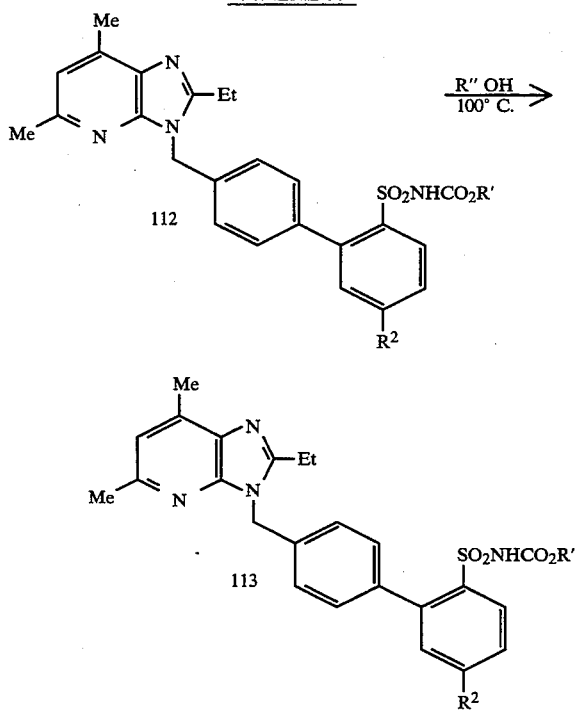

Methods for preparing 6-substituted imidazopyridines are shown in Schemes 31 and 32. Nitration of an appropriately substituted 2-amino-3-nitropyridine using nitric acid in sulfuric acid gives 2-amino-3,5-dinitropyridine derivative 116. Treatment of 116 under reducing conditions such as $H_2$ with a catalyst such as Raney-Nickel or palladium on carbon gives the 2,3,5-triaminopyridine derivative 117. Triamine 117 may be handled as the salt of an inorganic acid such as HCl or $H_3PO_4$. The salt is preferrentially prepared by the addition of the inorganic acid directly to the reduction step reaction mixture immediately after removal of the catalyst by vacuum filtration. Heating the triamine with 2 equivalents of an appropriate carboxylic acid in polyphosphoric acid provides 6-amidoimidazopyridine 118. Alternatively, this transformation may be performed using 2 equivalents of an appropriate acid chloride followed by heating in an aprotic solvent. The amide 118 may be hydrolysed to amine 119 by treatment with acid in water or alcoholic solvent. Treatment of amine 119 with an acid chloride provides analogs of 118, wherein $R^{23}$ is not equal to $R^6$. Additionally, treatment of amine 119 with an isocyanate or an alkylcarbamyl chloride in the presence of base affords the urea analog 120.

Imidazopyridines bearing an alkoxy group at the 2-position may be prepared as shown in Scheme 32. Heating triaminopyridine analogs 117 in the presence of excess tetraalkyl orthocarbonate affords imidazopyridines bearing a 6-carbamate substituent 121. Imidazopyridine analogs bearing 6-amino 122, 6-amido 123, and 6-ureido 124 substituents are readily available from 121 by using the transformations outlined in the scheme.

SCHEME 31

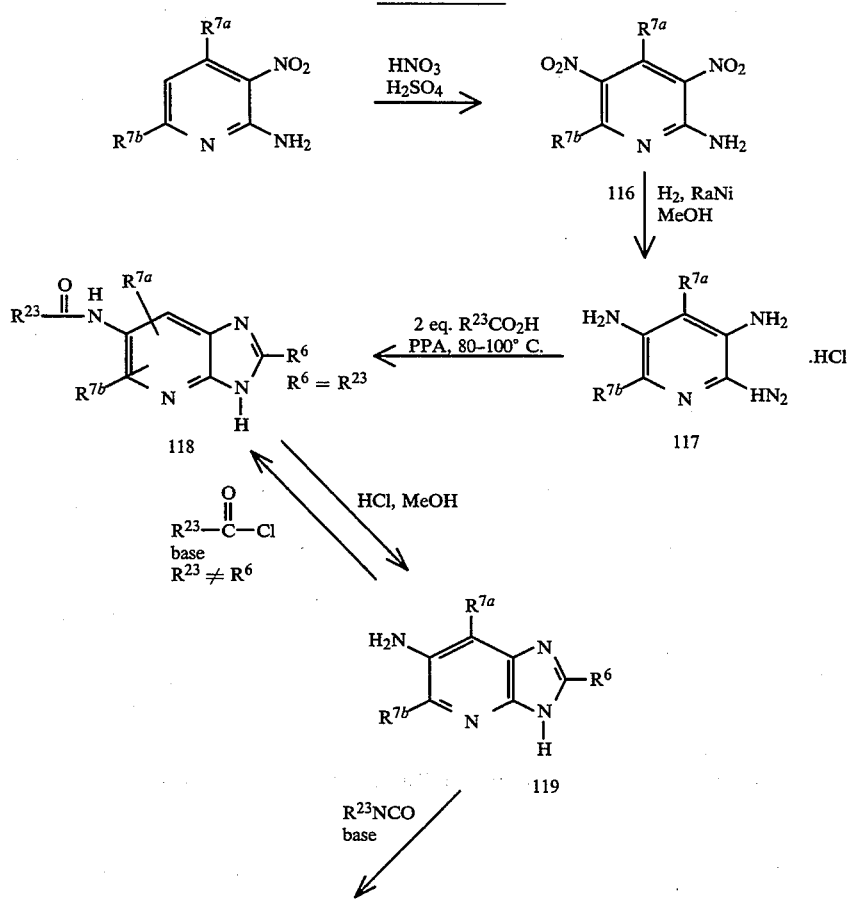

SCHEME 31

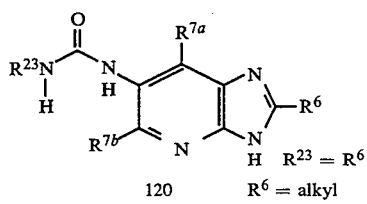

SCHEME 32

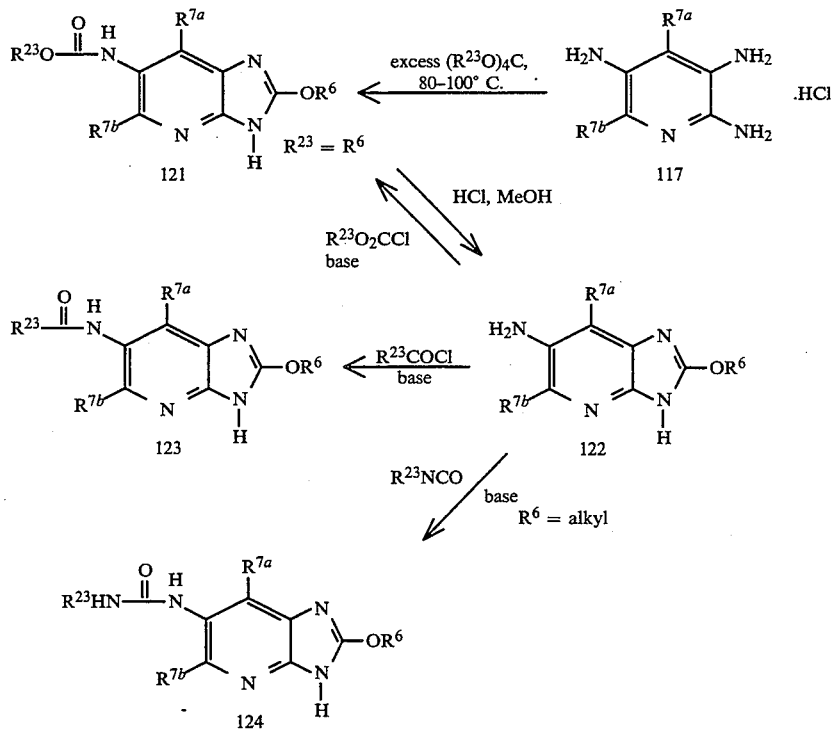

The imidazopyridines shown in Schemes 31 and 32 can be further elaborated to obtain AII antagonists of Type I by the methods outlined in Schemes 1, 10, and 11, and Scheme 27.

6-amino-7-carboxy-imidazopyridines 131 and 132 can be prepared as shown in Scheme 33. The aminopyridine intermediate 126 is obtained from 125 by careful displacement of the 2-chloro substituent. Nitration of 126 followed by reaction with KCN provides 128, which is reduced to the triamine 129. Treatment of 129 with 2 equivalents of an acid chloride followed by heating in xylenes provides imidazopyridine 130. Heterocycle 130 can be alkylated as in Scheme 1 followed by hydrolysis of the cyano group to afford a carboxy intermediate which can be protected and further elaborated as in Schemes 10, 11, and 27. Alternatively 131 or 132 can be alkylated and further elaborated as described in Schemes 1, 10, 11, and 27.

Antagonists containing a 6-amido group and a substituent in the central phenyl ring of the biphenyl moiety can best be constructed using the procedure outlined in Scheme 34. Alkylation of the imidazo[4,5-b]pyridine 118 with an appropriately substituted 4-bromobenzyl bromide affords the benzyl bromide derivative 134. Acid hydrolysis of the amido group provides the amine 135, which can be acylated with a variety of acid chlorides, such as benzoyl chloride, to provide the amido derivative 136. Palladium catalyzed coupling of 136 with boric acid 95, as described in Scheme 27, provides the t-butylsufonamide derivative 137. Deprotection of the sulfonamide followed by acylation of 138 completes the synthesis of analogs bearing a 6-amido group on the imidazopyridine and a substitutent on the central phenyl as well as the lower phenyl ring.

SCHEME 33
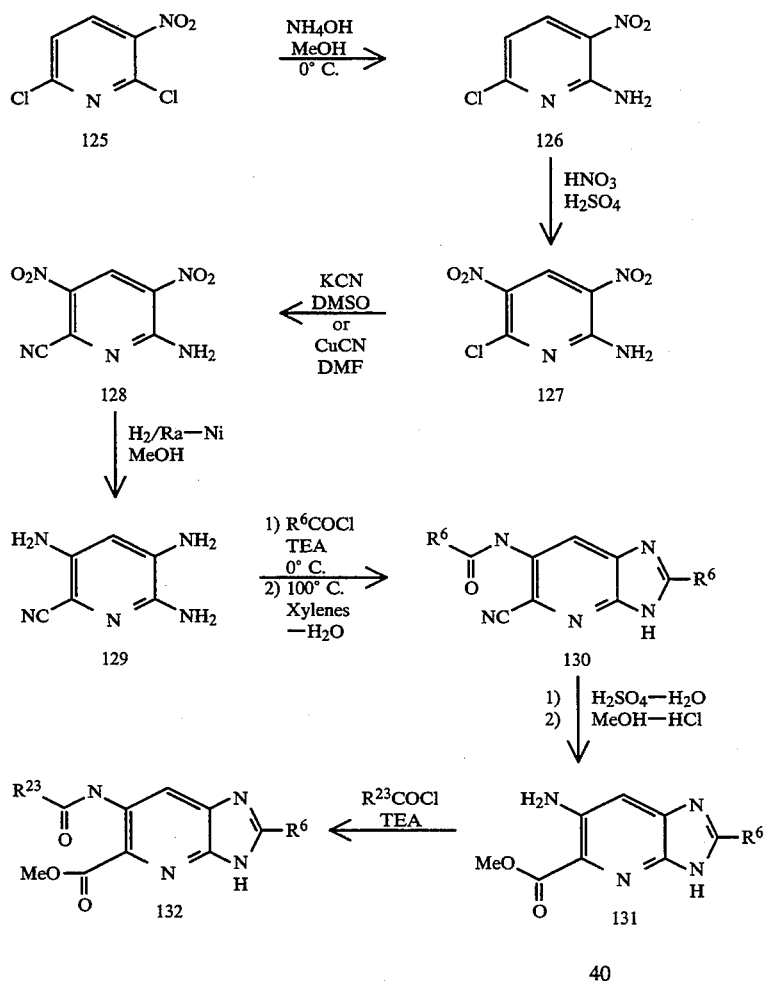
SCHEME 34
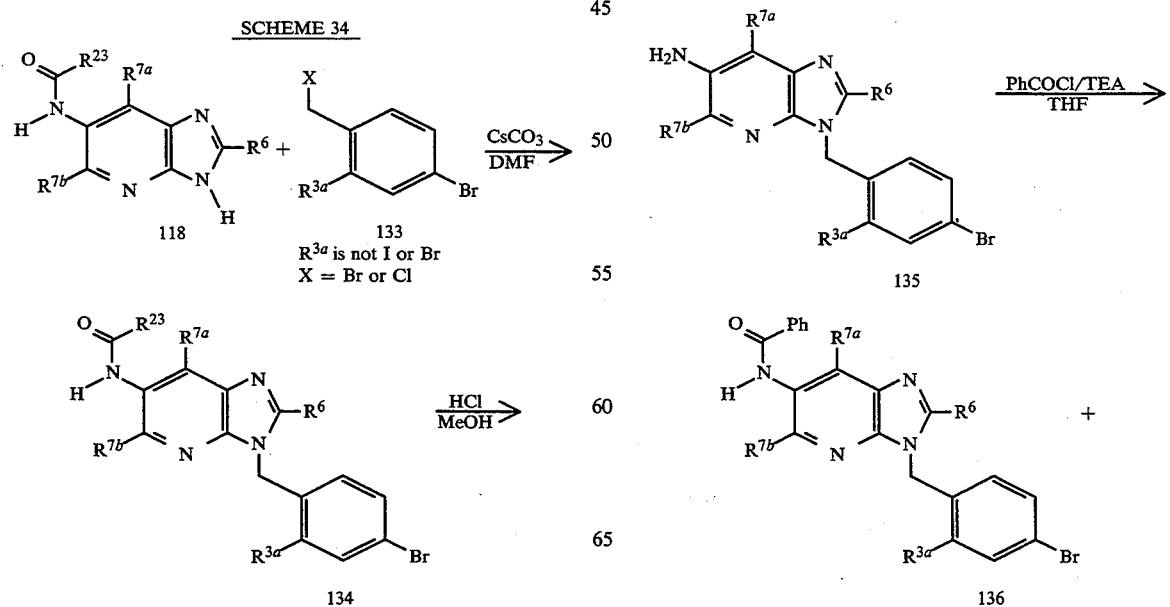

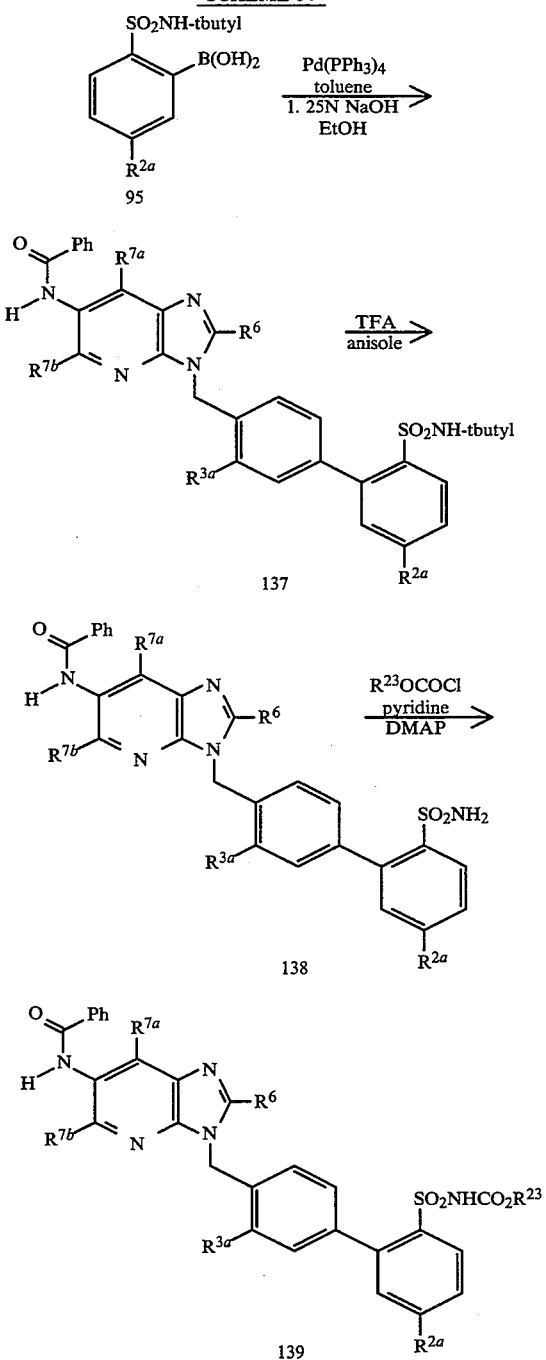

It will be appreciated by those skilled in the art that functional group transformations can be conducted on aryl and heterocyclic rings to afford desired analogs. For example, esters may be converted to amides by heating them with amines and an amide nitrogen if present in the heterocycle may be alkylated using bases such as sodium hydride in DMF with the appropriate alkyl halide. Functional group protection throughout these syntheses will be chosen to be compatible with subsequent reaction conditions. Ultimately such protecting groups will be removed to generate the desired optimally active compounds of Formula I. For example, $R^1$ as carboxyl is often protected as its t-butyl ester which in the last step is removed by treatment with trifluoroacetic acid.

The compounds of this invention form salts with various inorganic and organic acids and bases which are also within the scope of the invention. Such salts include ammonium salts, alkali metal salts like sodium and potassium salts, alkaline earth metal salts like the calcium and magnesium salts, salts with organic bases; e.g., dicyclohexylamine salts, N-methyl-D-glucamine, salts with amino acids like arginine, lysine, and the like. Also, salts with organic and inorganic acids may be prepared; e.g., HCl, HBr, $H_2SO_4$, $H_3PO_4$, methane-sulfonic, toluene-sulfonic, maleic, fumaric, camphorsulfonic. The non-toxic, physiologically, acceptable salts are preferred, although other salts are also useful; e.g., in isolating or purifying the product.

The salts can be formed by conventional means such as by reacting the free acid or free base forms of the product with one or more equivalents of the appropriate base or acid in a solvent or medium in which the salt is insoluble, or in a solvent such as water which is then removed in vacuo or by freeze-drying or by exchanging the cations of an existing salt for another cation on a suitable ion exchange resin.

Angiotensin II (AII) is a powerful arterial vasoconstrictor, and it exerts its action by interacting with specific receptors present on cell membranes. The compounds described in the present invention act as competitive antagonists of AII at the receptors. In order to identify AII antagonists and determine their efficacy in vitro, the following ligand-receptor binding assays were used along with binding assays reported in the literature (R. S. Chang et al, *Biochem. Biophys. Res. Commun.* 1990, 171, 813.)

Receptor binding assay using rabbit aortae membrane preparation:

Three frozen rabbit aortae (obtained from Pel-Freeze Biologicals) were suspended in 5 mM Tris-0.25M Sucrose, pH 7.4 buffer (50 ml) homogenized, and then centrifuged. The mixture was filtered through a cheesecloth and the supernatant was centrifuged for 30 minutes at 20,000 rpm at 4° C. The pellet thus obtained was resuspended in 30 ml of 50 mM Tris-5 mM $MgCl_2$ buffer containing 0.2% Bovine Serum Albumin and 0.2 mg/ml Bacitration and the suspension was used for 100 assay tubes. Samples tested for screening were done in duplicate. To the membrane preparation (0.25 ml) there was added $^{125}$I-Sar$^1$Ile$^8$-angiotensin II [obtained from New England Nuclear] (10 ul; 20,000 cpm) with or without the test sample and the mixture was incubated at 37° C. for 90 minutes. The mixture was then diluted with ice-cold 50 mM Tris-0.9% NaCl, pH 7.4 (4 ml) and filtered through a glass fiber filter (GF/B Whatman 2.4" diameter). The filter was soaked in scintillation cocktail (10 ml) and counted for radioactivity using Packard 2660 Tricarb liquid scintillation counter. The inhibitory concentration ($IC_{50}$) of potential AII antagonist which gives 50% displacement of the total specifically bound $^{125}$I-Sar$^1$Ile$^8$-angiotensin II was presented as a measure of the efficacy of such compounds as AII antagonists.

Receptor assay using Bovine adrenal cortex preparation

Bovine adrenal cortex was selected as the source of AII receptor. Weighed tissue (0.1 g is needed for 100 assay tubes) was suspended in Tris.HCl (50 mM), pH 7.7 buffer and homogenized. The homogenate was centrifuged at 20,000 rpm for 15 minutes. Supernatant was discarded and pellets resuspended in buffer [$Na_2HPO_4$ (10 mM)-NaCl (120 mM)-disodium EDTA (5 mM)

containing phenylmethane sulfonyl fluoride (PMSF) (0.1 mM)]. (For screening of compounds, generally duplicates of tubes are used). To the membrane preparation (0.5 ml) there was added 3H-angiotensin II (50 mM) (10 ul) with or without the test sample and the mixture was incubated at 37° C. for 1 hour. The mixture was then diluted with Tris buffer (4 ml) and filtered through a glass fiber filter (GF/B Whatman 2.4" diameter). The filter was soaked in scintillation cocktail (10 ml) and counted for radioactivity using Packard 2660 Tricarb liquid scintillation counter. The inhibitory concentration ($IC_{50}$) of potential AII antagonist which gives 50% displacement of the total specifically bound $^3$H-angiotensin II was presented as a measure of the efficacy of such compounds as AII antagonists.

Using the methodology described above, representative compounds of this invention were evaluated and were found to exhibit an activity of at least $IC_{50} < 50$ μM, thereby demonstrating and confirming the utility of the compounds of the invention as effective A II antagonists.

The antihypertensive effects of the compounds described in the present invention may be evaluated using the methodology described below:

Male Charles River Sprague-Dawley rats (300–375 gm) were anesthetized with methohexital (Brevital; 50 mg/kg i.p.) and the trachea was cannulated with PE 205 tubing. A stainless steel pithing rod (1.5 mm thick, 150 mm long) was inserted into the orbit of the right eye and down the spinal column. The rats were immediately placed on a Harvard Rodent Ventilator (rate—60 strokes per minute, volume—1.1 cc per 100 grams body weight). The right carotid artery was ligated, both left and right vagal nerves were cut, and the left carotid artery was cannulated with PE 50 tubing for drug administration, and body temperature was maintained at 37° C. by a thermostatically controlled heating pad which received input from a rectal temperature probe. Atropine (1 mg/kg i.v.) was then administered, and 15 minutes later propranolol (1 mg/kg i.v.). Thirty minutes later antagonists of formula I were administered intravenously or orally. Angiotensin II was then typically given at 5, 10, 15, 30, 45 and 60 minute intervals and every half-hour thereafter for as long as the test compound showed activity. The change in the mean arterial blood pressure was recorded for each angiotensin II challenge and the precent inhibition of the angiotensin II response was calculated.

The compounds of the invention are useful in treating hypertension. They are also of value in the management of acute and chronic congestive heart failure. These compounds may also be expected to be useful in the treatment of secondary hyperaldosteronism, primary and secondary pulmonary hyperaldosteronism, primary and secondary pulmonary hypertension, renal failure such as diabetic nephropathy, glomerulonephritis, scleroderma, glomerular sclerosis, proteinuria of primary renal disease, end stage renal disease, renal transplant therapy, and the like, renal vascular hypertension, left ventricular dysfunction, diabetic retinopathy and in the management of vascular disorders such as migraine, Raynaud's disease, luminal hyperclasia, and to minimize the atherosclerotic process. The application of the compounds of this invention for these and similar disorders will be apparent to those skilled in the art.

The compounds of this invention are also useful to treat elevated intraocular pressure and to enhance retinal blood flow and can be administered to patients in need of such treatment with typical pharmaceutical formulations such as tablets, capsules, injectables and the like as well as topical ocular formulations in the form of solutions, ointments, inserts, gels, and the like. Pharmaceutical formulations prepared to treat intraocular pressure would typically contain about 0.1% to 15% by weight, preferably 0.5% to 2% by weight, of a compound of this invention.

In the management of hypertension and the clinical conditions noted above, the compounds of this invention may be utilized in compositions such as tablets, capsules or elixirs for oral administration, suppositories for rectal administration, sterile solutions. Or suspensions for parenteral or intramuscular administration, and the like. The compounds of this invention can be administered to patients (animals and human) in need of such treatment in dosages that will provide optimal pharmaceutical efficacy. Although the dose will vary from patient to patient depending upon the nature and severity of disease, the patient's weight, special diets then being followed by a patient, concurrent medication, and other factors which those skilled in the art will recognize, the dosage range will generally be about 1 to 1000 mg. per patient per day which can be administered in single or multiple doses. Perferably, the dosage range will be about 2.5 to 250 mg. per patient per day; more preferably about 5 to 150 mg. per patient per day.

The compounds of this invention can also be administered in combination with other antihypertensives and/or diuretics and/or angiotensin converting enzyme inhibitors and/or calcium channel blockers. For example, the compounds of this invention can be given in combination with such compounds as amiloride, atenolol, bendroflumethiazide, chlorothalidone, chlorothiazide, clonidine, cryptenamine acetates and cryptenamine tannates, deserpidine, diazoxide, guanethidene sulfate, hydralazine hydrochloride, hydrochlorothiazide, metolazone, metoprolol tartate, methyclothiazide, methyldopa, methyldopate hydrochloride, minoxidil, pargyline hydrochloride, polythiazide, prazosin, propranolol, rauwolfia serpentina, rescinnamine, resetpine, sodium nitroprusside, spironolactone, timolol maleate, trichlormethiazide, trimethophan camsylate, benzthiazide, quinethazone, ticrynafan, triamterene, acetazolamide, aminophylline, cyclothiazide, ethacrynic acid, furosemide, merethoxylline procaine, sodium ethacrynate, captopril, delapril hydrochloride, enalapril, enalaprilat, fosinopril sodium, lisinopril, pentopril, quinapril hydrochloride, ramapril, teprotide, zofenopril calcium, diflusinal, diltiazem, felodipine, nicardipine, nifedipine, niludipine, nimodipine, nisoldipine, nitrendipine, and the like, as well as admixtures and combinations thereof.

Typically, the individual daily dosages for these combinations can range from about one-fifth of the minimally recommended clinical dosages to the maximum recommended levels for the entities when they are given singly.

To illustrate these combinations, one of the angiotensin II antagonists of this invention effective clinically in the 2.5-250 milligrams per day range can be effectively combined at levels at the 0.5-250 milligrams per day range with the following compounds at the indicated per day dose range: hydrochlorothiazide (15–200 mg) chlorothiazide (125–2000 mg), ethacrynic acid (15–200 mg), amiloride (5–20 mg), furosemide (5–80 mg), propranolol (20–480 mg), timolol maleate (5–60 mg.), methyldopa (65–2000 mg), felodipine (5–60 mg), nifedipine (5–60 mg), and nitrendipine (5–60 mg). In addition, triple drug combinations of hydrochlorothiazide (15-200 mg) plus amiloride (5-20 mg) plus angiotensin II antagonist of this invention (3-200 mg) or hydrochlorothiazide (15-200 mg) plus timolol maleate (5-60) plus an angiotensin II antagonist of this invention (0.5-250 mg) or hydrochlorothiazide (15-200 mg) and nifedipine (5-60 mg) plus an angiotensin II antagonist of this invention (0.5-250 mg) are effective combinations to control blood pressure in hypertensive patients. Naturally, these dose ranges can be adjusted on a unit basis as necessary to permit divided daily dosage and, as noted above, the dose will vary depending on the nature and severity of the disease, weight of patient, special diets and other factors.

Typically, these combinations can be formulated into pharmaceutical compositions as discussed below.

About 1 to 100 mg. of compound or mixture of compounds of Formula I or a physiologically acceptable salt is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

Illustrative of the adjuvants which can be incorporated in tablets, capsules and the like are the following: a binder such as gum tragacanth, acacia, corn starch or gelatin; an excipient such as microcrystalline cellulose; a disintegrating agent such as corn starch, pregelatinized starch, alginic acid and the like; a lubricant such as magnesium stearate; a sweetening agent such as sucrose, lactose or saccharin; a flavoring agent such as peppermint, oil of wintergreen or cherry. When the unit dosage unitform is a capsule, it may contain, in addition to materials of the above type, a liquid carrier such as fatty oil. Various other materials may be present as coatings or to otherwise modify the physical form of the dosage unit. For instance, tablets may be coated with shellac, sugar or both. A syrup or elixir may contain the active compound, sucrose as a sweetening agent, methyl and propyl parabens as preservatives, a dye and a flavoring such as cherry or orange flavor.

Sterile compositions for injection can be formulated according to conventional pharmaceutical practice by dissolving or suspending the active substance in a vehicle such as water for injection, a naturally occuring vegetable oil like sesame oil, coconut oil, peanut oil, cottonseed oil, etc., or a synthetic fatty vehicle like ethyl oleate or the like. Buffers, preservatives, antioxidants and the like can be incorporated as required.

The following examples further illustrate the preparation of the compounds of Formula I and their incorporation into pharmaceutical compositions and, as such, are not to be considered or construed as limiting the invention recited in the appended claims.

EXAMPLE 1

4'-bromomethylbiphenyl-2-tert-butylsulfonamide

Step 1: Preparation of 2-bromobenzene(tert-butyl)sulfonamide

To a stirred solution of 2-bromobenzenesulfonyl chloride (Lancaster Synthesis) (2.21 g, 8.65 mmol) in chloroform (40 ml) under nitrogen at room temperature was added tert-butylamine (Aldrich) (2.30 ml, 21.9 mmol). The orange solution was stirred at room temperature for 12 h, then the mixture evaporated to dryness. Flash chromatography (silica gel, 10,15% ethyl acetate-hexane) afforded 2-bromobenzene(tert-butyl)sulfonamide as a white solid.

$^1$H NMR (300 MHz, CDCl$_3$) $\delta$8.18 (d, J=8.5 Hz, 1H), 7.73 (d, J=8.5 Hz, 1H), 7.50-7.35 (m, 2H), 5.11 (s, 1H), 1.20 (s, 9H).

Step 2: Preparation of p-tolyltrimethyltin p-Tolylmagnesium bromide solution (Aldrich) (1.0M solution in diethyl ether) (53 ml, 0.0530 mol) was added dropwise to trimethyltin chloride (6.92 g, 0.0347 mol) in tetrahydrofuran (50 ml) under nitrogen at −10° C. The suspension was allowed to warm slowly to room temperature over 3 h then saturated ammonium chloride solution (10 ml) was added followed by sufficient water to dissolve the precipitate. The solution was extracted three times with diethyl ether-hexane (1:1). The combined organic phase was washed with brine, dried (magnesium sulfate) and the solvents removed in vacuo. Vacuum distillation of the residue afforded a colorless liquid (39°–40° C., 0.1 mm Hg) which was further purified by flash chromatography (silica gel, hexane) to give p-tolyltrimethyltin as a colorless liquid.

$^1$H NMR (300 MHz, CDCl$_3$) $\delta$7.40 (d, J=7.7 Hz, 2H), 7.19 (d, J=7.7 Hz, 2H), 2.34 (s, 3H), 0.30 (s, 9H).

Step 3: Preparation of 4'-methylbiphenyl-2-tert-butylsulfonamide

2-Bromobenzene(tert-butyl)sulfonamide (1.00 g, 3.92 mmol), p-tolyl-trimethyltin (1.95 g, 6.67 mmol), bis(triphenylphosphine)palladium(II) chloride (Aldrich) (165 mg, 0.235 mmol) and dimethylformamide (25 ml) were heated with stirring under nitrogen at 90° C. for 5 h. The black suspension was cooled to room temperature, then filtered through a pad of celite which was washed with tetrahydrofuran. The colorless filtrate was evaporated to dryness then chromatographed (silica gel, 8,10% ethyl acetate-hexane) to give 4'-methylbiphenyl-2-tert-butylsulfonamide as a white solid.

$^1$H NMR (300 MHz, CDCl$_3$) $\delta$8.16 (d, J=7.9 Hz, 1H), 7.60-7.37 (m, 4H), 7.36-7.24 (m, 3H), 3.57 (s, 1H), 2.42 (s, 3H), 0.99 (s, 9H).

Step 4: Preparation of 4'-bromomethylbiphenyl-2-tert-butylsulfonamide

N-Bromosuccinimide (0.387 g, 2.17 mmol), a,a'-azoisobutyronitrile (catalytic), 4'-methylbiphenyl-2-tert-butylsulfonamide (0.55 g, 1.81 mmol) and carbon tetrachloride (50 ml) were heated with stirring at reflux for 3 h. After cooling to room temperature the mixture was filtered and the filtrate evaporated to dryness. Flash chromatography (silica gel, 10,20% ethyl acetate-hexane) afforded 4'-bromomethylbiphenyl-2-tert-butylsulfonamide (77% pure (the remainder of the material was 4'-dibromomethylbiphenyl-2-tert-butylsulfonamide)) as a white solid.

$^1$H NMR (300 MHz, CDCl$_3$) $\delta$8.17 (dd, J=7.5, 1.6 Hz, 1H), 7.68-7.45 (m, 6H), 7.31 (dd, J=7.5, 1.6 Hz, 1H), 4.55 (s, 2H), 3.52 (s, 1H), 1.00 (s, 9H).

EXAMPLE 2

5,7-dimethyl-2-ethyl-3-(2'-(aminosulfonyl)(1,1'-biphen-4-yl)methyl)-imidazo[4,5-b]pyridine Step 1: Preparation of 5,7-dimethyl-2-ethyl-3-(2'-((tert-butylamino)sulfonyl)(1,1'-biphen-4-yl)methyl)-imidazo[4,5-b]pyridine 5,7-Dimethyl-2-ethyl-imidazo[4,5-b]pyridine [prepared by the method described in European Patent Application 400,974] (0.132 g, 0.753 mmol) was added to a stirred suspension of sodium hydride (60% dispersion) (0.03 g, 0.75 mmol) in dimethylformamide (3 ml) at room temperature under nitrogen. The mixture was heated at 50° C. for 45 min then cooled to room temperature. A solution of 4'-(bromomethyl)biphenyl-2-tert-butylsulfonamide (77% pure) (0.413 g, 0.832 mmol) in dimethylformamide (3 ml) was added dropwise and the solution heated at 50° C. for 4 h. After cooling to room temperature the solvent was removed in vacuo. Flash chromatography (silica gel, 40, 60% ethyl acetate-hexane) afforded 5,7-dimethyl-2-ethyl-3-(2'-((tert-butylamino)sulfonyl)(1,1'-biphen-4-yl)methyl)imidazo[4,5-b]pyridine as a white solid.

$^1$H NMR (300 MHz, CDCl$_3$) $\delta$8.16 (d, 1H), 7.58–7.41 (m, 4H), 7.30–7.16 (m, 3H), 6.91 (s, 1H), 5.52 (s, 2H), 3.48 (s, 1H), 2.83 (q, 2H), 2.64 (s, 3H), 2.59 (s, 3H), 1.36 (t, 3H), 0.94 (s, 9H). FAB-MS: 477 (M+H), 246 (C$_{13}$H$_{12}$NO$_2$S).

Step 2: Preparation of 5,7-dimethyl-2-ethyl-3-(2'-(aminosulfonyl)(1,1'-biphen-4-yl)methyl)imidazo[4,5-b]pyridine Anisole (6 drops) was added to a stirred solution of 5,7-dimethyl-2-ethyl-3-(2'-((tertbutylamino)sulfonyl)(1,1'-biphen-4-yl)methyl)imidazo[4,5-b]pyridine (0.264 g, 0.554 mmol) in trifluoroacetic acid (6 ml) under nitrogen at room temperature. The solution was stirred at room temperature for 8 h then the solvent removed in vacuo. Flash chromatography (silica gel, 60, 70% ethyl acetate-hexane, 0.5% ammonia) afforded 5,7-dimethyl-2-ethyl-3-(2'-(aminosulfonyl)(1,1'-biphen-4-yl)methyl)-imidazo[4,5-b]pyridine as a white solid.

$^1$H NMR (400 MHz, CDCl$_3$) $\delta$8.11 (dd, 1H), 7.53 (dt, 1H), 7.46 (dt, 1H), 7.38 (m, 2H), 7.25 (m, 1H), 7.18 (d, 2H), 6.88 (s, 1H), 5.51 (s, 2H), 4.32 (s, 2H), 2.82 (q, 2H), 2.61 (s, 3H), 2.54 (s, 3H), 1.32 (t, 3H). FAB-MS: 421 (M+H), 246 (C$_{13}$H$_{12}$NO$_2$S).

EXAMPLE 3

5,7-dimethyl-2-ethyl-3-(2'-((isopropylsulfonylamino)sulfonyl)(1,1'-biphen-4-yl)methyl)imidazo[4,5-b]pyridine To a stirred suspension of NaH (0.006 g, 0.15 mmol) in dry DMF (1.0 ml) under nitrogen at room temperature was added 5,7-dimethyl-2-ethyl-3-(2'-(aminosulfonyl)(1,1'-biphen-4-yl)methyl)-imidazo[4,5-b]pyridine (0.05 g, 0.12 mmol). After stirring for 30 minutes at room temperature, isopropylsulfonylchloride (0.04 ml, 0.36 mmol) was added, and the resulting mixture was stirred at room temperature for 18 h. The reaction mixture was poured into ice water (50 ml), acidified with 5% citric acid solution and extracted with chloroform (15 ml×3). The combined organic phase was washed with water and brine, and then dried over MgSO$_4$. Removal of the solvent gave the crude product as a foam which was purified by flash-chromatography starting with 5% MeOH—CH$_2$Cl$_2$ and then with CH$_2$Cl$_2$—MeOH—NH$_4$OH (40:10:1) to give the desired product as a cream colored solid.

$^1$H NMR (300 MHz, CD$_3$OD): $\delta$8.25 (dd, J=7.7, 1.7 Hz, 1H), 7.60–7.40 (m, 3H), 7.29–7.15 (m, 3H), 7.08 (s, 1H), 5.63 (s, 2H), 3.25 (m, 1H), 2.99 (q, J=7.5 Hz, 2H), 2.66 (s, 3H), 2.64 (s, 3H), 1.37 (t, J=7.5 Hz, 3H), 1.26 (d, J=6.83 Hz, 6H). FAB-MS: 527 (M+H).

EXAMPLE 4

5,7-dimethyl-2-ethyl-3-(2'-((2-bromophenylsulfonylamino)sulfonyl)(1,1'-biphen-4-yl)methyl)imidazo[4,5-b]pyridine The titled compound was prepared by using a similar procedure to that described in Example 2.

$^1$H NMR (300 MHz, CD$_3$OD): $\delta$7.88 (dd, J=7.7, 1.7 Hz, 1H), 7.72 (d, J=7.7 Hz, 1H), 7.55 (d, 1H), 7.46 (d, 1H), 7.30–6.85 (m, 12H), 6.82 (s, 1H), 5.35 (s, 2H), 2.68 (q, J=7.5 Hz, 2H), 2.47 (s, 3H), 2.42 (s, 3H), 1.15 (t, J=7.5 Hz, 3H). FAB-MS: 677,679 (M+H).

EXAMPLE 5

5,7-dimethyl-2-ethyl-3-(2'-((phenylsulfonylamino)sulfonyl)(1,1'-biphen-4-yl)methyl)imidazo[4,5-b]pyridine The titled compound was prepared by using a similar procedure to that described in Example 2.

$^1$H NMR (300 MHz, CDCl$_3$): $\delta$7.88 (d, J=7.7 Hz, 1H), 7.50 (d, J=7.7 Hz, 2H), 7.29–6.87 (m, 11H), 6.79 (s, 1H), 5.35 (s, 2H), 2.73 (q, J=7.5 Hz, 2H), 2.58 (s, 3H), 2.44 (s, 3H), 1.22 (t, J=7.5 Hz, 3H). FAB-MS: 583 (M+Na).

EXAMPLE 6

5,7-dimethyl-2-ethyl-3-(2'-((2-thienylsulfonylamino)sulfonyl)(1,1'-biphen-4-yl)methyl)imidazo[4,5-b]pyridine The titled compound was prepared by using a similar procedure to that described in Example 2.

$^1$H NMR (300 MHz, CDCl$_3$): $\delta$7.88 (d, J=7.7 Hz, 1H), 7.30–6.9 (m, 10H), 6.79 (s, 1H), 6.56 (m, 1H), 5.38 (s, 2H), 2.75 (q, J=7.5 Hz, 2H), 2.58 (s, 3H), 2.44 (s, 3H), 1.22 (t, J=7.5 Hz, 3H). FAB-MS: 567 (M+H).

EXAMPLE 7

5,7-dimethyl-2-ethyl-3-(2'-((dibenzylphosphonylamino)sulfonyl)(1,1'-biphen-4-yl)methyl)imidazo[4,5-b]pyridine To a stirred solution of 5,7-dimethyl-2-ethyl-3-(2'-(aminosulfonyl)(1,1'-biphen-4-yl)methyl)imidazo[4,5-b]pyridine (0.076 g, 0.18 mmol) in dry THF (1.5 ml) was added n-BuLi (1.6M solution in hexane) (0.23 ml, 0.36 mmol) at 0° C. After stirring for 15 minutes at that temperature, a solution of dibenzylphosphorylchloride (0.097 g, 0.36 mmol) in THF (0.5 ml) was added, and the resulting mixture was stirred at room temperature for 18 h. The reaction mixture was concentrated under reduced pressure, and the residue was treated with 5% citric acid solution (5 ml) and extracted with methylene chloride (15 ml×3). The combined organic phase was washed with water and brine, and then dried over MgSO$_4$. The crude product obtained after removal of the solvent was purified on silica-gel by flash-chromatography using chloroform-MeOH—NH$_4$OH (90:10:0.5) to give the title product.

$^1$H NMR (300 MHz, CD$_3$OD): $\delta$8.25 (dd, J=7.7, 1.7 Hz, 1H), 7.40–6.90 (m, 18H), 6.78 (s, 1H), 5.28 (s, 2H), 4.6 (s, 4H), 2.78 (q, J=7.5 Hz, 2H), 2.54 (s, 3H), 2.44 (s, 3H), 1.24 (t, J=7.5 Hz, 3H), 1.26 (d, J=6.83 Hz, 6H). FAB-MS: 703 (M+Na).

EXAMPLE 8

5,7-dimethyl-2-ethyl-3-(2'-((diethylphosphonylamino)-sulfonyl)(1,1'-biphen-4-yl)methyl)imidazo[4,5-b]pyridine The titled compound was prepared by using a similar procedure to that described in Example 7.

$^1$H NMR (300 MHz, CDCl$_3$): δ8.15 (d, J=7.7 Hz, 1H), 7.40–6.95 (m, 7H), 6.85 (s, 1H), 5.45 (s, 2H), 3.75 (m, 4H), 2.82 (q, J=7.5 Hz, 2H), 2.61 (s, 3H), 2.47 (s, 3H), 1.32 (t, J=7.5 Hz, 3H), 1.03 (t, 6H). FAB-MS: 557 (M+H).

EXAMPLE 9

Methyl 2-ethyl-7-methylimidazo[4,5-b]pyridine-5-carboxylate

Step 1: Preparation of 2-ethyl-7-methylimidazo[4,5-b]pyridine-4-oxide

A solution of 2-ethyl-7-methylimidazo[4,5-b]pyridine (28 g, 174 mmol) and m-chloroperbenzoic acid (80–90%, 44.6 g) in CHCl$_3$ (300 mL) was heated at reflux for 0.5 h. The mixture was concentrated and purified (SiO$_2$, 100% CH$_2$Cl$_2$ gradient to 30% CH$_2$Cl$_2$/MeOH) to afford 2-ethyl-7-methylimidazo[4,5-b]pyridine-4-oxide as a solid.

$^1$H NMR (300 MHz, CD$_3$OD) δ8.13 (d, 1H, J=6 Hz), 7.13 (d, 1H, J=6 Hz), 3.01 (q, 2H, J=7.5 Hz), 2.60 (s, 3H), 1.46 (t, 3H, J=7.5 Hz).

Step 2: Preparation of 5-chloro-2-ethyl-7-methylimidazo[4,5-b]pyridine

A mixture of 2-ethyl-7-methylimidazo[4,5-b]pyridine-4-oxide (29.75 g, 0.168 mol), CHCl$_3$ (25 mL) and POCl$_3$ (160 mL) was heated to 80° C. for 1 h. After pouring over ice, the mixture was neutralized by careful addition of NH$_4$OH and extracted with EtOAc. Concentration gave 5-chloro-2-ethyl-7-methylimidazo[4,5-b]pyridine as a solid.

$^1$H NMR (250 MHz, CDCl$_3$) δ7.07 (s, 1 H) 3.10 (q, 2H, J=7.5 Hz), 2.67 (s, 3H), 1.48 (t, 3H, J=7.5 Hz).

Step 3: Preparation of 5-bromo-2-ethyl-7-methylimidazo[4,5-b]pyridine

A mixture of 5-chloro-2-ethyl-7-methylimidazo[4,5-b]pyridine (22.2 g, 0.113 mol) in 30% HBr-HOAc was heated to 100° C. for 19 h. The mixture was poured onto ice, neutralized with NH$_4$OH, extracted (5×EtOAc), and the organic layers were concentrated to afford 5-bromo-2-ethyl-7-methylimidazo[4,5-b]pyridine as a solid, after crystallization from EtOAc.

$^1$H NMR (300 MHz, CDCl$_3$) δ7.22 (s, 1H) 3.13 (q, 2H, J=7.5 Hz), 2.66 (s, 3H), 1.47 (t, 3H, J=7.5 Hz).

Step 4: Preparation of 3-benzyl-5-bromo-2-ethyl-7-methylimidazo[4,5-b]pyridine

To a solution of 5-bromo-2-ethyl-7-methylimidazo[4,5-b]pyridine (10 g, 39 mmol) in DMF (70 mL) at room temperature was added NaH (1.3 g of an 80% dispersion, 43 mmol). After 20 min benzyl bromide (5.15 mL, 43 mmol) was added and the reaction was stirred for 16 h. The mixture was poured onto 500 g of ice and the solid residue was filtered, washed with water and air dried to afford 3-benzyl-5-bromo-2-ethyl-7-methylimidazo[4,5-b]pyridine.

$^1$H NMR (300 MHz, CDCl$_3$) δ7.33–7.22 (m, 3H), 7.19 (s, 1H), 7.11–7.07 (m, 2H), 5.42 (s, 2H), 2.76 (q, 2H, J=7.5 Hz), 2.63 (s, 3H), 1.29 (t, 3H, J=7.5 Hz).

Step 5: Preparation of 3-benzyl-5-cyano-2-ethyl-7-methylimidazo[4,5-b]pyridine

A mixture of 3-benzyl-5-bromo-2-ethyl-7-methylimidazo[4,5-b]pyridine (0.62 g, 1.8 mmol) and CuCN (0.806 g, 9.0 mmol) was heated in pyridine (4 mL) at reflux for 10 h under nitrogen. The reaction was cooled, then water (50 mL), KCN (1.17 g), and EtOAc (20 mL) were added and the mixture was heated to 50° C. for 5 min. Cooling and extraction with EtOAc (2×50 mL) gave 3-benzyl-5-cyano-2-ethyl-7-methylimidazo[4,5-b]pyridine as a tan solid.

$^1$H NMR (400 MHz, CDCl$_3$) δ7.40 (s, 1H) 7.35–7.20 (m, 3H), 7.18–7.07 (m, 2H), 5.44 (s, 2H), 2.83 (q, 2H, J=7.5 Hz), 2.67 (s, 3H), 1.32 (t, 3H, J=7.5 Hz).

Step 6: Preparation of methyl 3-benzyl-2-ethyl-7-methylimidazo[4,5-b]pyridine-5-carboxylate A solution of 3-benzyl-5-cyano-2-ethyl-7-methylimidazo[4,5-b]pyridine (0.44 g, 1.59 mmol) in H$_2$SO$_4$ (4 mL) and H$_2$O (4 mL) was heated to 80° C. for 8 h. The reaction was cooled, MeOH (150 mL) was added, then conc. NH$_4$OH was added until the mixture turned basic. The white solid (NH$_4$)$_2$SO$_4$ was filtered and washed with MeOH. The water and MeOH were removed in vacuo and and the residue was taken up in MeOH and then filtered to remove any remaining (NH$_4$)$_2$SO$_4$. After concentrating, and removal of water from the residue by evaporation from toluene, anhydrous 3% HCl-MeOH (50 mL) was added and the mixture was stirred overnight at rt. Filtration, concentration, and extraction from 5% aqueous Na$_2$CO$_3$ with CH$_2$Cl$_2$ gave methyl 3-benzyl-2-ethyl-7-methylimidazo[4,5-b]pyridine-5-carboxylate as a solid.

$^1$H NMR (300 MHz, CDCl$_3$) δ7.93 (s, 1H) 7.38–7.29 (m, 3H), 7.12–7.03 (m, 2H), 5.53 (s, 2H), 3.96 (s, 3H), 2.78 (q, 2H, J=7.5 Hz), 2.70 (s, 3H), 1.29 (t, 3H, J=7.5 Hz)

Step 7: Preparation of methyl 2-ethyl-7-methylimidazo[4,5-b]pyridine-5-carboxylate.

A mixture of crude methyl 3-benzyl-2-ethyl-7-methylimidazo[4,5-b]pyridine-5-carboxylate (0.75 g) in MeOH (30 mL) and conc. aqueous HCl (1 mL) and 100 mg of moist Pearlman's catalyst were shaken under 1 atm. H$_2$ for 24 h. Filtration, concentration, and extraction from dilute NH$_4$OH with EtOAc followed by drying (Na$_2$SO$_4$), concentration, and purification (SiO$_2$, 5% MeOH/EtOAc) gave methyl 2-ethyl-7-methylimidazo[4,5-b]pyridine-5-carboxylate as a solid.

$^1$H NMR (400 MHz, CDCl$_3$) δ7.90 (s, 1H) 4.00 (s, 3H), 3.10 (q, 2H, J=7.5 Hz), 2.71 (s, 3H), 1.38 (t, 3H, J=7.5 Hz).

EXAMPLE 10

4'-bromomethylbiphenyl-2-(O-tert-butyl)-N-hydroxysulfonamide

Step 1: Preparation of 2-bromobenzene(O-tert-butyl)-N-hydroxysulfonamide

To a stirred solution of 2-bromobenzenesulfonyl chloride (Lancaster Synthesis) (1.0 g, 4.0 mmol) in chloroform (10 ml) under nitrogen at 0° C. was added O-tert-butylhydroxylamine hydrochloride (Fluka) (0.6g, 4.77 mmol) in three portions. The solution was stirred at room temperature for 18 h and then diluted with methylene chloride (20 ml). The organic phase was washed successively with 5% citric acid, water and then dried over MgSO$_4$. Removal of the solvent in vacuo gave the crude product as white solid, which was then purified by flash chromatography (silica gel, 10% ethyl acetate-hexane) to afford 2-bromobenzene(O-tert-butyl)-N-hydroxysulfonamide (1.12 g, 89%) as a white solid;

¹H NMR (300 MHz, CDCl₃) δ8.15 (dd, J=7.5, 2.1 Hz, 1H), 7.75 (d, J=7.6, 1.8 Hz, 1H), 7.55–7.35 (m, 3H), 5.11 (s, 1H), 1.21 (s, 9H). FAB-MS: 309 (M+H).

Step 2: Preparation of 4′-methylbiphenyl-2-(O-tert-butyl)-N-hydroxysulfonamide

A solution of 2-bromobenzene(O-tert-butyl)-N-hydroxysulfonamide (0.31 g, 1.0 mmol), p-tolyltrimethyltin (0.3 g, 1.18 mmol) and bis(triphenylphosphine)palladium(II)chloride (Aldrich) (0.036 g) in dry dimethylformamide (6 ml) was stirred under nitrogen at 90° C. for 6 h. The black suspension was cooled to room temperature, then filtered through a pad of celite which was washed with tetrahydrofuran. The colorless filtrate was evaporated to dryness then purified by flash chromatography (silica gel, 8% ethyl acetate-hexane) to give the titled compound as a semi-solid mass.

¹H NMR (300 MHz, CDCl₃) δ8.15 (d, J=7.8, 1.6 Hz, 1H), 7.67–7.50 (m, 2H), 7.36–7.24 (m, 5H), 5.78 (s, 1H), 2.42 (s, 3H), 1.08 (s, 9H). FAB-MS: 320 (M+H).

Step 3: Preparation of 4′-bromomethylbiphenyl-2-(O-tert-butyl)-N-hydroxysulfonamide A mixture of N-Bromosuccinimide (0.14 g, 0.78 mmol), a,a′-azoisobutyronitrile (10 mg) and 4′-methylbiphenyl-2-(O-tert-butyl)-N-hydroxysulfonamide (0.25 g, 0.78 mmol) in carbon tetrachloride (10 ml) was refluxed for 7 h. After cooling to room temperature the mixture was filtered and the filtrate evaporated to dryness. Flash chromatography (silica gel, 10% ethyl acetate-hexane) afforded 4′-methylbiphenyl-2-(O-tert-butyl)-N-hydroxy sulfonamide as a white solid.

¹H NMR (300 MHz, CDCl₃) δ8.15 (d, J=7.8 Hz, 1H), 7.70–7.30 (m, 7H), 5.72 (s, 1H), 4.55 (s, 2H), 1.08 (s, 9H). FAB-MS: 398, 400 (M+H).

EXAMPLE 11

5,7-dimethyl-2-ethyl-3-(2′-((N-hydroxyamino)sulfonyl)(1,1′-biphen-4-yl)methyl)imidazo[4,5-b]pyridine Step 1: Preparation of 5,7-dimethyl-2-ethyl-3-(2′-((O-tert-butyl-N-hydroxyamino)sulfonyl)(1,1,-biphen-4-yl)methyl)-imidazo[4,5-b]pyridine 5,7-Dimethyl-2-ethyl-imidazo[4,5-b]pyridine (0.079 g, 0.45 mmol) was added to a stirred suspension of sodium hydride (60% dispersion) (12 mg) in dimethylformamide (1 ml) at room temperature under nitrogen. The mixture was heated at 50° C. for 45 min then cooled to room temperature. A solution of 4′-bromomethylbiphenyl-2-(O-tert-butyl)-N-hydroxysulfonamide (0.18 g, 0.45 mmol) in dimethylformamide (1 ml) was added dropwise and the solution heated at 50° C. for 3 h. After cooling to room temperature the solvent o was removed in vacuo. Flash chromatography (silica gel, 40, 60% ethyl acetate-hexane) afforded 5,7-dimethyl-2-ethyl-3-(2′-((O-tert-butyl-N-hydroxyamino)sulfonyl)(1,1′-biphen-4-yl)methyl)-imidazo[4,5-b]pyridine as a glass-like solid.

¹H NMR (300 MHz, CDCl₃): δ8.13 (d, 1H), 7.63–7.48 (m, 2H), 7.42–7.25 (m, 5H), 6.90 (s, 1H), 5.72 (broad s, 1H), 5.51 (s, 2H), 2.83 (q, 2H), 2.64 (s, 3H), 2.59 (s, 3H), 1.36 (t, 3H), 1.02 (s, 9H); FAB-MS: 493 (M+H)(C₂₇H₃₂NO₃S).

Step 2: Preparation of 5,7-Dimethyl-2-ethyl-3-(2′-((N-hydroxyamino)sulfonyl)(1,1′-biphen-4-yl)methyl)-imidazo[4,5-b]pyridine Anisole (2 drops) was added to a stirred solution of 5,7-dimethyl-2-ethyl-3-(2′-((O-tert-butyl-N-hydroxyamino)sulfonyl)(1,1′-biphen-4-yl)methyl)imidazo[4,5-b]pyridine (0.05 g) in trifluoroacetic acid (1.5 ml) under nitrogen at room temperature. The solution was stirred at room temperature for 18 h, and then the solvent was removed in vacuo. The residue was triturated with dry ether and the resulting solid was collected by filteration. The solid was finally crystallized from methanol (by dissolving in minimum amount of hot methanol) to give the crystalline product.

¹H NMR (300 MHz, CD₃OD): δ8.13 (d, 1H), 7.63–7.48 (m, 2H), 7.42–7.25 (m, 5H), 6.90 (s, 1H), 5.51 (s, 2H), 2.83 (q, 2H), 2.64 (s, 3H), 2.59 (s, 3H), 1.36 (t, 3H); FAB-MS: 437 (M+H).

EXAMPLE 12

3-[2′-(3H-1,2,3,5-oxathiadiazole-2-oxide-4-yl)1,1′-biphenyl-4-yl]methyl-5,7-dimethyl-2-ethyl-3H-imidazo[4,5-b]pyridine Step 1: 3-(2′-cyano-1,1′biphenyl-4-yl)methyl-5,7-dimethyl-2-ethyl-3H-imidazo[4,5-b]pyridine To a suspension of 60% NaH (400 mg) in DMF (10 mL) was added the solution of 5,7-dimethyl-2-ethyl-3H-imidazo[4,5-b]pyridine (1.75 g, 10 mmol) DMF (10 mL) at 0° C. After 5 min, 4-bromomethyl-2′-cyano-1,1′-biphenyl (2.72 g, 10 mmol; Eur. Pat. Appl. 324,377, 1989) in DMF (10 mL) was added at 0° C. and the mixture was stirred at rt for 15 hrs. Extractive workup (2×EtOAc) from water followed by purification of the concentrated organic phases (SiO₂,) gave 3-(2′-cyano-1,1′-biphenyl-4-yl)methyl-5,7-dimethyl-2-ethyl-3H-imidazo[4,5-b]pyridine as a solid.

Step 2: 3-(2′-(N-Hydroxymethanimidamide)-1,1,′-biphenyl-4-yl)methyl-5,7-dimethyl-2-ethyl-3H-imidazo[4,5-b]pyridine To a mixture of the 3-(2′-cyano-1,1′-biphenyl-4-yl)methyl-5,7-dimethyl-2-ethyl-3H-imidazo[4,5-b]pyridine (366 mg, 1 mmol) and NH₂OH.HCl (695 mg, 10 mmol) in EtOH (3 mL) was added 25% NaOMe solution in MeOH (2.2 mL, 10 mmol). The solution was refluxed for 48 h. After cooling to rt CHCl₃ (50 mL) was added to the solution. The solution was washed with water (3×) and brine (1×), dried over anhydrous MgSO₄. Concentration afforded the title compound (388 mg) as a white powder.

¹H NMR (CDCl₃, 400 MHz): δ7.52 (d, 1H, J=7.4 Hz), 7.45~7.25 (m, 5H), 7.13 (d, 2H, J=7.8 Hz), 6.88 (s, 1H), 5.46 (s, 2H), 4.37 (s, 2H), 2.78 (q, 2H, J=7.4 Hz), 2.61 (s, 3H), 2.57 (s, 3H), 1.28 (t, 3H, J=7.7 Hz).

Step 3: Preparation of 3-[2′-(3H-1,2,3,5-oxathiadiazole-2-oxide-4-yl)-1,1′-biphenyl-4-yl]methyl-5,7-dimethyl-2-ethyl-3H-imidazo[4,5-b]pyridine To a solution of the 3-(2′-(N-Hydroxymethanimidamide)-1,1′-biphenyl-4-yl)methyl-5,7-dimethyl-2-ethyl-3H-imidazo[4,5-b]pyridine (61.4 mg, 0.15 mmol) in anhydrous pyridine (1 mL) was added the 2N SOCl₂ solution (92 mL, 0.13 mmol) in CH₂Cl₂ dropwise at 0° C. The solution was stirred at 0° C. for 1 h and the reaction was quenched with water. The product was extracted with EtOAc (3×). The organic layer was washed with water (3×) and brine (1×), and dried over anhydrous MgSO₄. After concentration the product was purified by flash chromatography (H:E=1:1, 100% EtOAc) to afford the title compound (31.3 mg) as a solid.

¹H NMR (CDCl₃): δ7.78 (d, 1H, J=7.78 Hz), 7.3 (t, 1H, J=7.1 Hz), 7.44 (t, 1H, J=7.5 Hz), 7.36 (d, 1H, J=7.4 Hz), 7.20 (d, 2H, J=8.0 Hz), 7.11 (d, 2H, J=8.0 Hz), 6.84 (s, 1H), 5.40 (ABq, 2H), 2.70 (q, 2H, J=7.5 Hz), 2.53 (s, 3H), 2.52 (s, 3H), 1.27 (t, 3H, J=7.6 Hz).

EXAMPLE 13

5,7-dimethyl-2-ethyl-3-[2'-(2-(2-bromophenyl)-2,5-dihydro-1,2,3,5-thiatriazole-1-oxide-4-yl)-[1,1']biphenyl-4-yl]methyl-3H-imidazo[4,5-b]pyridine Step 1: Preparation of 2-Bromo-N-(2-cyanoethyl)benzamide 2-Bromobenzoyl chloride (4.389 g, 20 mmol) was dissolved in THF (20 mL) and dripped in 20 equal portions alternating with 20 equal portions of 1N-NaOH (20 mL) into a solution of 2-amino-propionitrile fumarate (2.563 g, 20 mL) at )° C. The solution was stirred at rt for 18 h. After the addition of water the product was extracted with EtOAc (3×). The combined organic layer was washed brine and dried over anhydrous $MgSO_4$. Concentration afforded the carboxamide (4.5 g) as a white powder.

$^1$H NMR ($CDCl_3$, 200 MHz): $\delta 7.62\sim7.20$ (m, 4H), 6.74 (broad m, 1H), 3.66 (q, 2H, J=7.7 Hz), 2.72 (t, 2H, J=7 Hz)

Step 2: Preparation of N-(2-cyanoethyl)-4'-methyl[1,1'-]biphenyl-2-carboxamide

To a mixture of the above amide (233 mg, 0.92 mmol), trimethyl-p-toluyltin (230 mg, 0.92 mmol) and tetrakis(-triphenylphosphine)palladium(O) (53 mg, 0.046 mmol) was added anhydrous toluene (5 mL). The mixture was stirred at 110° C. for 18 h. The solution was diluted with EtOAc and washed with brine. After drying over anhydrous $MgSO_4$ followed by concentration, the product was purified by flash chromatography (H:E=5:1, 1:1) to give the title compound (167 mg) as a solid.

$^1$H NMR ($CDCl_3$, 400 MHz): $\delta 7.68$ (d, 1H, J=7 Hz), 7.55/7.20 (m, 7H), 5.65 (broad m, 1H), 3.43 (q, 2H, J=7.7 Hz), 2.39 (t, 2H, J=7 Hz).

Step 3: Preparation of 2-Phenyl-5-(2'-cyanoethyl)-4-(4'-methyl[1,1']biphenyl-2-yl)-2,5-dihydro-1,2,3,5-thiatriazole-1-oxide The mixture of the above amide (400 mg, 1.52 mmol) and $PCl_5$ (347 mg, 1.67 mmol) was heated with a heat gun under aspirator vacuum over 10 min. After gas evolution ceased the resultant oil was cooled to rt. The oil was dissolved in anhydrous 1,4-dioxane (3 mL) and phenylhydrazine (745 mL, 7.58 mmol) was added at rt dropwise. The solution was stirred at rt over 18 h. The solution was diluted with EtOAc and washed with brine. After drying over anhydrous $MgSO_4$ followed by concentration, the product was purified by flash chromatography (H:E=10:1, 5:1, 1:1) to give the amidrazone (180 mg) as a foamy glass. The above amidrazone (161 mg, 0.455 mmol) was dissolved in $CH_2Cl_2$ (3 mL). To the solution were added pyridine (79 mg, 1 mmol) and 2N-$SOCl_2$ in $CH_2Cl_2$ (250 $\mu$L, 0.5 mmol) at 0° C. The solution was stirred at 0° C. for 30 min and at rt for 1.5 h. The solution was diluted with EtOAc and washed with brine. After drying over anhydrous $MgSO_4$ followed by concentration, the product was purified by flash chromatography (H:E=5:1, 1:1) to give the title compound (180 mg) as a foamy glass.

$^1$H NMR ($CDCl_3$, 400 MHz): $\delta 7.70/7.14$ (m, 13H), 3.50 (m, 1H), 3.33 (m, 1H), 2.36 (s, 3H), 2.10/1.86 (m, 2H)

Step 4: Preparation of 2-(2-Bromophenyl)-5-(2'-cyanoethyl)-4-[4'-(bromomethyl)[1,1']biphenyl-2-yl]-2,5-dihydro-1,2,3,5-thiatriazole-1-oxide To a solution of the above thiatriazole (116 mg, 0.29 mmol) in $CCl_4$ (5 mL) were added NBS (56.8 mg, 0.32 mmol) and AIBN (10 mg). The solution was refluxed for 2 h. The additional NBS (56.8 mg, 0.32 mmol) and AIBN (10 mg) were added and the solution was refluxed for 4 h. The NBS (103 mg, 0.58 mmol) and AIBN (20 mg) were added again and the solution was refluxed for additional 4 h. After cooling the solid was filtered off. The solution was diluted with EtOAc and washed with brine. After drying over anhydrous $MgSO_4$ followed by concentration, the product was purified by flash chromatography (H:E=10:1, 5:1, 1:1) to give the title compound (85.8 mg) as a foamy glass.

$^1$H NMR ($CDCl_3$, 400 MHz): $\delta 7.70/7.35$ (m, 12H), 4.48 (s, 2H), 3.56/3.27 (m, 2H)

Step 5: Preparation of 5,7-dimethyl-2-ethyl-3-[2'-(2-(2-bromophenyl)-2,5-dihydro-1,2,3,5-thiatriazole-1-oxide-4-yl)-[1,1']-biphenyl-4-yl]methyl-3H-imidazo[4,5-b]pyridine To a suspension of 60% NaH (7.3 mg, 0.184 mmol) in DMF (2 mL) was added a DMF (1 mL) solution of the 5,7-dimethyl-2-ethyl-3H-imidazo[4,5-b]pyridine (32.2 mg, 0.184 mmol) at 0° C. The solution was stirred at rt for 15 min. To the solution was added the above bromide (80 mg, 0.143 mmol) in DMF (1 mL) at 0° C. The solution was stirred at rt for 18 h. The solution was diluted with EtOAc and washed with brine. After drying over anhydrous $MgSO_4$ followed by concentration, the product was purified by flash chromatography (H:E=10:1, 5:1, 1:3, 100% EtOAc) to give the title compound (28.4 mg) as a solid.

$^1$H NMR ($CDCl_3$, 400 MHz): $\delta 7.90$ (d, 1H, J=7.7 Hz), 7.55$\sim$7.24 (m, 9H), 7.15 (d, 2H, J=8.1 Hz), 6.87 (s, 1H), 5.45 (ABq, 2H), 2.75 (q, 2H, J=7.5 Hz), 2.59 (s, 3H), 2.56 (s, 3H), 1.28 (t, 3H, 7.6 Hz).

EXAMPLE 14

5,7-dimethyl-2-ethyl-3-[2'-(2-phenyl-2,5-dihydro-1,2,3,5-thiatriazole-1-oxide-4-yl)-[1,1']-biphenyl-4-yl]methyl-3H-imidazo[4,5-b]pyridine Step 1: Preparation of 4-(2-Bromophenyl)-5-(2-cyanoethyl)-2-phenyl-2,5-dihydro-1,2,3,5-thiatriazole-1-oxide The mixture of 2-bromo-N-(2'-cyanoethyl)benzamide (938 mg, 3.71 mmol) and $PCl_5$ (849 mg, 4.08 mmol) was heated with a heat gun under aspirator vacuum over 10 min. After gas evolution ceased the resultant oil was cooled to rt. The oil was dissolved in anhydrous 1,4-dioxane (5 mL) and phenylhydrazine (1.82 mL, 18.54 mmol) was added at rt dropwise. The solution was stirred at rt over 18 h. The solution was diluted with EtOAc and washed with brine. After drying over anhydrous $MgSO_4$ followed by concentration, the product was purified by flash chromatography (H:E=10:1, 5:1, 1:1) to give the amidrazone (260 mg) as a foamy glass. The above amidrazone (250 mg, 0.729 mmol) was dissolved in $CH_2Cl_2$ (5 mL). To the solution were added pyridine (118 $\mu$L, 1.458 mmol) and 2N-$SOCl_2$ in $CH_2Cl_2$ (365 mL, 0.729 mmol) at 0° C. The solution was stirred at 0° C. for 30 min and at rt for 1.5 h. The solution was diluted with EtOAc and washed with brine. After drying over anhydrous $MgSO_4$ followed by concentration, the product was purified by flash chromatography (H:E=5:1, 1:1) to give the title compound (166 mg) as a foamy glass.

$^1$H NMR ($CDCl_3$, 400 MHz): $\delta 7.72$ (d, 1H, J=7.8 Hz), 7.60$\sim$7.35 (m, 7H), 7.17 (t, 1H, 7.3 Hz), 4.11 (m, 1H), 3.72 (m, 1H), 2.79 (m, 1H), 2.66 (m, 1H).

Step 2: Preparation of 2-Ethyl-5,7-dimethyl-3-(4-(trimethylstannylphenyl)methyl)-3H-imidazo[4,5-b]pyridine To a suspension of 60% NaH (223 mg, 5.564 mmol) in DMF (5 mL) was added a DMF (5 mL) solution of the 5,7-dimethyl-2-ethyl-3H-imidazo[4,5-b]pyridine (885 mg, 5.058 mmol) at 0° C. The solution was stirred at rt for 10 min. To the solution was added a-bromo-4-trimethylstannyltoluene (1.688 g, 5.058 mmol) in DMF (5 mL) at 0° C. The solution was stirred at rt for 18 h. The solution was diluted with EtOAc and washed with water. The aqueous layer was extracted with EtOAc (3×). The combined organic layer was washed with brine. After drying over anhydrous $MgSO_4$ followed by concentration, the product was purified by flash chromatography (H:E=10:1, 5:1, 1:3, 100 % EtOAc) to give the title compound (28.4 mg) as a solid.

$^1$H NMR (CDCl$_3$, 400 MHz): δ7.37 (d, 2H, J=7.8 Hz), 7.05 (d, 2H, J=7.3 Hz), 6.86 (s, 1H), 5.42 (s, 2H), 2.77 (q, 2H, J=7.5 Hz), 2.61 (s, 3H), 2.56 (s, 3H), 1.29 (t, 3H, J=7.8 Hz).

Step 3: Preparation of 5,7-dimethyl-2-ethyl-3-[2'-(5-(cyanoethyl)-2-phenyl-2,5-dihydro-1,2,3,5-thiatriazole-1-oxide-4-yl)-[1,1']-biphenyl-4-yl]methyl-3H-imidazo[4,5-b]pyridine A mixture of the above stannyl compound (100 mg, 0.234 mmol), the thiatriazole (80 mg, 0.206 mmol) and bis(triphenylphosphine)Pd(II) chloride (7.2 mg, 0.01) was dissolved in anhydrous DMF (3 mL). The solution was stirred at 120° C. for 4 h. After the reaction was quenched with water the product was extracted with EtOAc (3×). The combined organic layer was washed with brine. After drying over anhydrous $MgSO_4$ followed by concentration, the product was purified by flash chromatography (H:E=5:1, 1:1) to give the title compound (28.4 mg) as a solid.

$^1$H NMR (CDCl$_3$, 400 MHz): δ7.70~7.35 (m, 11H), 7.16 (d, 2H, J=8.0 Hz), 6.90 (s, 1H), 5.46 (ABq, 2H), 3.45 (m, 1H), 3.30 (m, 1H), 2.80 (q, 2H, J=7.5 Hz), 2.62 (s, 3H), 2.56 (s, 3H), 2.12 (m, 2H), 1.30 (t, 3H, J=7.8 Hz).

Step 4: Preparation of 5,7-dimethyl-2-ethyl-3-[2'-(2-phenyl-2,5-dihydro-1,2,3,5-thiatriazole-1-oxide-4-yl)-[1,1']-biphenyl-4-yl]methyl-3H-imidazo[4,5-b]pyridine To a solution of the above thiatriazole (28 mg, 0.049 mmol) in THF (1 mL) was added 5 drops of 5N-NaOH and MeOH (1 mL) at rt. The solution was stirred at rt for 48 h. After concentration the residue was dissolved in water (2 mL). The pH of the solution was adjusted to ~4 by the addition of 1N-HCl. The product was extracted with EtOAc (3×). The combined organic layer was washed with brine. After drying over anhydrous $MgSO_4$ followed by concentration, the product was purified by flash chromatography (H:E=5:1, 1:1) to give the title compound (10.2 mg) as a solid.

$^1$H NMR (CDCl$_3$, 400 MHz): δ7.92 (d, 1H, J=7.6 Hz), 7.51~7.10 (m, 12H), 6.91 (s, 1H), 5.48 (ABq, 2H), 2.81 (q, 2H, J=7.7), 2.62 (s, 3H), 2.58 (s, 3H), 1.30 (t, 3H, J=7.5 Hz).

EXAMPLE 15

5,7-dimethyl-2-ethyl-3-[2'-(N-cyanoaminosulfonyl)[1,1']-biphenyl-4-yl]methyl-3H-imidazo[4,5-b]pyridine To a stirred solution of 5,7-dimethyl-2-ethyl-3-[2'-(aminosulfonyl)[1,1']-biphenyl-4-yl]methyl-3H-imidazo[4,5-b]pyridine (122 mg, 0.29 mmol) in THF (1.5 mL) at 0° C. was added sodium hexamethyldisilazine (0.35 mL of a 1M solution in THF). After 10 min, a solution of BrCN (37 mg, 0.35 mmol) in THF (1 ml) was added dropwise via a double tipped needle. The reaction was warmed to r.t. and stirred for 3 h at which time 0.3 mL of HOAc was added. Extraction with $CH_2Cl_2$ (5×30 mL) from H$_2$O (30 mL), evaporation of the organic extracts and purification (SiO2, 80:19:1 CH$_2$Cl$_2$/CH$_3$OH/NH$_4$OH) gave 5,7-dimethyl-2-ethyl-3-[2'-(N-cyanoaminosulfonyl)[1,1']-biphenyl-4-yl]methyl-3H-imidazo[4,5-b]pyridine as a glass.

$^1$H NMR (200 MHz, CD$_3$OD) δ8.08 (d, 1H, J=7.2 Hz), 7.58–7.44 (m, 2H), 7.39 (d, 2H, J=8.2 Hz), 7.40 (d, 1H, J=7.2 Hz), 7.0 (d, 2H J=8.2 Hz), 7.00 (s, 1H), 5.59 (s, 2H), 2.89 (q, 2H, J=7.5 Hz), 2.60 (s, 3H), 2.58 (s, 3H), 1.29 (t, 3H, J=7.5 Hz).

EXAMPLE 16

2-butyl-3-[2'-[(N-butoxycarbonylaminosulfonyl)[1,1']-biphenyl-4-yl]methyl-6-[(1-oxopentyl)amino]-3H-imidazo[4,5-b]pyridine Step 1: Preparation of 2-amino-3,5-dinitropyridine To a stirred solution of 2-amino-3-nitropyridine in conc. H$_2$SO$_4$ (50 mL) at 0° C. was added HNO$_3$ (3.10 mL, d=1.49) dropwise over 10 min. The mixture was warmed to r.t. for 20 min then heated to 50° C. for 90 min. The reaction mixture was cooled and poured into 400 g of ice. The resulting precipitate was filtered and air dried to give 10.3 g of 2-amino-3,5-dinitropyridine as a yellow solid.

Step 2: Preparation of 6-[(1-oxopentyl)amino)]-2-butylimidazo[45-b]pyridine

A mixture of 2-amino-3,5-dinitropyridine (5.32 g, 28.9 mmol), THF (100 mL), methanol (250 mL) and Raney-nickel (3 mL of a 1:1 suspension in H$_2$O) was stirred under H$_2$ (1 atm.) was stirred for 5 h. The reaction mixture was quickly filtered into a receiving flask containing 5 mL of conc. HCl and the solvent was removed in vacuo at r.t. To this crude 2,3,5-triaminopyridine.HCl was added valetic acid (9.43 mL, 86.7 mmol) and polyphosphoric acid (100 mL) and this mixture was heated to 95° C. for 6 h. The warmed mixture was poured into stirred ice-H$_2$O (200 mL) and this mixture was cooled and neutralized (to pH 4) by the addition of conc. NH$_4$OH. Extraction with EtOAc (3×75 mL), concentration, and purification (SiO2, 5% MeOH/EtOAc) gave 6-[(1-oxopentyl)amino)]-2-butylimidazo[4,5-b]pyridine as a solid. Step 3: Preparation of 2-butyl-3-[2'-(N-tert-butylaminosulfonyl)[1,1']-biphenyl-4-yl]methyl-6-[(1-oxopentyl)amino)]-3H-imidazo[4,5-b]pyridine A solution of 6-[(1-oxopentyl)amino)]-2-butylimidazo[4,5-b]pyridine, K$_2$CO$_3$ (956 mg, 6.92 mmol), and 4'-bromomethylbiphenyl-2-tert-butylsulfonamide 1.65 g, 3.46 mmol) in DMF (15 mL) was stirred for 12 h at r.t. The reaction mixture was poured into H$_2$O (50 mL), extracted with EtOAc (2×50 mL), concentrated, and purified (SiO2, 4:1 EtOAc/hexanes) to give 740 mg of 2-butyl-3-[2'-(N-tert-butyl-aminosulfonyl)[1,1']biphenyl-4-yl]methyl-6-[(1-oxopentyl)amino)]-3H-imidazo[4,5-b]pyridine as a foam.

Step 4: Preparation of 2-butyl-3-[2'-(aminosulfonyl)[1,1']-biphenyl-4-yl]methyl-6-[(1-oxopentyl)amino)]-3H-imidazo[4,5-b]pyridine A solution of 2-butyl-3-[2'-(N-tert-butylaminosulfonyl)[1,1']-biphenyl-4-yl]methyl-6-[(1oxopentyl)amino)]-3H-imidazo[4,5-b]pyridine (710 mg, 1.23 mmol) in trifluoroacetic acid (50 mL) was stirred at r.t. for 12 h. The mixture was concentrated, dissolved in EtOAc (40 mL) and washed with saturated aqueous Na$_2$CO$_3$. The organic extracts were dried (K$_2$CO$_3$) and concentrated to give 2-butyl-3-[2'-(aminosulfonyl)[1,1']- biphenyl-4-yl]methyl-6-[(1-oxopentyl)amino)]-3H-imidazo[4,5-b]pyridine as a solid.

Step 5: Preparation of 2-butyl-3-[2'-(N-butoxycarbonylaminosulfonyl)[1,1']-biphenyl-4-yl]methyl-6-[(1-oxopentyl)amino)]-3H-imidazo[4,5-b]pyridine To a mixture of 2-butyl-3-[2'-(aminosulfonyl)[1,1']-biphenyl-4-yl]methyl-6-[(1-oxopentyl)amino)]-3H-imidazo[4,5-b]pyridine (65 mg, 0.124 mmol) and 4-dimethyaminopyridine (45 mg, 0.373 mmol) in pyridine (1.5 mL) was added n-butylchloroformate (0.078 mL, 0.62 mmol). After 48 h at r.t., MeOH (2 mL) was added and the mixture was concentrated, dissolved in EtOAc (40 mL), washed with $H_2O$ (15 mL), concentrated, and purified (SiO2, (97:3 $CH_2Cl_2$/MeOH) to give 2-butyl-3-[2'-(N-butoxycarbonylaminosulfonyl)[1,1']-biphenyl-4-yl]methyl-6-[(1-oxopentyl)amino)]-3H-imidazo[4,5-b]pyridine as a solid.

$^1$H NMR (200 MHz, $CD_3OD$) δ8.48 (d, 1H, J=2 Hz), 8.30 (d, 1H, J=2 Hz) 8.15 (dd, 1H, J=1.4 and 7.8 Hz), 7.68–7.48 (m, 2H), 7.35–7.20 (m, 3H), 7.10 (d, 2H J=8.2 Hz), 5.53 (s, 2H), 3.89 (t, 2H, J=6.4 Hz) 2.87 (t, 2H, J=7.4 Hz), 2.39 (t, 2H, J=7.2 Hz), 1.85–1.56 (m, 4H), 1.55–0.70 (m, 17H).

EXAMPLE 17

5,7-Dimethyl-2-ethyl-3-[2'-[(N-ethoxycarbonyl)aminosulfonyl)[1,1']-biphenyl-4-yl]methyl-3H-imidazo[4,5-b]pyridine To a stirred suspension of NaH (0.014 g, 0.36 mMol) in dry DMF (1.5ml) was added 5,7-dimethyl-2-ethyl-3-[2'-(aminosulfonyl)[1,1']-biphenyl-4-yl]methyl-3H-imidazo[4,5-b]pyridine (Example 2) (0.075 g, 0.18 mMol) at 25° C. After 15 min. of stirring, ethylchloroformate (0.034 ml, 0.36 mMol) was added to the above mixture and stirring continued at that temperature for 15 h. The reaction mixture was then diluted with ice-water and acidified with 10% citric acid. The precipitate obtained was extracted into ethylacetate (30ml), and the organic phase was washed with water and then dried over anhydrous $MgSO_4$. Removal of the solvent in vacuo gave the crude product which was purified by flash-chromatography using $CH_2Cl_2$—MeOH—$NH_4OH$ (90:10:1) to give the desired compound (0.024 g) as an amorphous solid.

$^1$H NMR (400 MHz, $CD_3OD$) δ8.1 (d, 1H, J=7.2 Hz), 7.50–7.40 (m, 2H), 7.35 (d, 2H, J=8.2 Hz), 7.15 (d, 1H, J=7.2 Hz), 7.10 (d, 2H J=8.2 Hz), 7.00 (s, 1H), 5.58 (s, 2H), 3.72 (t, 2H, J=8 Hz) 2.92 (t, 2H, J=7.4 Hz), 2.60 (s, 3H), 2.57 (s, 3H), 1.31 (t, 3H), 1.02 (t, 3H). FAB-MS: m/e 493 (M+1)

EXAMPLES A1 TO A12

The compounds of the Formula (II) wherein $R^{2a}$ is H, Et, Pr, Bu or i-Bu and $R^{3a}$ is H or 3-F exemplified in Table A below are prepared from the appropriate substituted starting materials utilizing the general procedures outlined in the noted schemes.

TABLE A

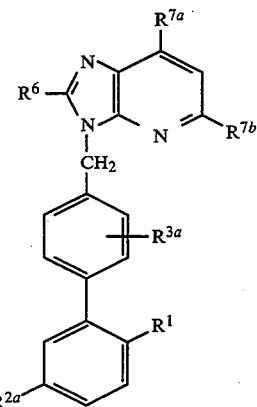

(II)

| Compound No. # | $R^1$ | $R^6$ | $R^{7a}$ | $R^{7b}$ | Scheme |
|---|---|---|---|---|---|
| A3 | —SO$_2$NHSO$_2$Me | Et | Me | Me | 8 |
| A4 | —SO$_2$NHSO$_2$iPr | Pr | CO$_2$H | Me | 8 |
| A5 | ![structure] | Et | Me | Me | 16, 17 |
| A6 | ![structure] | Et | Me | Me | 18–20 |
|  |  | Et | CO$_2$H | Me | 25 |
| A1 | —SO$_2$NHOH | Et | Me | Me |  |
| A2 | —SO$_2$NHSO$_2$Ph | Et | Me | Me |  |
| A3 | —SO$_2$NHSO$_2$Me | Et | Me | Me |  |

TABLE A-continued

(II)

| Compound No. # | R¹ | R⁶ | R⁷ᵃ | R⁷ᵇ | Scheme |
|---|---|---|---|---|---|
| A4 | —SO₂NHSO₂— 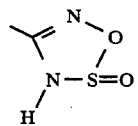 | Pr | CO₂H | Me | |
| A5 | 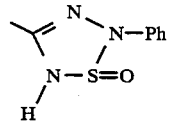 | Et | Me | Me | |
| A6 | 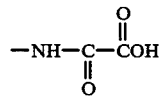 | Et | Me | Me | |
| A7 | —NH—C(=O)—COH(=O) 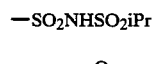 | Et | CO₂H | Me | 25 |
| A8 | —SO₂NHSO₂iPr | Et | Me | Me | 8 |
| A9 | —SO₂NHPO(=O)—CH₂Ph, OCH₂PH 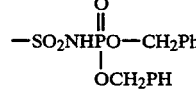 | Et | Me | Me | 13 |
| A10 | 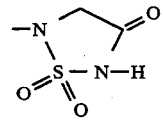 | Et | Me | Me | 21 |
| A11 | 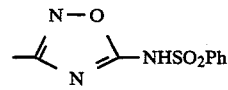 —NHSO₂Ph | Et | Me | Me | 11 |
| A12 | 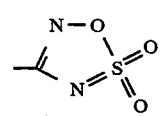 | Et | Me | Me | 15. |

EXAMPLES F1 TO F11

The compounds of the formula (IV), wherein $R^{2a}$ is H, Et, Pt, Bu or i-Bu, exemplified in Table F are prepared from the appropriately substituted starting material utilizing the general procedures outlined in the noted schemes.

TABLE F

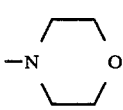

(IV)

| Compound No. | R¹ | R⁶ | R⁷ᶜ | R⁷ᵈ | Scheme |
|---|---|---|---|---|---|
| F1 | —SO₂NHOH | Pr | Me | —NHCH₃ | 26 |
| F2 | —SO₂NHOH | Pr | Me | -N(morpholino)-O | 26 |
| F3 | —SO₂NHSO₂iPr | Pr | Me | -N(morpholino)-O | 8 |
| F4 | —SO₂NHSO₂Ph | Et | Me | —NHCH₃ | 8, 9 |
| F5 | —SO₂NHP(=O)(OCH₂Ph)(OCH₂Ph) | Pr | Me | -N(morpholino)-O | 13 |
| F6 | (cyclic sulfamide with ketone) | Et | Me | -N(morpholino)-O | 21 |
| F7 | (cyclic sulfamide with ketone) | Pr | Me | —NHCH₃ | 21 |
| F8 | (oxadiazole-NHSO₂Ph) | Pr | Me | -N(morpholino)-O | 21 |
| F9 | (N-Ph cyclic sulfonamide) | Pr | Me | —NHCH₃ | 18–20 |
| F10 | (N—O cyclic S=O, NH) | Et | Me | -N(morpholino)-O | 16, 17 |

TABLE F-continued (IV) [Structure: imidazo[4,5-b]pyridine with R7c, R7d, R6, and biphenyl bearing R1, R2a substituents via CH2]

| Compound No. | R¹ | R⁶ | R⁷ᶜ | R⁷ᵈ | Scheme |
|---|---|---|---|---|---|
| F11 | [structure: C(=N-O-)(CH3)—C(=N)—NHSO₂CF₃] | Pr | Me | [morpholino: —N(CH₂CH₂)₂O] | 23. |

EXAMPLES G1 TO G11

The compounds of the formula (V), wherein $R^{2a}$ is H, Et, Pr, Bu or i-Bu, exemplified in Table G are prepared from the appropriate substituted starting material utilizing the general procedures outlined in the noted schemes.

TABLE G (V) [Structure: xanthine-like imidazo-pyrimidinedione with R⁶, R⁸ᵇ, R⁸ᶜ substituents, linked through CH₂ to biphenyl with R¹ and R²ᵃ]

| Compound No. | R¹ | R⁶ | R⁸ᵇ | R⁸ᶜ | Scheme |
|---|---|---|---|---|---|
| G1 | —SO₂NHOH | Pr | Me | Me | 26 |
| G2 | —SO₂NHOH | nBu | Me | Me | 26 |
| G3 | —SO₂NHSO₂Ph | Pr | Me | Me | 8, 9 |
| G4 | [structure: —N(SO₂)(C(=O)CH₂)NH cyclic sulfonamide] | Pr | Me | Me | 21 |
| G5 | [structure: C(=N-O-)(CH3)—C(=N)—NHSO₂Ph] | nBu | Me | Me | 23. |

EXAMPLE 18

5,7-dimethyl-2-ethyl-3[[2'-(N-butyloxycarbonylaminosulfonyl)-5'-ethyl[1,1'biphenyl]-4-yl]methylimidazo[4,5-b]pyridine Step 1: Preparation of 4-ethylbenzene-t-butylsulfonamide (Scheme 27, compound 94, $R^{2a}$ = ethyl).

To a solution of 4-ethylbenzenesulfonyl chloride (Lancaster) in anhydrous CH₂Cl₂ (0.5M solution) cooled to 0° C. under N₂ was added t-butylamine (2.2 equiv) slowly through a dropping funnel. After complete addition, the reaction was stirred at rt for 12 h. The CH₂Cl₂ was removed under reduced pressure and the residue was extracted into Et₂O and washed with 2N NaOH, H₂O and brine. The organic was dried over anhydrous MgSO$_4$ and concentrated in vacuo to afford the titled product. Rf=0.42 (3:1 Hex/EtOAc).

Step 2: Preparation of 2-t-butylsulfonamido-5-ethylphenylboric acid (Scheme 27, compound 95, R$^{2a}$=ethyl).

To a solution of 4-ethylphenyl-t-butylsulfonamide (6.44 g, 26.7 mmoL) in anhydrous THF (60 mL) cooled to −20° C. under N$_2$ was added 2.5M n-BuLi solution (27 mL, 2.5 equiv). The mixture was warmed to rt and stirred for 2 h. To the mixture, containing the bright orange dianion at 0° C., was added B(OiPr)$_3$ (9.3 mL, 1.5 equiv). The reaction was allowed to warm to rt and stirred overnight. The next day 2N HCl (3 mL) was added and the mixture was stirred for 1 h. The solvent was removed under reduced pressure and the residue was extracted with EtOAc. The organic was washed with 2N HCl, H$_2$O and brine. The organic was dried over anhydrous MgSO$_4$ and concentrated in vacuo to afford the titled compound. Rf=0.5 (1:1 EtOAc/Hex). The material was used in subsequent steps without further purification.

Step 3: Preparation of 5,7-dimethyl-2-ethyl-3[[2'-(N-t-butylsulfonamido)-5'-ethyl-[1,1'biphenyl]-4-yl]methylimidazo[4,5-b]pyridine (Scheme 27, compound 97, R$^{2a}$=ethyl).

To a solution of 5,7-dimethyl-2-ethyl-3[4-bromophenyl]methylimidazo[4,5-b]pyridine (482 mg, 1.40 mmol) and the product of step 2 (800 mg, 2.8 mmol) in toluene (20 mL) was added 1.25N NaOH (5 mL), EtOH (14 mL) and Pd(PPh$_3$)$_4$ (97 mg, 3 mol %). The reaction mixture was stirred at 100° C. under N$_2$ for 2 h. The solvent was removed under reduced pressure and the residue was taken up in EtOAc. The organic was washed with 1N NaOH, H$_2$O and brine and dried over anhydrous MgSO$_4$ and concentrated in vacuo. The titled product was recrystallized from EtOAc/Hex. Rf=0.32 (1:1 EtOAc/Hex).

$^1$H NMR (200 MHz, CD$_3$OD) δ0.96 (s, 9H), 1.23 (t, 3H), 1.32 (t, 3H), 2.58 (s, 3H), 2.61 (s, 3H), 2.71 (q, 2H), 2.90 (q, 2H), 5.60 (s, 2H), 7.02 (s, 1H), 7.10 (d, 1H), 7.14 (d, 2H), 7.33 (dd, 1H), 7.39 (d, 2H), 7.98 (d, 1H).

Step 4: Preparation of 5,7-dimethyl-2-ethyl-3[[2'-(sulfonamido)-5'-ethyl[1,1'bi-phenyl]-4-yl]methylimidazo[4,5-b]pyridine (Scheme 27, compound 98, R$^{2a}$=ethyl).

To a mixture of the product of step 3 (185 mg, 0.367 mmol) and anisole (0.2 mL) was added TFA (3 mL). After standing at rt for 24 h, the mixture was concentrated in vacuo. The residue was taken up in EtOAc and washed with 2N Na$_2$CO$_3$ solution, H$_2$O and brine. The organic was dried over anhydrous MgSO$_4$ and concentrated in vacuo. The titled product, crystallized from Hex/Et$_2$O, was obtained as a white powder. Rf=0.42 (3:1 EtOAc/Hex).

$^1$H NMR (400 MHz, CD$_3$OD) δ1.23 (t, 3H), 1.29 (t, 3H), 2.58 (s, 3H), 2.61 (s, 3H), 2.71 (q, 2H), 2.90 (q, 2H), 5.61 (s, 2H), 7.02 (s, 1H), 7.11 (s, 1H), 7.15 (d, 2H), 7.35 (t, 3H), 7.97 (d, 1H).

Step 5: Preparation of 5,7-dimethyl-2-ethyl-3[[2'-(N-butyloxycarbonylaminosulfonyl)-5'-ethyl[1,1'-biphenyl]-4-yl]methylimidazo[4,5-b]pyridine To a solution of the product of step 4 (25 mg, 0.056 mmol) in dry pyridine (0.5 mL) was added 4-pyrrolidinopyridine (16 mg, 2 equiv) and butyl chloroformate (0.100 mL, 10 equiv). The mixture was stirred at rt overnight. The next day the reaction was quenched with MeOH (0.25 mL) and stirred for an additional 1 h. The solvent was removed in vacuo and the residue was taken up in EtOAc and washed with 10% citric acid, H$_2$O and brine. The organic was dried with anhydrous MgSO$_4$ and concentrated in vacuo. The titled product was purified by chromatotron eluting with 100:10:1 (CH$_2$Cl$_2$/MeOH/NH$_4$OH). Rf=0.39 (80:10:1 CHCl$_3$/MeOH/NH$_4$OH).

$^1$H NMR (400 MHz, CD$_3$OD) δ0.81 (t, 3H), 1.16 (m, 2H), 1.22 (t, 3H), 1.33 (t, 3H), 1.37 (m, 2H), 2.58 (s, 3H), 2.61 (s, 3H), 2.67 (q, 2H), 2.91 (q, 2H), 3.75 (t, 2H), 5.58 (s, 2H), 7.01 (s, 1H), 7.02 (s, 1H), 7.10 (d, 2H), 7.31 (d, 3H), 8.01 (d, 1H).

EXAMPLE 19

5,7-dimethyl-2-ethyl-3[[2'-(N-butyloxycarbonylaminosulfonyl)-5'-n-propyl[1,1'-biphenyl]-4-yl]methylimidazo[4,5-b]pyridine Step 1: Preparation of 4-n-propylbenzene-t-butylsulfonamide (Scheme 27, compound 94, R$^{21}$=n-pr).

To a solution of 4-n-propylphenylsulfonyl chloride (Lancaster) in anhydrous CH$_2$Cl$_2$ (0.5M solution) cooled to 0° C. under N$_2$ was added t-butylamine (2.2 equiv) slowly through a dropping funnel. After complete addition, the reaction was stirred at rt for 12 h. The CH$_2$Cl$_2$ was removed under reduced pressure and the residue was extracted into Et$_2$O and washed with 2N NaOH, H$_2$O and brine. The organic was dried over anhydrous MgSO$_4$ and concentrated in vacuo to afford the titled product. Rf=0.46 (3:1 Hex/EtOAc).

$^1$H NMR (200 MHz, CDCl$_3$) δ0.93 (t, 3H), 1.22 (s, 9H), 1.62 (m, 2H), 2.65 (t, 2H), 4.67 (bs, 1H), 7.27 (d, 2H), 7.79 (d, 2H).

Step 2: Preparation of 2-t-butylsulfonamido-5-n-propylphenylboric acid (Scheme 27, compound 95, R$^{2a}$=n-pr).

To a solution of 4-n-propylphenyl-t-butylsulfonamide (2.85 g, 11.2 mmoL) in anhydrous THF (20 mL) cooled to −40° C. under N$_2$ was added 2.5M n-BuLi solution (11.2 mL, 2.5 equiv). The mixture was warmed to rt and stirred for 2 h. To the mixture, containing the bright red dianion at 0° C., was added B(OiPr)$_3$ (3.9 mL, 1.5 equiv). The next day 2N HCl (3 mL) was added and the mixture was stirred for 1 h. The solvent was removed under reduced pressure and the residue was extracted with EtOAc. The organic was washed with 2N HCl, H$_2$O and brine. The organic was dried over anhydrous MgSO$_4$ and concentrated in vacuo to afford the titled compound. Rf=0.5 (1:1 EtOAc/Hex). The crude material was used in subsequent steps without further purification.

Step 3: Preparation of 5,7-dimethyl-2-ethyl-3[[2'-(N-t-butylsulfonamido)-5'-n-propyl-[1,1'-biphenyl]-4-yl]methylimidazo[4,5-b]pyridine (Scheme 27, compound 97, R$^{2a}$=n-pr).

To a solution of 5,7-dimethyl-2-ethyl-3-[[4-bromo]-phenyl]methylimidazo[4,5-b]pyridine (6.0 g, 17.4 mmol) and the product of step 2 (11.2 g, 37.3 mmol) in toluene (230 mL) was added 1.25N NaOH (58 mL), EtOH (160 mL) and Pd(PPh$_3$)$_4$ (1.25 g, 3 mol %). The reaction mixture was stirred at 100° C. under N$_2$ for 2 h. The solvent was removed under reduced pressure and the residue was taken up in EtOAc. The organic was washed with 1N NaOH, H$_2$O and brine and dried over anhydrous MgSO4 and concentrated in vacuo. The titled product was recrystallized from EtOAc/Hex. Rf=0.5 (2:1 EtOAc/Hex).

$^1$H NMR (400 MHz, CD$_3$OD) δ0.93 (t, 3H), 0.95 (s, 9H), 1.32 (t, 3H), 1.67 (m, 2H), 2.58 (s, 3H), 2.61 (s, 3H), 2.66 (t, 2H), 2.91 (q, 2H), 5.61 (s, 2H), 7.03 (s, 1H), 7.09 (d, 1H), 7.18 (d, 2H), 7.32 (dd, 1H), 7.41 (d, 2H), 7.97 (d, 1H).

Step 4: Preparation of 5,7-dimethyl-2-ethyl-3[[2'-(sulfonamido)-5'-n-propyl[1,1'-biphenyl]-4-yl]methylimidazo[4,5-b]pyridine (Scheme 27, compound 98, $R^{2a}$=n-pr).

To a mixture of the product of step 3 (945 mg, 1.82 mmol) and anisole (0.5 mL) was added TFA (5 mL). After standing at rt for 24 h, the mixture was concentrated in vacuo. The residue was taken up in EtOAc and washed with 2N $Na_2CO_3$ solution, $H_2O$ and brine. The organic was dried over anhydrous $MgSO_4$ and concentrated in vacuo. The titled product, crystallized from Hex/$Et_2O$, was obtained as a white powder. Rf=0.29 (2:1 EtOAc/Hex).

Step 5: Preparation of 5,7-dimethyl-2-ethyl-3[[2'-(N-butyloxycarbonylaminosulfonyl)-5'-n-propyl[1,1'-biphenyl]-4-yl]methylimidazo[4,5-b]pyridine To a solution of the product of step 4 (56 mg, 0.121 mmol) in dry pyridine (2 mL) was added a catalytic amount of 4-pyrrolidinopyridine and butyl chloroformate (0.164 mL, 10 equiv). The mixture was stirred at rt overnight. The next day the reaction was quenched with MeOH (0.25 mL) and stirred for an additional 1 h. The solvent was removed in vacuo and the residue was taken up in EtOAc and washed with 10% citric acid, $H_2O$ and brine. The organic was dried with anhydrous $MgSO_4$ and concentrated in vacuo. The titled product was purified by flash chromatography eluting with 80:10:1 ($CH_2Cl_2$/MeOH/$NH_4OH$). Rf=0.6 (40:10:1 $CHCl_3$/MeOH/$NH_4OH$).

$^1$H NMR (400 MHz, $CD_3OD$) δ0.80 (t, 3H), 0.94 (t, 3H), 1.14 (m, 2H), 1.34 (t, 3H), 1.37 (m, 2H), 1.67 (m, 2H), 2.58 (s, 3H), 2.61 (s, 3H), 2.67 (t, 2H), 2.92 (q, 2H), 3.89 (t, 2H), 5.60 (s, 2H), 7.03 (s, 1H), 7.10 (d, 1H), 7.12 (d, 2H), 7.24 (d, 2H), 7.37 (dd, 1H), 8.03 (d, 1H).

EXAMPLE 20

5,7-dimethyl-2-ethyl-3[[2'-(N-benzyloxycarbonylaminosulfonyl-5'-ethyl[1,1'-biphenyl]-4-yl]methylimidazo[4,5-b]pyridine To a solution of the product of Example 18, step 4 (20 mg, 0.036 mmol) in dry pyridine (0.5 mL) was added 4-pyrrolidinopyridine (20 mg) and CBz-chloride (0.011 mL, 1.5 equiv). After stirring for 2.5 days, MeOH (0.2 mL) was added and the mixture stirred for an additional 1 h. The solvent was removed and the residue was taken up in EtOAc and washed with 10% citric acid solution, $H_2O$ and brine. The organic was dried over anhydrous $MgSO_4$ and concentrated in vacuo. The titled product was purified by chromatotron eluting with 100:10:1 ($CH_2Cl_2$/MeOH/$NH_4OH$). Rf=0.40 (80:10:1 $CHCl_3$/MeOH/$NH_4OH$).

$^1$H NMR (400 MHz, $CD_3OD$) δ1.23 (t, 3H), 1.31 (t, 3H), 2.57 (s, 3H), 2.62 (s, 3H), 2.69 (q, 2H), 2.88 (q, 2H), 4.84 (s, 2H), 5.55 (s, 2H), 7.00 (comp m, 5H), 7.08–7.14 (comp m, 3H), 7.19 (m, 3H), 7.31 (d, 1H), 8.01 (d, 1H).

EXAMPLE 21

5,7-dimethyl-2-ethyl-3[[2'-(N-benzyloxycarbonylaminosulfonyl)-5'-n-propyl-[1,1'biphenyl]-4-yl]methylimidazo[4,5-b]pyridine To a solution of the product of Example 19, step 4 (40 mg, 0.087 mmol) in dry pyridine (0.5 mL) was added 4-pyrrolidinopyridine (38 mg) and CBz-chloride (0.037 mL, 3.0 equiv). The reaction was stirred for 2 days and then quenched with MeOH (0.25 mL). After stirring for an additional 30 min, the solvent was removed. The residue was dissolved in EtOAc and washed with 10% citric acid solution, $H_2O$ and brine. The organic was dried over anhydrous $MgSO_4$ and brine. The titled compound was purified by chromatotron eluting with 100:10:1 ($CH_2Cl_2$/MeOH/$NH_4OH$). Rf=0.43 (80:10:1 $CHCl_3$/MeOH/$NH_4OH$).

$^1$H NMR (400 MHz, $CD_3OD$) δ0.93 (t, 3H), 1.30 (t, 3H), 1.63 (m, 2H), 2.57 (s, 3H), 2.61 (s, 3H), 2.63 (t, 2H), 2.87 (q, 2H), 4.82 (s, 2H), 6.97 (d, 1H), 7.01 (d, 2H), 7.03 (s, 1H), 7.12 (m, 2H), 7.15–7.21 (comp m, 5H), 7.28 (dd, 1H), 8.00 (d, 1H).

EXAMPLE 22

5,7-dimethyl-2-ethyl-3[[2'-(N-ethoxyethoxycarbonylaminosulfonyl)-5'-n-propyl-[1,1'-biphenyl]-4-yl]methylimidazo[4,5-b]pyridine A solution of the product of Example 19, step 5 (46 mg, 0.073 mmol) in dry ethoxyethanol (2 mL) was stirred in a sealed tube at 100° C. for 4 h. The solvent was removed and the titled compound was purified by chromatotron eluting with 100:10:1 ($CH_2Cl_2$/MeOH/$NH_4OH$). Rf=0.36 (80:10:1 $CHCl_3$/MeOH/$NH_4OH$).

$^1$H NMR (400 MHz, $CD_3OD$) δ0.93 (t, 3H), 1.06 (t, 3H), 1.33 (t, 3H), 1.63 (m, 2H), 2.58 (s, 3H), 2.61 (s, 3H), 2.63 (t, 2H), 2.92 (q, 2H), 3.39 (m, 4H), 3.91 (t, 2H), 5.58 (s, 2H), 7.01 (s, 2H), 7.10 (d, 2H), 7.30 (t, 3H), 8.02 (d, 1H).

The following Examples, shown in Table H, were prepared using procedures described in the Examples 18–22 and illustrated in Schemes 27 through 30.

TABLE H

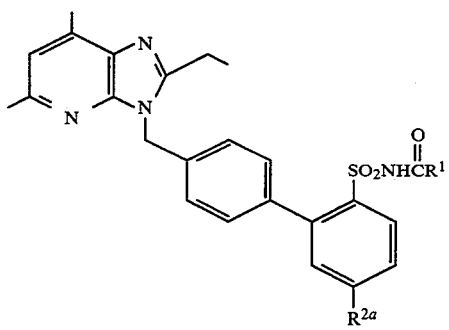

| EX. | R¹ | R² | Precursor (2) | R¹CO₂H/R¹COCl | Rf | (sol) |
|---|---|---|---|---|---|---|
| 23 | O(CH₂)₃CH₃ | CH₂N(CH₂CH₂)₂ | # | CH₃(CH₂)₃OCOCl | 0.31 | (1) |
| 24 | O(CH₂)₃CH₃ | CH(CH₃)₂ | * | CH₃(CH₂)₃OCOCl | 0.43 | (1) |
| 25 | O(CH₂)₃CH₃ | CH₂N(CH₃)2 | # | CH₃(CH₂)₃OCOCl | 0.28 | (1) |
| 26 | O(CH₂)₃CH₃ | CH₂SCH₃ | † | CH₃(CH₂)₃OCOCl | 0.40 | (1) |
| 27 | O(CH₂)₃CH₃ | Ph | @ | CH₃(CH₂)₃OCOCl | 0.38 | (1) |

\* Precursor 2 (Scheme 27) was prepared from a commercially available benzenesulfonyl chloride.
\# Precursor 2 was prepared using the procedure illustrated in Scheme 28, D.
† Precursor 2 was prepared using the procedure illustrated in Scheme 28, E.
@ Precursor 2 was prepared using the procedure illustrated in Scheme 28, B.
(1) (80:10:1 CHCl₃/MeOH/NH₄OH).

EXAMPLE 28

2-Butyl-3-[[2'-(N-butoxycarbonylaminosulfonyl)[1,1'-biphenyl]-4-yl]methyl]-6-[(1-oxopentyl)amino]-5-methyl-3H-imidazo[4,5-b]pyridine Step 1: Preparation of 2-amino-3,5-dinitro-6-methylpyridine To a stirred solution of 2-amino-3-nitro-6-methylpyridine (8.5 g, 55 mmol) in conc. H₂SO₄ (100 mL) at 0° C. was added HNO₃ (2.74 mL, d=1.49, 58.3 mmol) dropwise over 10 min. The mixture was warmed to r.t. for 30 min then heated to 50° C. for 90 min. The reaction mixture was cooled and poured into 200 g of ice. The resulting percipitate was filtered and air dried to give 2-amino-3,5-dinitro-6-methylpyridine as a yellow solid.

Step 2: Preparation of 6-[(1-oxopentyl)amino]-2-butyl-5-methylimidazo[4,5-b]pyridine A mixture of 2-amino-3,5-dinitro-4-methylpyridine (5.2 g, 26 mmol), THF (100 mL), methanol (1300 mL) and Raney-nickel (3 mL of a 1:1 suspension in H₂O) was stirred under H₂ (1 atm.) for 5 h. The mixture was quickly filtered into a flask containing 3 ml of conc. HCl and the solvent was removed in vacuo at r.t. To the resulting crude 2,3,5-triamino-6-methylpyridine HCl complex was added valeric acid (8.68 mL, 80 mmol) and polyphosphoric acid (100 mL) and this mixture was heated to 80° C. for 7 h. The warmed mixture was poured into stirred ice-H₂O (500 mL) and this mixture was cooled and neutralized (to pH 3) by the addition of conc. NH₄OH. Extraction with CH₂Cl₂ (5×50 mL), drying (Na₂SO₄), concentration and purification (SiO2, 5% MeOH/EtOAc) gave the title compound as a solid.

Step 3: 2-Butyl-3-[[2'-(N-butoxycarbonylaminosulfonyl)[1,1'-biphenyl]-4-yl]methyl]-6-[(butoxycarbonyl)amino]-5-methyl-3H-imidazo[4,5-b]pyridine 6-[(1-oxopentyl)amino]-2-butyl-5-methylimidazo[4,5-b]pyridine was converted to the title compound by the method outlined in Example 16 steps 3 to 5. FAB MS (C₃₄H₄₃N₅SO₅) M⁺+1=634.

EXAMPLE 29

2-Butyl-3-[[2'-(N-benzyloxycarbonylaminosulfonyl)[1,1'-biphenyl]-4-yl]methyl]-6-[(1-oxopentyl)amino]-5-methyl-3H-imidazo[4,5-b]pyridine The title compound was prepared as described in Example 28 substituting the reagent benzyl chloroformate for butyl chloroformate in Step 5. FAB MS for C₃₇H₄₁N₅SO₅: M⁺+1=668.

EXAMPLE 30

7-methyl-2-propyl-3-[[2'-(N-butyloxycarbonylaminosulfonyl)[1,1'-biphenyl-4-yl]methyl]-6-[(1-oxobutylamino)]-3H-imidazo[4,5-b]pyridine Step 1: Preparation of 2-amino-3,5-dinitro-4-methylpyridine To a stirred solution of 2-amino-3-nitro-4-methylpyridine (25.6 g, 167 mmol) in conc. H₂SO₄ (100 mL) at 0° C. was added HNO₃ (7.77 mL, d=1.49) dropwise over 30 min. The mixture was warmed to r.t. for 20 min then heated to 45° C. for 90 min. The reaction mixture was cooled and poured into 500 g of ice. The resulting percipitate was filtered and air dried to give 2-amino-3,5-dinitropyridine as a yellow solid.

Step 2: Preparation of 6-[(1-oxobutyl)amino]-2-propyl-7-methylimidazo[4,5-b]pyridine A mixture of 2-amino-3,5-dinitro-4-methylpyridine (3.1 g, 15.6 mmol), THF (100 mL), methanol (100 mL) and Raney-nickel (6 mL of a 1:1 suspension in H₂O) was stirred under H₂ (1 atm.) for 6 h. The mixture was quickly filtered into a receiving flask containing 3 mL of conc. aqueous HCl, and the solvent was removed in vacuo at r.t. To the resulting crude 2,3,5-triamino-3-methylpyridine.HCl complex was added butyric acid (4.3 mL, 46.9 mmol) and polyphosphoric acid (100 mL) and this mixture was heated to 85° C. for 10 h. The warmed mixture was poured into stirred ice-H₂O (200 mL) and this mixture was cooled and neutralized (to pH 3) by the addition of conc. NH₄OH. Extraction with CH₂Cl₂ (3×50 mL), drying (Na₂SO₄), and concentration gave the title compound as a solid.

Step 3: Preparation of 7-methyl-2-propyl-3-[[2'-(N-tert-butylaminosulfonyl)[1,1']-biphenyl-4-yl]methyl]-6-[(1-oxobutyl)amino]-3H-imidazo[4,5-b]pyridine A solution of 6-[(1-oxobutyl)amino]-2-propyl-7-methylimidazo[4,5-b]pyridine (1.3 g, 5.0 mmol) and K$_2$CO$_3$ (1.38 g, 10 mmol) in DMF (15 mL) was stirred for 10 min at r.t. The mixture was heated to 50° C. for 3 min, cooled to rt, and 4'-bromomethylbiphenyl-2-tert-butylsulfonamide (1.5 g, 4.0 mmol) was added. The mixture was stirred for 6 h at r.t. then poured into H$_2$O (300 mL) containing 0.5 mL of HOAc. The residue was isolated by filtration, and further purified (SiO$_2$, 4:1 EtOAc/hexanes) to give the title compound as a foam.

Step 4: Preparation of 7-methyl-2-propyl-3-[[2'-(aminosulfonyl)[1,1']-biphenyl-4-yl]methyl]-6-[(1-oxobutyl)amino]-3H-imidazo[4,5-b]pyridine A solution of 7-methyl-2-propyl-3-[2'-(N-tert-butylaminosulfonyl)[1,1']-biphenyl-4-yl]methyl]-6-[(1-oxobutyl)amino]-3H-imidazo[4,5-b]pyridine. (516 mg) in trifluoroacetic acid (30 mL) was stirred at r.t. for 12 h. The mixture was concentrated, dissolved in CH$_2$Cl$_2$ (100 mL) and washed with saturated aqueous Na$_2$CO$_3$. The organic extracts were dried (K$_2$CO$_3$) and concentrated to give the title compound as a solid.

Step 5: Preparation of 7-methyl-2-propyl-3-[[2'-(N-butoxycarbonylaminosulfonyl)[1,1']biphenyl-4-yl]methyl]-6-[(1-oxobutylamino)]-3H-imidazo[4,5-b]pyridine To a mixture of 7-methyl-2-propyl-3-[2'-(aminosulfonyl)[1,1']biphenyl-4-yl]methyl-6-[(1-oxobutyl)amino]-3H-imidazo[4, 5-b]pyridine (60 mg, 0.112 mmol) and 4-dimethyaminopyridine (41 mg) in pyridine (1.5 mL) was added n-butylchloroformate (0.071 mL, 0.56 mmol). After 14 h at r.t., MeOH (1 mL) was added and the mixture was concentrated, dissolved in CH$_2$Cl$_2$ (40 mL), washed with 5% aqueous citric acid (2×20 mL), concentrated, and purified (SiO$_2$, (89:9:1CH$_2$Cl$_2$/MeOH/NH$_4$OH) to give the title compound as a solid.

$^1$H NMR (200 MHz, CD$_3$OD) δ8.16 (s, 1H), 8.12 (d, 1H), 7.52–7.35 (m, 2H), 7.30 (d, 2H, J=8 Hz), 7.19–7.07 (m, 2H), 7.06 (d, 2H, J=8 Hz), 5.53 (s, 2H), 3.76 (t, 2H, J=7 Hz), 2.88 (t, 2H, J=7.8 Hz), 2.54 (s, 3H), 2.42 (t, 2H,), 1.86–1.65 (m, 4H), 1.42–0.93 (m, 10H), 0.78 (t, 3H, J=7 Hz).

EXAMPLE 31

7-methyl-2-propyl-3-[[2'-(N-benzyloxycarbonylaminosulfonyl)[1,1']-biphenyl-4-yl]methyl]-6-[(1-oxobutylamino)]-3H-imidazo[4,5-b]pyridine The title compound was prepared from 7-methyl-2-propyl-3-[2'-(aminosulfonyl)[1,1']-biphenyl-4-yl]methyl-6-[(1-oxobutyl)amino]-3H-imidazo[4,5-b]pyridine as described in Example 30 substituting the reagent benzyl chloroformate for butyl chloroformate in Step 5. FAB MS for C$_{35}$H$_{37}$N$_5$SO$_5$: M++1=640.

EXAMPLE 32

6-[(ethylaminocarbonyl)amino]-7-methyl-2-propyl-3-[[2'(N-butoxycarbonylaminosulfonyl)[1,1']biphenyl-4-yl]methyl]-3H-imidazo[4,5-b]pyridine Step 1: Preparation of 6-amino-7-methyl-2-propyl-3-[[2'-(aminosulfonyl)[1,1']-biphenyl-4-yl]methyl]-3H-imidazo[4,5-b]pyridine A mixture of 7-methyl-2-propyl-3-[2'-(aminosulfonyl)[1,1']biphenyl-4-yl]methyl-6-[(1-oxobutyl)amino]-3H-imidazo[4,5-b]pyridine (180 mg) in 10 mL of MeOH and 1 mL of conc aqueous HCl was heated to 50° C. for 30 h. The MeOH was removed in vacuo and 100 mL of CH$_2$Cl$_2$ was added. The mixture was washed with saturated aqueous NaHCO$_3$ (2×30 mL), dried (Na$_2$SO$_4$), and concentrated to give the title compound as a foam.

Step 2: Preparation of 6-[(ethylaminocarbonyl)amino]-7-methyl-2-propyl-3-[[2'-(aminosulfonyl)[1,1']biphenyl-4-yl]methyl]-3H-imidazo[4,5-b]pyridine.

A mixture of 6-amino-7-methyl-2-propyl-3-[2'-(aminosulfonyl)[1,1']biphenyl-4-yl]methyl-3H-imidazo4,5-b]pyridine (59 mg, 0.11 mmol) in THF (1 mL), DMF (0.5 mL), and triethylamine (0.1 mL) was added ethyl isocyanate (0.022 mL, 0.28 mmol). After 1 h 50 mL of CH$_2$Cl$_2$ was added and the mixture was washed with water followed by brine. The organic layer was concentrated and purified (SiO2, 5% MeOH-EtOAc) to give the title compound as a solid.

$^1$H NMR (200 MHz, CD$_3$OD) δ8.38 (s, 1H), 8.12 (d, 1H), 7.66–7.30 (m, 4H), 7.28–7.15 (m, 3H), 5.54 (s, 2H), 3.33–3.15 (m, 2H), 2.84 (t, 2H, J=7 Hz), 2.52 (s, 3H), 2.83–2.62 (m, 2H), 1.13 (t, 3H, J=8 Hz) 0.96 (t, 3H, J=7 Hz).

Step 3: Preparation of 6-[(ethylaminocarbonyl)amino]-7-methyl-2-propyl-3-[[2'(N-butoxycarbonylaminosulfonyl)[1,1']-biphenyl-4-yl]methyl]-3H-imidazo[4,5-b]pyridine This compound was prepared from 6-[(ethylaminocarbonyl)amino]-7-methyl-2-propyl-3-[2'-(aminosulfonyl)1,1']-biphenyl-4-yl]methyl-3H-imidazo[4,5-b]pyridine by the method described in example 16, Step 5.

$^1$H NMR (200 MHz, CD3OD) δ8.29 (s, 1H), 8.13 (d, 1H), 7.55–7.38 (m, 2H), 7.29 (d, 2H, J=8 Hz), 7.21–7.13 (m, 1H), 7.06 (d, 2H, J=8 Hz), 5.53 (s, 2H), 3.89 (t, 2H, J=6 Hz), 3.22 (q, 2H, J=7 Hz), 2.89 (t, 2H, J=8 Hz), 2.55 (s, 3H), 1.88–1.68 (m, 2H), 1.43–1.38 (m, 2H), 1.22–1.05 (m, 5H), 1.00 (t, 3H, J=7 Hz), 0.79 (t, 3H, J=8 Hz).

EXAMPLE 33

6-[(Butylsulfonyl)amino]-7-methyl-2-propyl-3-[2'(N-butoxycarbonylaminosulfonyl)[1,1']-biphenyl-4-yl]methyl-3H-imidazo[4,5-b]pyridine Step 1: Preparation of 6-[(Butylsulfonyl)amino]-7-methyl-2-propyl-3-[[2'-(aminosulfonyl)[1,1']biphenyl-4-yl]methyl]-3H-imidazo[4,5-b]pyridine To a mixture of 6-amino-7-methyl-2-propyl-3-[2'-(aminosulfonyl)[1,1']biphenyl-4-yl]methyl-3H-imidazo[4,5-b]pyridine (80 mg, 0.15 mmol) in pyridine (0.5 mL) at 0° C. was added butylsulfonyl chloride (0.02 mL, 0.15 mmol). The mixture was stirred for 1 h, then 1 mL of MeOH was added and the mixture was concentrated. Purification (SiO2, 5% MeOH-EtOAc) gave 50 mg of 6-[(Butylsulfonyl)amino]-7-methyl-2-propyl-3-[2'-(aminosulfonyl)[1,1']-biphenyl-4-yl]methyl-3H-imidazo[4,5-b]pyridine as a solid.

$^1$H NMR (200 MHz, CDCl$_3$) δ8.27 (s, 1H), 8.10 (d, 1H), 7.62–7.38 (m, 4H), 7.33–7.18 (m, 3H), 6.78 (s, 1H), 5.51 (s, 2H), 4.45 (s, 2H), 3.11 (t, 2H, J=7.8 Hz), 2.87 (t, 2H, J=7.6 Hz), 2.70 (s, 3H), 2.95–2.70 (m, 4H), 1.58–1.32 (m, 2H), 1.09–0.88 (m, 6H).

Step 2: Preparation of 6-[(Butylsulfonyl)amino]-7-methyl-2-propyl-3-[[2'-(N-butoxycarbonylaminosulfonyl)[1,1']-biphenyl-4-yl]methyl]-3Himidazo[4,5-b]pyridine This compound was prepared by the method described in example 16, Step 5.

¹H NMR (200 MHz, CD3OD) δ8.18 (s, 1H), 8.16 (d, 1H), 7.62–7.45 (m, 2H), 7.29–7.18 (m, 3H), 7.05 (d, 2H, 8 Hz), 5.48 (s, 2H), 3.85 (t, 2H, J=6 Hz), 3.05 (t, 2H, J=7 Hz), 2.84 (t, 2H, J=7 Hz), 2.68 (s, 3H), 1.92–1.68 (m, 4H), 1.52–1.25 (m, 4H), 1.15–0.85 (m, 8H), 0.75 (t, 3H, J=7 Hz).

EXAMPLE 34

6-[Benzoylamino]-7-methyl-2-propyl-3-[[2'(N-butoxycarbonylaminosulfonyl)[1,1']-biphenyl-4-yl]methyl]-3H-imidazo[4,5-b]pyridine Step 1: Preparation of 6-(Benzoylamino)-7-methyl-2-propyl-3-[[2'-(aminosulfonyl)-[1,1']-biphenyl-4-yl]methyl]-3H-imidazo[4,5-b]pyridine To a mixture of 6-amino-7-methyl-2-propyl-3-[2'-(aminosulfonyl)[1,1']-biphenyl-4-yl]methyl-3H-imidazo[4,5-b]pyridine (189 mg, 0.435 mmol) in 14:1 THF/DMF (7.5 mL) at −15° C. was added benzoyl chloride (0.045 mL, 0.392 mmol). The mixture was stirred for 12 h, then 1 mL of MeOH was added and the mixture was o concentrated. Purification (SiO2, 93:3:4 CH2Cl2/MeOH/HOAc) gave the title compound as a solid.

FAB MS ($C_{30}H_{29}N_5SO_3$) M++1=540

Step 2: Preparation of 6-(Benzoylamino)-7-methyl-2-propyl-3-[[2'-(N-butoxycarbonylaminosulfonyl)[1,1']-biphenyl-4-yl]methyl]-3H-imidazo[4,5-b]pyridine The title compound was prepared from 6-(Benzoylamino)-7-methyl-2-propyl-3-[2'-(aminosulfonyl)[1,1']-biphenyl-4-yl]methyl-3H-imidazo[4,5-b]pyridine by the method described in example 16, Step 5.

FAB MS ($C_{35}H_{37}N_5SO_5$) M++1=640.

EXAMPLE 35

6-[(1-oxopropylamino)]-7-methyl-2-ethyl-3-[[2'-(N-butoxycarbonylaminosulfonyl)[1,1']-biphenyl-4-yl]methyl]-3H-imidazo[4,5-b]pyridine Step 1: Preparation of 6-[(1-oxopropyl)amino]-2-ethyl-7-methylimidazo[4,5-b]pyridine The title compound was prepared as described in Example 30 Step 2 using propionic acid in the place of butyric acid.

Step 2: Preparation of 6-[(1-oxopropylamino)]-7-methyl-2-ethyl-3-[[2'-(N-butoxycarbonylaminosulfonyl)[1,1']-biphenyl-4-yl]methyl]-3H-imidazo[4,5-b]pyridine The title compound was prepared as described in Example 30 Steps 2 through 5.

FAB MS for $C_{30}H_{35}N_5O_5S$ M++1=578.

EXAMPLE 36

6-[(benzoylamino)]-7-methyl-2-ethyl-3-[[2'-(N-butoxycarbonylaminosulfonyl)[1,1']-biphenyl-4-yl]methyl]-3H-imidazo[4,5-b]pyridine The title compound was prepared according to the procedures outlined in Example 32 step 1 and Example 34.

FAB MS for $C_{34}H_{35}N_5O_5S$ M++1=626.

EXAMPLE 37

6-[(benzoylamino)]-7-methyl-2-ethyl-3-[[2'-(N-benzyloxycarbonylaminosulfonyl)[1,1']-biphenyl-4-yl]methyl]-3H-imidazo[4,5-b]pyridine The title compound was prepared from 7-methyl-2-ethyl-3-[[2'-(aminosulfonyl)[1,1']-biphenyl-4-yl]methyl]-6-[benzoylamino]-3H-imidazo[4,5-b]pyridine as described in Example 31.

FAB MS for $C_{37}H_{33}N_5SO_5$: M++1=660.

EXAMPLE 38

7-Methyl-6-[(1-oxobutyl)amino]-2-(n-propyl)-3-[[2'-(N-butoxycarbonylaminosulfonyl)-5'-(n-propyl)-[1,1'biphenyl]-4-yl]methyl]-3H-imidazo[4,5-b]pyridine Step 1: Preparation of 7-Methyl-6-[(1-oxobutyl)amino]-2-(n-propyl)-3-[[2'-(N-t-butyl-sulfonamido)-5'-(n-propyl)-[1,1'-biphenyl]-4-yl]methyl]-3H-imidazo[4,5-b]pyridine.

To a solution of 3-[(4-bromophenyl)methyl]-2-(n-propyl)-7-methyl-6-[(oxobutyl)amino]-3H-imidazo[4,5-b]pyridine (200 mg, 0.47 mmol), prepared using the procedures described in scheme 31, and 2-t-butylsulfonamido-5-n-propylphenylboric acid (280 mg, 0.94 mmol) in toluene (6 mL) was added EtOH (4.5 mL), 1.25N NaOH (3 mL) and Pd(PPh3)4 (30 mg). The mixture was stirred under nitrogen at 95° C. for 4 H. The solvent was removed under reduced pressure and the residue was extracted into EtOAc. The organic was washed with 1N NaOH, H2O and brine and then dried over anhydrous MgSO4. The product was purified by radial chromatography eluting with 40:1 (CH2Cl2/MeOH) providing the titled product as a white foam. Rf=0.14 (30:1CH2Cl2/MeOH).

¹H NMR (400 MHz, CD3OD) d 0.92 (t, 3H), 0.96 (s, 9H), 1.01 (t, 3H), 1.06 (t, 3H), 1.63 (m, 2H), 1.79 (m, 4H), 2.45 (t, 2H), 2.54 (s, 3H), 2.62 (t, 2H), 2.91 (t, 2H), 5.61 (s, 2H), 7.09 (d, 1H), 7.12 (d, 2H), 7.32 (dd, 1H), 7.39 (d, 2H), 7.97 (d, 1H), 8.17 (s, 1H).

Step 2: Preparation of 7-Methyl-6-[(1-oxobutyl)amino]-2-(n-propyl)-3-[[2'-(aminosulfonyl)-5'-(n-propyl)-[1,1'-biphenyl]-4-yl]methyl]-3H-imidazo[4,5-b]pyridine.

To a mixture of the product of step 1 (282 mg, 0.47 mmol) and anisole (2 drops) was added TFA (3 mL). After standing at rt for 24 h the TFA was removed under reduced pressure. The residue was dissolved in EtOAc and and washed with 2N Na2CO3, H2O and brine. The organic was dried over anhydrous MgSO4 and concentrated in vacuo. The product was purified by radial chromatography eluting with 35:1 (CH2Cl2/MeOH) providing the titled product as a white foam. Rf=0.09 (30:1 CH2Cl12/MeOH).

Step 3: Preparation of 7-Methyl-6-[(1-oxobutyl)amino]-2-(n-propyl)-3-[[2'-(N-butoxycarbonylaminosulfonyl)-5'-(n-propyl)-[1,1'biphenyl]-4-yl]methyl]-3H-imidazo[4,5-b]pyridine.

To a solution of the product of step 2 (58 mg, 0.11 mmol) in dry pyridine (0.5 mL) was added DMAP (30 mg) and butyl chloroformate (0.140 mL, 10 equiv). After stirring at rt for 2 days, the reaction was quenched with MeOH and concentrated in vacuo. The residue was extracted into EtOAc and washed with 10% citric acid, H2O and brine. The organic was dried over anhydrous MgSO4 and concentrated in vacuo. The product was purified by radial chromatography eluting with 40:1 (CH2Cl2/MeOH) providing the titled product as white solid. Rf=0.22 (30:1 CH2Cl2/MeOH).

¹H NMR (400 MHz, CD3OD) δ0.81 (t, 3H), 0.94 (t, 3H), 1.01 (t, 3H), 1.06 (t, 3H), 1.16 (m, 2H), 1.39 (m, 2H), 1.79 (m, 4H), 2.47 (t, 2H), 2.54 (s, 3H), 2.67 (t, 2H), 2.92 (t, 2H), 3.91 (t, 2H), 5.62 (s, 2H), 7.08 (d, 1H), 7.17 (d, 2H), 7.25 (d, 2H), 7.38 (dd, 1H), 8.03 (d, 1H), 8.18 (s, 1H).

EXAMPLE 39

7-Methyl-6-[(1-oxobutyl)amino]-2-(n-propyl)-3-[[2'-(N-benzyloxycarbonylaminosulfonyl)-5'-(n-propyl)-[1,1'-biphenyl]-4-yl]methyl]-3H-imidazo[4,5-b]pyridine To a solution of the product of step 2, of Example 38, (16.6 mg, 0.03 mmol) in dry pyridine (0.25 mL) was added DMAP (20 mg) and CBzCl (0.043 mL, 10 equiv). After stirring for 2 days, the reaction was quenched with MeOH and the solvent was removed in vacuo. The residue was dissolved in EtOAc and washed with 10% citric acid, $H_2O$ and brine. The organic was dried over anhydrous $MgSO_4$ and concentrated in vacuo. The product was purified by radial chromatography eluting with 40:1 ($CH_2Cl_2$/MeOH) providing the titled product as white solid. Rf=0.41 (15:1 $CH_2Cl_2$/MeOH).

$^1$H NMR (400 MHz, $CD_3OD$) δ0.94 (t, 3H), 1.00 (t, 3H), 1.06 (t, 3H), 1.62 (m, 2H), 1.76 (m, 4H), 2.44 (t, 2H), 2.57 (s, 3H), 2.66 (t, 2H), 2.90 (t, 2H), 4.91 (s, 2H), 5.57 (s, 2H), 6.95–7.07 (comp m, 7H), 7.19–7.22 (comp m, 3H), 7.33 (dd, 1H), 8.01 (d, 1H), 8.18 (s, 1H).

EXAMPLE 40

7-Methyl-6-[(1-oxobutyl)amino]-2-(n-propyl)-3-[[2'-(N-butoxycarbonylaminosulfonyl)-5'-isobutyl-[1,1'biphenyl]-yl]methyl]-3H-imidazo[4,5-b]pyridine The titled compound was prepared by the methods described in Example 38, steps 1 through 3 by substituting 2-t-butylsulfonamido-5-isobutylphenylboric acid for 2-t-butylsulfonamido-5-n-propylphenylboric acid. Rf=0.47 (15:1 $CH_2Cl_2$.MeOH).

$^1$H NMR (400 MHz, $CD_3OD$) δ0.82 (t, 3H), 0.90 (d, 6H), 1.01 (t, 3H), 1.06 (t, 3H), 1.16 (m, 2H), 1.39 (m, 2H), 1.79 (m, 4H), 1.90 (m, 1H), 2.46 (t, 2H), 2.55 (s, 3H), 2.56 (d, 2H), 2.92 (t, 2H), 3.90 (t, 2H), 5.61 (s, 2H), 7.06 (d, 1H), 7.17 (d, 2H), 7.25 (d, 2H), 7.37 (dd, 1H), 8.03 (d, 1H), 8.18 (s, 1H).

EXAMPLE 41

6-[Benzoylamino]-7-methyl-2-propyl-3-[[2'-(N-butyloxycarbonylamino-sulfonyl)-3-fluoro-[1,1'-biphenyl]-4-yl]methyl]-3H-imidazo[4,5-b]pyridine Step 1: Preparation of 6-[(1-oxobutyl)amino)]-7-methyl-2-propyl-imidazo[4,5-b]pyridine.

The titled compound was prepared from 2-amino-3,5-dinitro-4-methylpyridine using the procedure described in step 2 of Example 16 by replacing valetic acid with butyric acid.

Step 2: Preparation of 6-[(1-oxobutyl)amino)]-7-methyl-2-propyl-3-[[1-bromo-3-fluoro-phenyl-4-yl]methyl-]imidazo[4,5-b]pyridine (compound 134 of scheme 34 where $R^{23}=R^6$=n-pr, $R^{7a}$=Me, $R^{7b}$=H, and $R^{3a}$=F).

To a solution of the product of step 1 (319 mg, 1.23 mmol) in anhydrous DMF (8 mL) was added $CsCO_3$ (799 mg, 2.45 mmol) and the mixture was stirred at rt for 1 hr. To this mixture was added 4-bromo-2-fluorobenzyl bromide (348 mg, 1.3 mmol) and the reaction was stirred at rt overnight. The next day the reaction was poured into EtOAc/$H_2O$ and the organic was separated, washed with brine and dried over anhydrous $K_2CO_3$. Purification by flash chromatography eluting with 10:1 (EtOAc/Hex) afforded the titled compound with Rf=0.58 (100% EtOAc).

Step 3: Preparation of 6-amino-7-methyl-2-propyl-3-[[1bromo-3-fluoro-phenyl-4-yl]-methyl]imidazo[4,5-b]pyridine (compound 135 of scheme 34 where $R^6$=n-pr, $R^{7a}$=Me, $R^{7b}$=H, and $R^{3a}$=F).

The product from step 2, dissolved in MeOH (100 mL) and conc HCl (50 mL), was heated at reflux overnight. The solvent was removed under reduced pressure and the residue was dissolved in $CH_2Cl_2$ and $H_2O$ and $K_2CO_3$ was added until pH neutral. The organic was separated, washed with $NaHCO_3$ solution and dried over anhydrous $K_2CO_3$ to afford the titled compound with Rf=0.46 (100% EtOAc).

Step 4: Preparation of 6-(benzoylamino)-7-methyl-2-propyl-3-[[1-bromo-3-fluoro-phenyl-4-yl]methyl-]imidazo[4,5-b]pyridine (compound 136 of scheme 34 where $R^6$=n-pr, $R^{7a}$=Me, $R^{7b}$=H, and $R^{3a}$=F).

A solution of the product of step 3 (3.76 g, 9.96 mmol) in dry THF (75 mL) and $NEt_3$ (1.66 mL, 11.96 mmol) was cooled to −78° C. and PhCOCl (1.05 mL, 9.04 mmol) was added. The reaction was stirred for 0.5 h at −78° C. and for 1 h at rt. The reaction was quenched with a solution of 2% $K_2CO_3$ (100 mL) and extracted with EtOAc. The organic was washed with 5% citric acid solution and brine and dried over anhydrous $Na_2SO_4$ to afford the titled compound with Rf=0.77 (100% EtOAc).

Step 5: Preparation of 6-[benzoylamino]-7-methyl-2-propyl-3-[[2'-(N-tert-butylamino-sulfonyl)-3-fluoro-[1,1'-biphenyl]-4-yl]methyl]-3H-imidazo[4,5-b]pyridine. (compound 137 of scheme 34 where $R^6$=n-pr, $R^{7a}$=Me, $R^{7b}$=H, and $R^{3a}$=F).

The titled compound was prepared from the product of step 4 by palladium catalyzed coupling with 2-t-butylsulfonamido-phenylboric acid (compound 95, $R^{2a}$=H) using the procedure described in step 1 of example 38 and illustrated in scheme 34. Rf=0.44 (30:1 $CH_2Cl_2$/MeOH, 3×'s).

Step 6: Preparation of 6-[benzoylamino]-7-methyl-2-propyl-3-[[2'-(aminosulfonyl)-3-fluoro-[1,1'-biphenyl]-4-yl]methyl]-3H-imidazo[4,5-b]pyridine (compound 138 of scheme 34 where $R^6$=n-pr, $R^{7a}$=Me, $R^{7b}$=H, and $R^{3a}$=F).

The titled compound was prepared from 6-[Benzoylamino]-7-methyl-2-propyl-3-[[2'-(N-tert-butylaminosulfonyl)-3-fluoro-[1,1'-biphenyl]-4-yl]-methyl]-3H-imidazo[4,5-b]pyridine using the procedure described in step 4 of example 19.

Step 7: Preparation of 6-[benzoylamino]-7-methyl-2-propyl-3-[[2'-(N-butyloxy-carbonylaminosulfonyl)-3-fluoro-[1,1'-biphenyl]-4-yl]methyl]-3H-imidazo[4,5-b]pyridine.

The titled compound was prepared from 6-[benzoylamino]-7-methyl-2-propyl-3-[[2'-(aminosulfonyl)-3-fluoro-[1,1'-biphenyl]-4-yl]-methyl]-3H-imidazo[4,5-b]pyridine using the procedure described in step 2 of Example 34. Rf=0.45 (90:10:1 $CH_2Cl_2$/MeOH/$NH_4OH$).

$^1$H NMR (400 MHz, $CD_3OD$) δ0.83 (t, 3H), 1.04 (t, 3H), 1.21 (m, 2H), 1.42 (m, 2H), 1.83 (m, 2H), 2.60 (s, 3H), 2.97 (t, 2H), 3.83 (t, 2H), 5.68 (s, 2H), 6.94 (t, 1H), 7.03 (dd, 1H), 7.21 (dd, 1H), 7.26 (dd, 1H), 7.51–7.62 (comp m, 4H), 8.03 (dd, 2H), 8.13 (dd, 1H), 8.26 (s, 1H).

EXAMPLE 42

5,7-dimethyl-2-ethyl-3[[2'-(N-butyloxycarbonylaminosulfonyl)-3-fluoro-5'-n-propyl-[1,1'-biphenyl]-4-yl]methyl]-3H-imidazo[4,5-b]pyridine The titled compound was prepared from 5,7-dimethyl-2-ethyl-3-[[1-bromo-3-fluoro]phenyl-4-yl]methylimidazo[4,5-b]pyridine (compound 96, $R^{3a}$=F of scheme 27) using the procedures described in the synthesis of example 19.

$^1$H NMR (400 MHz, CD$_3$OD) δ0.79 (t, 3H), 0.95 (t, 3H), 1.12 (m, 2H), 1.32 (m, 2H), 1.37 (t, 3H), 1.68 (m, 2H), 2.57 (s, 3H), 2.61 (s, 3H), 2.67 (t, 2H), 2.93 (q, 2H), 3.88 (t, 2H), 5.65 (s, 2H), 6.72 (t, 1H), 6.92 (d, 1H), 7.03 (s, 1H), 7.13 (d, 1H), 7.17 (dd, 1H), 7.41 (dd, 1H), 8.03 (d, 1H).

FORMULATION EXAMPLES

Typical Pharmaceutical Compositions Containing a Compound of the Invention

A: Dry Filled Capsules Containing 50 mg of Active Ingredient Per Capsule

| Ingredient | Amount per capsule (mg) |
|---|---|
| Compound A-1 | 50 |
| Lactose | 149 |
| Magnesium stearate | 1 |
| Capsule (size No. 1) | 200 |

The Compound A-1 (title compound of Example 11) can be reduced to a No. 60 powder and the lactose and magnesium stearate can then be passed through a No. 60 blotting cloth onto the powder. The combined ingredients can then be mixed for about 10 minutes and filled into a No. 1 dry gelatin capsule, B: Tablet A typical tablet would contain the Compound A-1 (25 mg), pregelatinized starch USP (82 mg), microcrystaline cellulose (82 mg) and magnesium stearate (1 mg).

C: Combination Tablet

A typical combination tablet would contain, for example, a diuretic such as hydrochlorothiazide and consist of the Compound A-1 (7.5 mg), hydrochlorothiazide (50 mg) pregelatinized starch USP (82 mg), microcrystalline cellulose (82 mg) and magnesium stearate (1 mg).

D: Suppository

Typical suppository formulations for rectal administration can contain the Compound A-1 (1–25 mg), butylated hydroxyanisole (0.08–1.0 mg), disodium calcium edetate (0.25–0.5 mg), and polyethylene glycol (775–1600 mg). Other suppository formulations can be made by substituting, for example, butylated hydroxytoluene (0.04–0.08 mg) for the disodium calcium edetate and a hydrogenated vegetable oil (675–1400 mg) such as Suppocire L, Wecobee FS, Wecobee M, Witepsols, and the like, for the polyethylene glycol. Further, these suppository formulations can also include another active ingredient such as another antihypertensive and/or a diuretic and/or an angiotensin converting enzyme and/or a calcium channel blocker in pharmaceutically effective amounts as described, for example, in C above.

E: Injection

A typical injectable formulation would contain the Compound A-1 (5.42 mg), sodium phosphate dibasic anhydrous (11.4 mg) benzyl alcohol (0.01 ml) and water for injection (1.0 ml). Such an injectable formulation can also include a pharmaceutically effective amount of another active ingredient such as another antihypertensive and/or a diuretic and/or an angiotensin converting enzyme inhibitor and/or a calcium channel blocker.

What is claimed is:

1. A compound of structural formula:

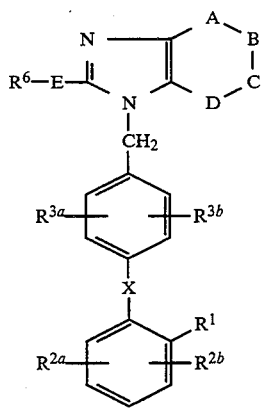
(I)

or a pharmaceutically acceptable salt thereof wherein:
$R^1$ is:

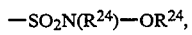 (a)

 (b)

 (c)

 (d)

—SO$_2$NHCN, (e)

—SO$_2$NHCO$_2$R$^{23}$, (f)

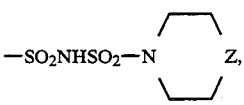 (g)

—NHSO$_2$NHSO$_2$R$^{23}$, (h)

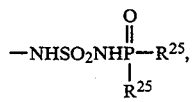 (i)

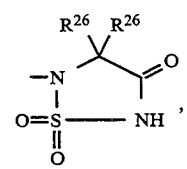 (j)

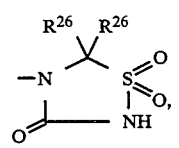 (k)

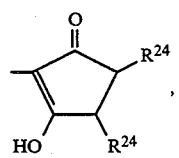 (l)

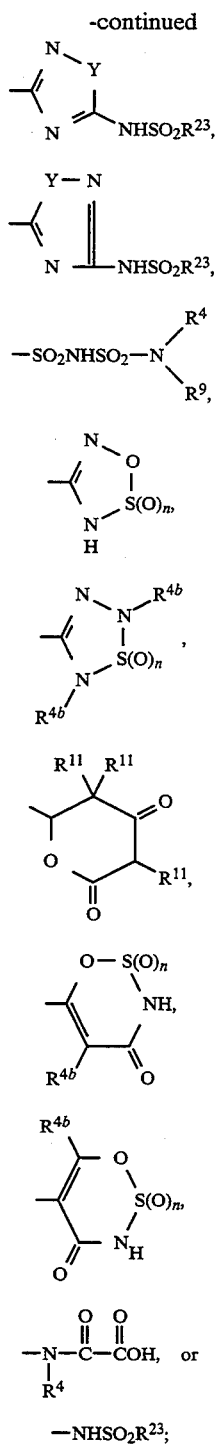

(m), (n), (o), (p), (q), (r), (s), (t), (u), (v)

wherein Y is O or S;

$R^{2a}$ and $R^{2b}$ are independently H, Cl, Br, I, F, —$NO_2$, —$NH_2$, $C_1$-$C_4$-alkylamino, di($C_1$-$C_4$ alkyl)-amino, —$SO_2NHR^9$, $CF_3$, $C_1$-$C_6$-alkyl, or $C_1$-$C_6$-alkoxy, $C_1$-$C_6$-polyfluoroalkoxy $CH_2$—$C_1$-$C_6$-alkoxy, $CH_2$—S—$C_1$-$C_6$-alkyl, $CH_2NR^9R^9$, ($CH_2$)-aryl, wherein aryl is as defined under $R^{3b}$, aryl, wherein aryl is as defined under $R^{3b}$, $C_1$-$C_6$-polyfluoroalkyl, $O(CH_2)_t$-aryl, wherein aryl is as defined under $R^{3b}$, ($CH_2$)$_t$-aryl, wherein aryl is as defined under $R^{3b}$, $O(CH_2)_t$-$C_1$-$C_6$-alkoxy, O-aryl, —$NR^4R^{4b}$, $C_1$-$C_6$-thioalkoxy, $S(O)_s$—($CH_2$)$_t$-aryl, wherein aryl is as defined under $R^{3b}$, $CH_2N(CH_2CH_2)_2O$, $C_1$-$C_6$-alkyl, unsubstituted or substituted with:
$C_1$-$C_3$-alkyl;

s is: 0-2;
t is: 1-3;
$R^{3a}$ is:
(a) H,
(b) Cl, Br, I, or F,
(c) $C_1$-$C_6$-alkyl,
(d) $C_1$-$C_6$-alkoxy, or
(e) $C_1$-$C_6$-alkoxyalkyl;

$R^{3b}$ is:
(a) H,
(b) Cl, Br, I, or F,
(c) $NO_2$,
(d) $C_1$-$C_6$-alkyl,
(e) $C_1$-$C_5$-alkyl-$CO_2$—,
(f) $C_1$-$C_6$-cycloalkyl,
(g) $C_1$-$C_6$-alkoxy,
(h) —$NHSO_2R^4$,
(i) hydroxy $C_1$-$C_4$-alkyl,
(j) aryl-$C_1$-$C_4$-alkyl, wherein aryl is as defined under $R^{3b}$,
(k) $C_1$-$C_4$-alkylthio,
(l) $C_1$-$C_4$-alkyl sulfinyl,
(m) $C_1$-$C_4$-alkyl sulfonyl,
(n) $NH_2$,
(o) $C_1$-$C_4$-alkylamino,
(p) $C_1$-$C_4$-dialkylamino,
(1) fluoro $C_1$-$C_4$-alkyl,
(r) —$SO_2$—$NHR^9$,
(s) aryl, wherein aryl is as defined under $R^{3b}$, or
(t) furyl;

wherein aryl is phenyl or naphthyl or substituted phenyl or naphthyl with one or two substituents selected from the group consisting of Cl, Br, I, F, $C_1$-$C_4$-alkyl, $C_1$-$C_4$-alkoxy, $NO_2$, $CF_3$, $C_1$-$C_4$-alkylthio, OH, $NH_2$, $NH(C_1$-$C_4$-alkyl), $N(C_1$-$C_4$-alkyl)$_2$, $CO_2H$, and $CO_2$—$C_1$-$C_4$-alkyl;

$R^4$ is:
(a) H,
(b) aryl, wherein aryl is as defined above, or
(c) $C_1$-$C_6$-alkyl, unsubstituted or substituted with: aryl, wherein aryl is as defined above, furyl, thienyl, pyridyl, $C_3$-$C_6$-cycloalkyl, and F;

$R^{4a}$ is:
(a) aryl, wherein aryl is as defined above, or
(b) $C_1$-$C_6$-alkyl, substituted or unsubstituted with: aryl, wherein aryl is as defined above, furyl, thienyl, pyridyl, $C_3$-$C_6$-cycloalkyl, and F;

$R^{4b}$ is: H, $C_1$-$C_6$ alkyl, aryl, wherein aryl is as defined above, —$CH_2$-aryl, —CO—$C_1$-$C_6$-alkyl, —CO—$C_3$-$C_6$-cycloalkyl, —CO-aryl, wherein aryl is as defined above, —$CO_2$—$C_1$-$C_6$-alkyl, —$CO_2$—$C_3$-$C_6$-cycloalkyl, —$CO_2$-aryl, wherein aryl is as defined above, —$CONR^4$—$C_1$-$C_6$-alkyl, —$SO_2$-aryl, wherein aryl is as defined above, —$SO_2$—$C_1$-$C_6$-alkyl, —CO-heteroaryl, wherein heteroaryl is as defined below, —$SO_2NR^4$—$C_1$-$C_6$-alkyl, or —$SO_2NR^4$-aryl, wherein aryl is as defined above;

wherein heteroaryl is an unsubstituted, monosubstituted or disubstituted five- or six-membered aromatic ring which contains 1 to 3 heteroatoms selected from the group consisting of O, N or S and wherein the substituents are members selected from the group consisting of —OH, —SH, —$C_1$-$C_4$-alkyl, —$C_1$-$C_4$-alkoxy, Cl, Br, F, I, —NO₂, —CO₂H, —CO₂—C₁-C₄-alkyl, —NH₂, —NH(C₁-C₄-alkyl) and —N(C₁-C₄-alkyl)₂;

R⁵ is:

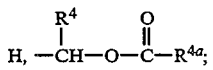

E is: a single bond, —NR¹³(CH₂)$_s$—, —S(O)$_n$—, (CH₂)$_s$— wherein n is 0 to 2 and s is 0 to 5, —CH(OH)—, —O—, or —CO—;

R⁶ is:
(a) C₁-C₉-alkyl, C₂-C₆-alkenyl or C₂-C₆-alkynyl, or substituted C₁-C₉ alkyl, C₂-C₆ alkenyl or C₂-C₆ alkynyl with a substituent selected from the group consisting of aryl as defined above, C₃-C₇-cycloalkyl, Cl, Br, I, F, —OH, —NH₂, —NH(C₁-C₄-alkyl), —CF₂CF₃, —N(C₁-C₄-alkyl)₂, —NH—SO₂R⁴, —COOR⁴, —CF₃, —CF₂CH₃, —SO₂NHR⁹; or
(b) perfluoro-C₁-C₄-alkyl, or
(c) C₃-C₇-cycloalkyl or mono- or disubstituted C₃-C₇-cycloalkyl with a C₁-C₄-alkyl or —CF₃ substituent;

R⁹ is: H, C₁-C₅-alkyl, aryl, or —CH₂-aryl, wherein aryl is as defined above;

R¹⁰ is: H, C₁-C₄-alkyl;

R¹¹ is: H, C₁-C₆-alkyl, C₂-C₄-alkenyl, C₁-C₄-alkoxy-C₁-C₄-alkyl, or

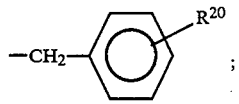

R¹³ is: H, —CO(C₁-C₄-alkyl), C₁-C₆-alkyl, allyl, C₃-C₆-cycloalkyl, phenyl or benzyl;

R¹⁴ is: H, C₁-C₈-alkyl, C₁-C₈-perfluoroalkyl, C₃-C₆-cycloalkyl, phenyl or benzyl;

R¹⁵ is: H or C₁-C₆-alkyl;

R¹⁶ is: H, C₁-C₆-alkyl, C₃-C₆-cycloalkyl, phenyl or benzyl;

R¹⁷ is: —NR⁹R¹⁰, —OR¹⁰, —NHCONH₂, —NHCSNH₂,

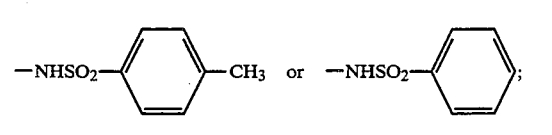

R¹⁸ and R¹⁹ are independently: C₁-C₄-alkyl or taken together are —(CH₂)$_q$— where q is 2 or 3;

R²⁰ is: H, —NO₂, —NH₂, —OH or —OCH₃;

R²³ is:
(a) aryl, wherein aryl is as defined above,
(b) heteroaryl, wherein heteroaryl is as defined above,
(c) C₃-C₄-cycloalkyl,
(d) C₁-C₆-alkyl unsubstituted or substituted with a substituent that is a member selected from the group consisting of: aryl, wherein aryl is as defined above, heteroaryl, wherein heteroaryl is as defined above, —OH, —SH, —C₁-C₄-alkyl, —C₃-C₇-cycloalkyl, —O(C₁-C₆-alkyl), —S(O)$_n$(C₁-C₆-alkyl), —CF₃, Cl, Br, F, I, —NO₂, —CO₂H, —CO₂—C₁-C₄-alkyl, —NH₂, —NH(-C₁-C₄-alkyl), —NHCOR⁴$^a$, —N(C₁-C₄-alkyl)₂, —PO(OH)(C₁-C₄-alkyl), —PO(OH)(aryl), wherein aryl is as defined above, or —PO(OH)-(O—C₁-C₄-alkyl); where n is 0 to 2, or
(e) polyfluoro-C₁-C₆-alkyl, except when R¹ is —NHSO₂R²³;

R²⁴ is:
(a) H,
(b) aryl, wherein aryl is as defined above, or
(c) C₁-C₆-alkyl, unsubstituted or substituted with aryl, wherein aryl is as defined above, F, Cl, Br, —OH, —NH₂, —NH(C₁-C₄-alkyl), —N(C₁-C₄-alkyl)₂, CF₃, O—C₁-C₄-alkyl, or O(CH₂)$_{n+1}$—O—C₁-C₄-alkyl, or
(d) C₃-C₇-cycloalkyl;

R²⁵ is:
(a) aryl unsubstituted or substituted as defined above,
(b) C₁-C₆-alkyl unsubstituted or substituted with aryl, wherein aryl is as defined above, F, Cl, Br, —OH, —NH₂, —NH(C₁-C₄-alkyl), —N(C₁-C₄-alkyl)₂, CF₃, —COOR⁴, or CN;
(c) —CH(R⁴)—O—CO—R⁴$^a$, or
(d) —OH, —O—C₁-C₆-alkyl, wherein alkyl is as defined in (b);

R²⁶ is:
(a) H,
(b) C₁-C₆-alkyl, unsubstituted or substituted with aryl, wherein aryl is as defined above, F, Cl, Br, —OH, —NH₂, —NH(C₁-C₄-alkyl), —N(C₁-C₄-alkyl)₂, CF₃, —COOR⁴, or CN;
(c) F, Cl, Br, or
(d) —O—C₁-C₄-alkyl, wherein alkyl is defined as in (b);

X is

| | |
|---|---|
| a carbon-carbon single bond, | (a) |
| —CO—, | (b) |
| —O—, | (c) |
| —S—, | (d) |
| —N—, R¹³ | (e) |
| —CON—, R¹⁵ | (f) |
| —NCO—, R¹⁵ | (g) |
| —OCH₂—, | (h) |
| —CH₂O—, | (i) |
| —SCH₂—, | (j) |
| —CH₂S—, | (k) |
| —NHC(R⁹)(R¹⁰), | (l) |
| —NR⁹SO₂—, | (m) |
| —SO₂NR⁹—, | (n) |
| —C(R⁹)(R¹⁰)NH—, | (o) |
| —CH=CH—, | (p) |
| —CF=CF—, | (q) |
| —CH=CF—, | (r) |

-continued

—CF=CH—, (s)

—CH₂CH₂—, (t)

—CF₂CF₂—, (u)

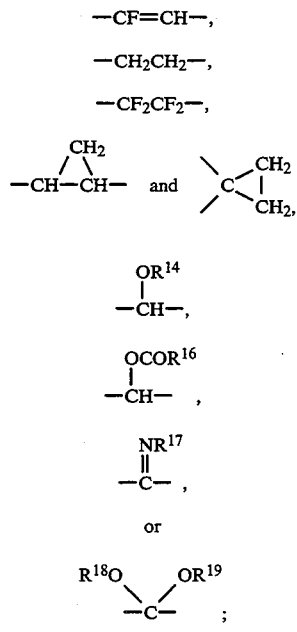 (v)

$$\overset{OR^{14}}{\underset{|}{-CH-}},$$ (w)

$$\overset{OCOR^{16}}{\underset{|}{-CH-}},$$ (x)

$$\overset{NR^{17}}{\underset{|}{\overset{\|}{-C-}}},$$ (y)

or

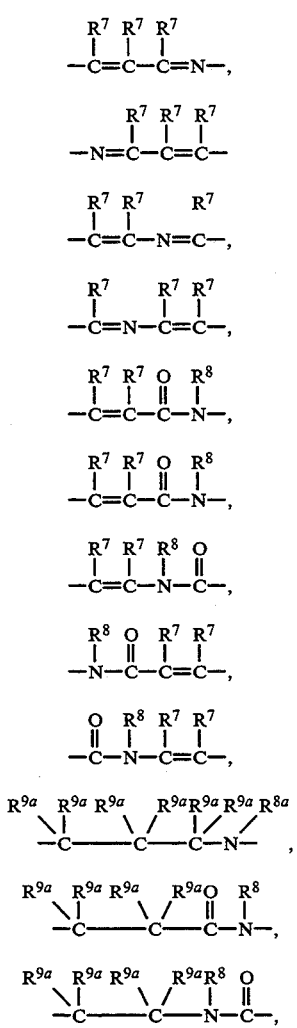 (z)

Z is CH₂, O, NR¹³ or S;
—A—B—C—D— represents:

$$\overset{R^7}{\underset{|}{-C}}=\overset{R^7}{\underset{|}{C}}-\overset{R^7}{\underset{|}{C}}=N-,\quad 1)$$

$$-N=\overset{R^7}{\underset{|}{C}}-\overset{R^7}{\underset{|}{C}}=\overset{R^7}{\underset{|}{C}}-,\quad 2)$$

$$\overset{R^7}{\underset{|}{-C}}=\overset{R^7}{\underset{|}{C}}-N=\overset{R^7}{\underset{|}{C}}-,\quad 3)$$

$$\overset{R^7}{\underset{|}{-C}}=N-\overset{R^7}{\underset{|}{C}}=\overset{R^7}{\underset{|}{C}}-,\quad 4)$$

$$\overset{R^7}{\underset{|}{-C}}=\overset{R^7}{\underset{|}{C}}-\overset{O}{\overset{\|}{C}}-\overset{R^8}{\underset{|}{N}}-,\quad 5)$$

$$\overset{R^7}{\underset{|}{-C}}=\overset{R^7}{\underset{|}{C}}-\overset{O}{\overset{\|}{C}}-\overset{R^8}{\underset{|}{N}}-,\quad 6)$$

$$\overset{R^7}{\underset{|}{-C}}=\overset{R^7}{\underset{|}{C}}-\overset{R^8}{\underset{|}{N}}-\overset{O}{\overset{\|}{C}}-,\quad 7)$$

$$\overset{R^8}{\underset{|}{-N}}-\overset{O}{\overset{\|}{C}}-\overset{R^7}{\underset{|}{C}}=\overset{R^7}{\underset{|}{C}}-,\quad 8)$$

$$\overset{O}{\overset{\|}{-C}}-\overset{R^8}{\underset{|}{N}}-\overset{R^7}{\underset{|}{C}}=\overset{R^7}{\underset{|}{C}}-,\quad 9)$$

$$\overset{R^{9a}}{\underset{|}{-C}}\overset{R^{9a}}{\underset{|}{-}}\overset{R^{9a}}{\underset{|}{C}}\overset{R^{9a}R^{9a}}{\underset{|}{-}}\overset{R^{9a}}{\underset{|}{C}}-\overset{R^{8a}}{\underset{|}{N}}-,\quad 10)$$

$$\overset{R^{9a}}{\underset{|}{-C}}\overset{R^{9a}}{\underset{|}{-}}\overset{R^{9a}}{\underset{|}{C}}\overset{R^{9a}O}{\underset{|}{-}}\overset{R^8}{\underset{|}{C}}-N-,\quad 11)$$

$$\overset{R^{9a}}{\underset{|}{-C}}\overset{R^{9a}}{\underset{|}{-}}\overset{R^{9a}}{\underset{|}{C}}\overset{R^{9a}R^8}{\underset{|}{-}}\overset{O}{\overset{\|}{N-C}}-,\quad 12)$$

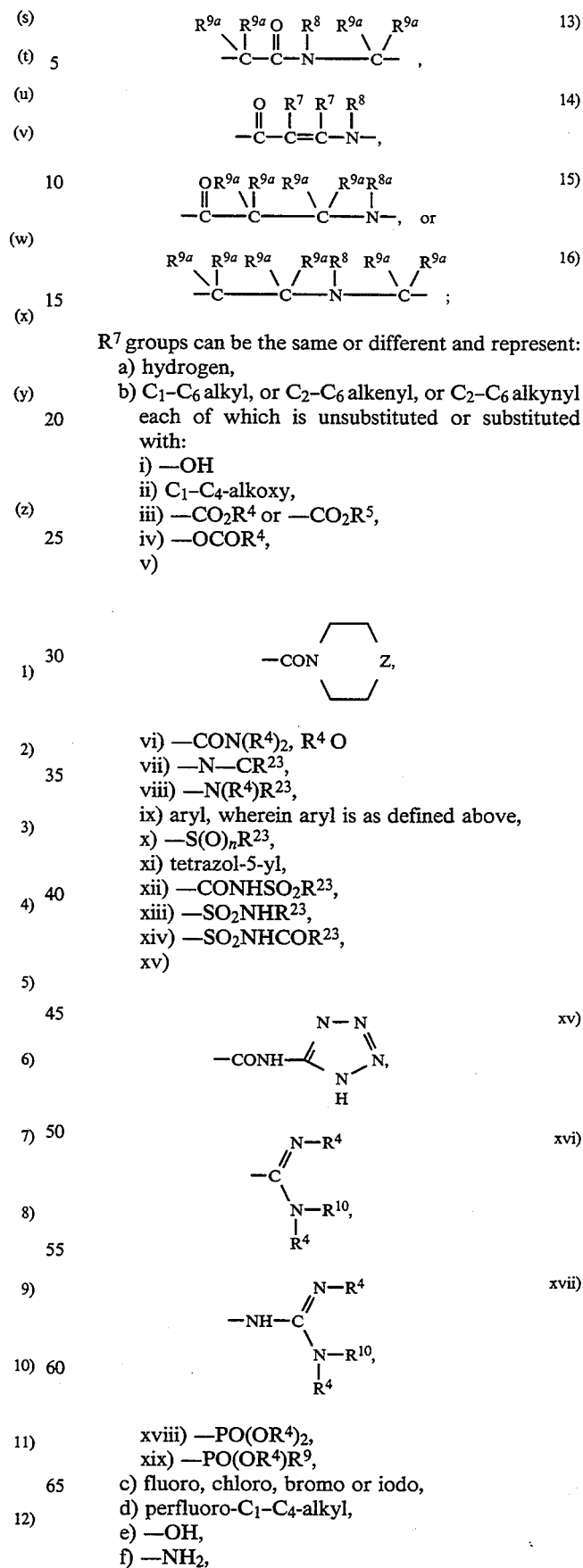

R⁷ groups can be the same or different and represent:
a) hydrogen,
b) C₁-C₆ alkyl, or C₂-C₆ alkenyl, or C₂-C₆ alkynyl each of which is unsubstituted or substituted with:
i) —OH
ii) C₁-C₄-alkoxy,
iii) —CO₂R⁴ or —CO₂R⁵,
iv) —OCOR⁴,
v)

vi) —CON(R⁴)₂, R⁴ O
vii) —N—CR²³,
viii) —N(R⁴)R²³,
ix) aryl, wherein aryl is as defined above,
x) —S(O)ₙR²³,
xi) tetrazol-5-yl,
xii) —CONHSO₂R²³,
xiii) —SO₂NHR²³,
xiv) —SO₂NHCOR²³,
xv)

xviii) —PO(OR⁴)₂,
xix) —PO(OR⁴)R⁹,
c) fluoro, chloro, bromo or iodo,
d) perfluoro-C₁-C₄-alkyl,
e) —OH,
f) —NH₂, g) —N(R⁴)—R²³, h) —N(R⁴)—COR²³, i) —OR²³,
j) —CO₂R⁴ or —CO₂R²³,
k) —CON(R⁴)R²³,
l) —NH—C₃-C₇-cycloalkyl,
m) C₃-C₇-cycloalkyl,
n) aryl, wherein aryl is as defined above,
o) heteroaryl which is a five- or six-membered saturated or unsaturated ring containing up to three heteroatoms selected from the group consisting of O, N or S wherein S may in the form of sulfoxide or sulfone and which may be substituted with one or two substituents which are members selected from the group consisting of Cl, Br, F, I, $C_1$-$C_4$-alkyl, $C_1$-$C_4$-alkoxy, $C_1$-$C_4$—S(O)$_n$—, CF₃, NO₂, OH, CO₂H, CO₂—$C_1$-$C_4$-alkyl, NH₂, NH($C_1$-$C_4$-alkyl), or —N(R⁴)₂;
p) —CN, q) —N(piperidine ring with Z), r) —SO₂N(R⁴)₂;
s) tetrazol-5-yl,
t) —CONHSO₂R²³,
u) —PO(OR⁴)₂,
v) —SO₂NHR²³,
w) —SO₂NHCOR²³,
x) —S(O)$_n$—R²³, y) —CO—N(ring with Z), z) —PO(OR⁴)R⁹ or —PO(OR⁵)R⁹,
aa) —SO₂NHCON(R²³)₂,
bb) —NHSO₂NHR²³,
cc) —NHSO₂NHCOR²³,
dd) —NHCONHSO₂R²³,
ee) —N(R⁴)CO₂R²³, ff) —N(R⁴)—CON(R⁴)—R²³, gg) —CO-aryl, wherein aryl is as defined above, —CO—NH—(tetrazole), ii) —CO—C₁-C₄-alkyl,
jj) —SO₂NH—CN,
kk) —NHSO₂R²³, ll) —C(=NR⁴)—N(R⁴)—R¹⁰, mm) —NH—C(=NR⁴)—N(R⁴)—R¹⁰, nn) —N(R⁴)—CO—N(ring with Z) (with O on C), oo) —N(R⁴)—SO₂—N(ring with Z);

R⁸ groups can be the same or different and represent:
a) hydrogen,
b) $C_1$-$C_6$-alkyl or $C_2$-$C_6$ alkenyl either unsubstituted or substituted with hydroxy, $C_1$-$C_4$-alkoxy, —N(R⁴)₂, —CO₂R⁴, or $C_3$-$C_5$-cycloalkyl, or
c) $C_3$-$C_5$-cycloalkyl;

$R^{8a}$ is: R⁸ or $C_1$-$C_4$-acyl;

$R^{9a}$ groups can be the same or different and represent:
a) hydrogen, or
b) $C_1$-$C_6$-alkyl either unsubstituted or substituted with
i) hydroxy,
ii) —CO₂R⁴,
iii) —CONHR⁴, or
iv) —CON(R⁴)₂.

2. The compound of claim 1, wherein:
R¹ is:

(a) —SO₂N(R²⁴)—OR²⁴, (b) —SO₂NHSO₂R²³, (c) —SO₂NH—P(=O)(R²⁵)₂, (d) —SO₂NHCN, (e) —SO₂NHCO₂R²³, (f) —SO₂NHSO₂—N(ring with Z), (g) —SO₂NHSO₂—N(R⁴)(R⁹), (h) —NHSO₂NHSO₂R²³, (i) —NHSO₂NHP(=O)(R²⁵)₂, (j) 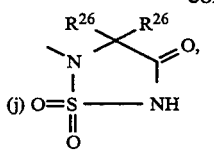

(k) 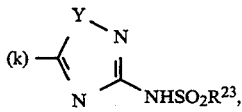

(l) 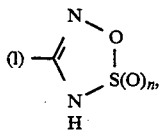

(m) 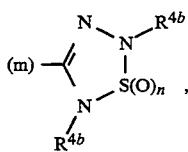

(n) 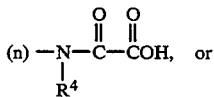 or (o) —NHSO$_2$R$^{23}$;

X is: a single bond;
R$^{2a}$ and R$^{2b}$ are independently:
  a) C$_1$-C$_6$-alkyl,
  b) halogen,
  c) hydrogen,
  d) CH$_2$—C$_1$-C$_6$-alkoxy,
  e) C$_1$-C$_6$-alkoxy,
  f) CH$_2$—S—C$_1$-C$_6$-alkyl,
  g) CH$_2$NR$^9$R$^9$,
  h) 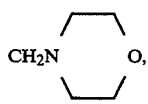
  i) CH$_2$-aryl, wherein aryl is as defined below, or
  j) aryl, wherein aryl is as defined below;
wherein aryl is phenyl or naphthyl or substituted phenyl or naphthyl with one or two substituents selected from the group consisting of Cl, Br, I, F, C$_1$-C$_4$-alkyl, C$_1$-C$_4$-alkoxy, NO$_2$, CF$_3$, C$_1$-C$_4$-alkylthio, OH, NH$_2$, NH(C$_1$-C$_4$-alkyl), N(C$_1$-C$_4$-alkyl)$_2$, CO$_2$H, and CO$_2$—C$_1$-C$_4$-alkyl;

R$^{3a}$ and R$^{3b}$ are independently:
  a) C$_1$-C$_6$-alkyl,
  b) halogen,
  c) C$_1$-C$_6$-alkoxy, or
  d) hydrogen;

R$^4$ is: H, or C$_1$-C$_4$-alkyl;
E is: a single bond or —S—;
R$^6$ is: C$_1$-C$_6$-alkyl, C$_3$-C$_7$-cycloalkyl, C$_2$-C$_6$-alkenyl or C$_2$-C$_6$-alkynyl each of which is either unsubstituted or substituted with C$_1$-C$_4$-alkylthio, C$_1$-C$_4$-alkoxy, CF$_3$, CF$_2$CF$_3$ or -CF$_2$CH$_3$;

A—B—C—D— represents:

1) 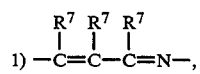

2) 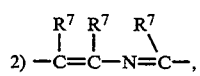

3) 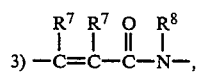

4) 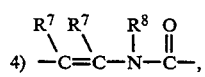

5) 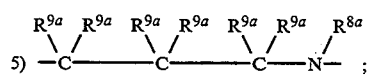

6) —C(R$^{9a}$)—C(R$^{9a}$)—C(R$^{9a}$)—C(=O)—N(R$^8$)— , or

7) —C(R$^{9a}$)—C(R$^{9a}$)—C(R$^{9a}$)—N(R$^8$)—C(=O)—;

R$^7$ groups are the same or different and represent:
  a) hydrogen,
  b) —C$_1$-C$_6$-alkyl, either unsubstituted or substituted with:
    i) OH,
    ii) —CO$_2$R$^4$ or —CO$_2$R$^5$,
    iii) —NH$_2$,
    iv) (C$_1$-C$_4$-alkyl)amino,
    v) di(C$_1$-C$_4$ alkyl)amino,
  c) —F, —Cl, —Br, or —I,
  d) —CF$_3$,
  e) —OH,
  f) —N(R$^4$)R$^{23}$,
  g) —C$_1$-C$_4$-alkoxy,
  h) —CO$_2$R$^4$ or —CO$_2$R$^{23}$,
  i) —CON(R$^4$)R$^{23}$,
  j) —C$_3$-C$_7$-cycloalkyl,
  k) aryl, wherein aryl is as defined above,
  l) heteroaryl, wherein heteroaryl is as defined below,
  m) 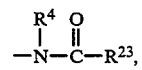

n) —N(R$^4$)CO$_2$R$^{23}$,
  o) 

p) —NHSO$_2$R$^{23}$,
  q) —NHSO$_2$NHR$^{23}$,
  r) —CF$_3$,
  s) tetrazol-5-yl,
  t) —CONHSO$_2$R$^{23}$, u) 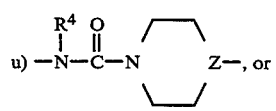 , or v) 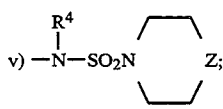

wherein heteroaryl is an unsubstituted, monosubstituted or disubstituted five-or six-membered aromatic ring which contains 1 to 3 heteroatoms selected from the group consisting of O, N or S and wherein the substituents are members selected from the group consisting of —OH, —SH, —C$_1$-C$_4$-alkyl, —C$_1$-C$_4$-alkoxy, Cl, Br, F, I, —NO$_2$, —CO$_2$H, —CO$_2$—C$_1$-C$_4$-alkyl, —NH$_2$, —NH(C$_1$-C$_4$-alkyl) and —N(C$_1$-C$_4$-alkyl)$_2$;

R$^8$ groups are the same or different and represent,
a) hydrogen,
b) C$_1$-C$_4$-alkyl either unsubstituted or substituted with —OH or —CO$_2$R$^4$;

R$^{8a}$ represents
a) hydrogen,
b) C$_1$-C$_4$ alkyl, or
c) (C$_1$-C$_4$-alkyl)CO—; and R$^{9a}$ groups are the same or different and represent:
a) hydrogen,
b) C$_1$-C$_4$-alkyl.

3. The compound of claim 2 wherein:
R$^1$ is:

(a) —SO$_2$N(R$^{24}$)—OR$^{24}$, (b) —SO$_2$NHSO$_2$R$^{23}$, (c) 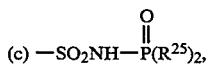

(d) —SO$_2$NHCN, (e) —SO$_2$NHCO$_2$R$^{23}$, (f) 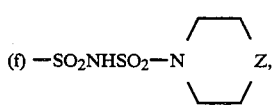

(g) 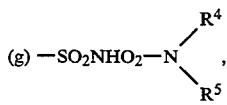

(h) —NHSO$_2$NHSO$_2$R$^{23}$, (i) 

(j) 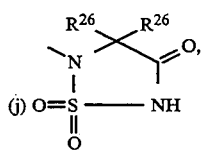

(k) 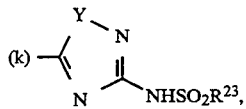

(l) 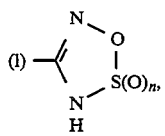

(m) 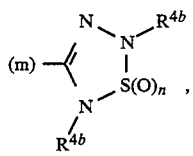

(n) 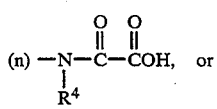

(o) —NHSO$_2$R$^{23}$;

E is a single bond; and,
A—B—C—D represents:

1) 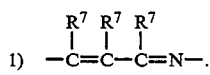

4. The compound of claim 2 of the Formula (II)

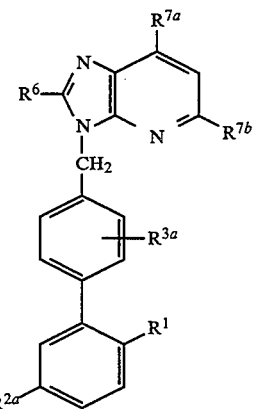

(II)

wherein:
R$^1$ is:

(a) —SO$_2$N(R$^{24}$)—OR$^{24}$, (b) —SO$_2$NHSO$_2$R$^{23}$, (c) 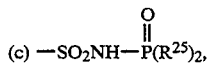

(d) —SO$_2$NHCN, (e) —SO$_2$NHCO$_2$R$^{23}$, (f) 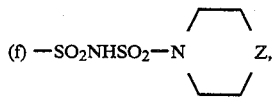

(g) 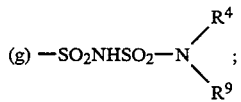

-continued (h) —NHSO$_2$NHSO$_2$R$^{23}$,

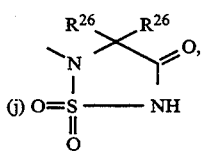
(i) —NHSO$_2$NHP(R$^{25}$)$_2$,

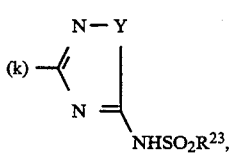
(j)

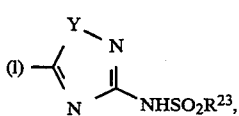
(k)

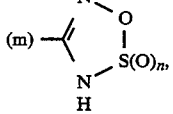
(l)

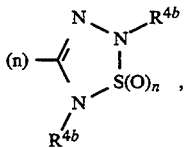
(m)

(n) 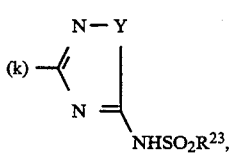

(o) —NHSO$_2$R$^{23}$;

R$^{2a}$ is:
  (a) H,
  (b) C$_1$–C$_6$-alkyl,
  (c) C$_1$–C$_6$-alkoxy,
  (d) CH$_2$—C$_1$–C$_6$-alkoxy,
  (e) CH$_2$—S—C$_1$–C$_6$-alkyl,
  (f) CH$_2$NR$^9$R$^9$, or
  (g)

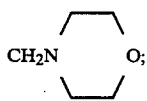

and
R$^{3a}$ is:
  (a) H, or
  (b) Cl, Br, I, or F;
R$^6$ is C$_1$–C$_6$-alkyl or C$_2$–C$_6$-alkenyl or C$_3$–C$_7$-cycloalkyl; and
R$^{7a}$ and R$^{7b}$ independently are:
  (a) hydrogen,
  (b) C$_1$–C$_6$ alkyl or C$_2$–C$_6$ alkenyl,
  (c) —CO$_2$R$^4$ or —CO$_2$R$^{23}$,
  (d) —CON(R$^4$)R$^{23}$, or
  (e) —NR$^4$R$^{4b}$.

5. The compound of claim 4 wherein:
R$^1$ is:
  (a) —SO$_2$N(R$^{24}$)—OR$^{24}$, (b) —SO$_2$NHSO$_2$R$^{23}$, (c) —SO$_2$NH—P(R$^{25}$)$_2$, (with O double-bonded to P)

(d) —SO$_2$NHCN, (e) —SO$_2$NHCO$_2$R$^{23}$, (f) —SO$_2$NHSO$_2$—N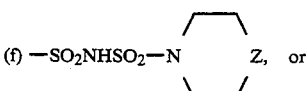Z, or (g) —SO$_2$NHSO$_2$—N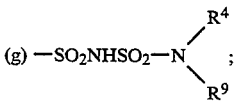R$^4$, R$^9$;

R$^{2a}$ is:
  (a) H,
  (b) C$_1$–C$_6$-alkyl, or
  (c) CH$_2$—C$_1$–C$_6$-alkoxy;
R$^6$ is C$_1$–C$_6$-alkyl; and
R$^{7a}$ and R$^{7b}$ independently are hydrogen, C$_1$–C$_6$-alkyl or CO$_2$R$^4$.

6. The compound of claim 2 of Formula (III)

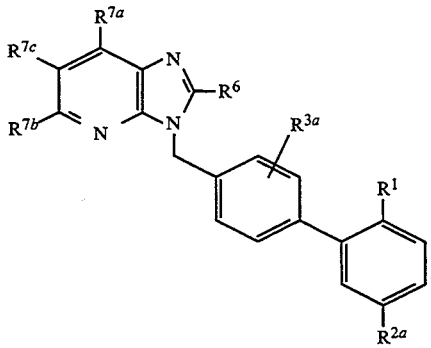

III wherein:
R$^1$ is:

(a) —SO$_2$N(R$^{24}$)—OR$^{24}$, (b) —SO$_2$NHSO$_2$R$^{23}$, (c) —SO$_2$NH—P(R$^{25}$)$_2$, (d) —SO$_2$NHCN, (e) —SO$_2$NHCO$_2$R$^{23}$, (f) —SO$_2$NHSO$_2$—N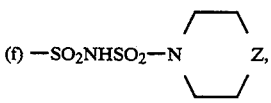Z, (g) —SO$_2$NHSO$_2$—N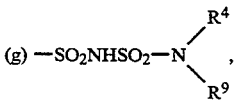R$^4$, R$^9$, (h) —NHSO$_2$NHSO$_2$R$^{23}$, or -continued (i) —NHSO$_2$NHP(R$^{25}$)$_2$;

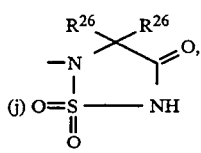
(j)

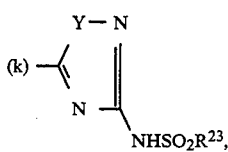
(k)

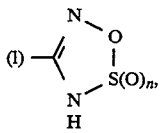
(l)

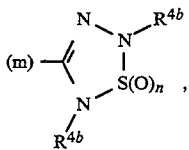
(m)

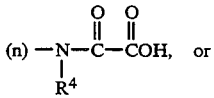
(n) , or (o) —NHSO$_2$R$^{23}$;

R$^{2a}$ is:
(a) H,
(b) C$_1$–C$_6$-alkyl,
(c) C$_1$–C$_6$-alkoxy,
(d) CH$_2$—C$_1$–C$_6$-alkoxy,
(e) CH$_2$—S—C$_1$–C$_6$-alkyl,
(f) CH$_2$NR$^9$R$^9$,
(g)

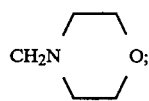

and
R$^{3a}$ is:
(a) H, or
(b) Cl, Br, I, or F; and
R$^6$ is C$_1$–C$_6$-alkyl, C$_2$–C$_6$-alkenyl, —O—C$_1$–C$_4$-alkyl or C$_3$–C$_7$-cycloalkyl; and
R$^{7a}$ and R$^{7b}$ independently are:
(a) hydrogen,
(b) C$_1$–C$_6$ alkyl or C$_2$–C$_6$ alkenyl,
(c) —CO$_2$R$^4$ or —CO$_2$R$^{23}$, or
(d) —CON(R$^4$)R$^{23}$; and
R$^{7c}$ is:

(a) 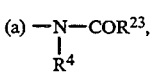

(b) —NHSO$_2$NHR$^{23}$, (c) —N(R$^4$)CO$_2$R$^{23}$, (d) 

(e) —NHSO$_2$R$^{23}$, (f) 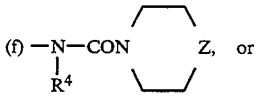 , or (g) 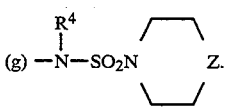

7. The compound of claim 6 wherein:
R$^1$ is:
(a) —SO$_2$NHCO$_2$R$^{23}$,
(b) —SO$_2$NH(R$^{24}$)OR$^{23}$,
(c) —NHSO$_2$R$^{23}$,
(d) —SO$_2$NHSO$_2$R$^{23}$,
(e) —NHSO$_2$NHSO$_2$R$^{23}$
(f) —SO$_2$NHCN, or (g) 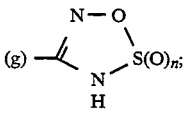

R$^{2a}$ is:
(a) H,
(b) C$_1$–C$_6$-alkyl, or
(c) CH$_2$—C$_1$–C$_6$-alkoxy;
R$^{3a}$ is H or F;
R$^6$ is C$_1$–C$_6$-alkyl; and
R$^{7a}$ and R$^{7b}$ independently are hydrogen, C$_1$–C$_6$-alkyl or CO$_2$R$^4$.

8. The compound of claim 1 or its pharmaceutically acceptable salt selected from the group consisting of:
5,7-dimethyl-2-ethyl-3-[[2'-(3H-1,2,3,5-oxathiadiazole-2-oxide-4-yl)[1,1'-biphenyl]-4-yl]methyl]-3H-imidazo[4,5-b]pyridine,
5,7-dimethyl-2-ethyl-3-[[2'-(N-cyanoaminosulfonyl)[1,1'-biphenyl]-4-yl]methyl]-3H-imidazo[4,5-b]pyridine,
5,7-dimethyl-2-ethyl-3-[[2'-[(N-hydroxyamino)sulfonyl][1,1'-biphenyl]-4-yl]methyl]-3H-imidazo[4,5-b]pyridine,
5,7-dimethyl-2-ethyl-3-[[2'-[phenylsulfonylamino)sulfonyl][1,1'-biphenyl]-4-yl]methyl]-3H-imidazo[4,5-b]pyridine,
2-Ethyl-7-methyl-3-[[2'-(3H-1,2,3,5-oxathiadiazole-2-oxide-4-yl)[1,1'-biphenyl]-4-yl]methyl]-3H-imidazo[4,5-b]pyridine-5-carboxylic acid,
2-Ethyl-7-methyl-3-[[2'-(N-cyanoaminosulfonyl)[1,1'-biphenyl]-4-yl]methyl]-3H-imidazo[4,5-b]pyridine-5carboxylic acid,
2-Ethyl-7-methyl-3-[[2'-[(N-hydroxyamino)sulfonyl][1,1'-biphenyl]-4-yl]methyl]-3H-imidazo[4,5-b]pyridine-5carboxylic acid,
2-Ethyl-7-methyl-3-[[2'-[phenylsulfonylamino)sulfonyl][1,1'-biphenyl]-4-yl]methyl]-3H-imidazo[4,5-b]pyridine-5-carboxylic acid, 5,7-dimethyl-2-ethyl-3-[[2'-[(butyloxycarbonyl)aminosulfonyl]-5'-methyl-[1,1'-biphenyl]-4-yl]methyl]-3H-imidazo[4,5-b]pyridine, 5,7-dimethyl-2-ethyl-3-[[2'-[(benzyloxycarbonyl)aminosulfonyl]-5'-propyl-[1,1'-biphenyl]-4-yl]methyl]-3H-imidazo[4,5-b]pyridine, 5,7-dimethyl-2-ethyl-3-[[2'-[(butyloxycarbonyl)aminosulfonyl]-5'-propyl-[1,1'-biphenyl]-4-yl]methyl]-3H-imidazo[4,5-b]pyridine, 5,7-dimethyl-2-ethyl-3-[[2'-[(butyloxycarbonyl)aminosulfonyl]-5'-(2-methylpropyl)-[1,1'-biphenyl]-4-yl]methyl]-3H-imidazo[4,5-b]pyridine, 5,7-dimethyl-2-ethyl-3-[[2'-[(butyloxycarbonyl)aminosulfonyl]-5'-butyl-[1,1'-biphenyl]-4-yl]methyl]-3H-imidazo[4,5-b]pyridine, 5,7-dimethyl-2-ethyl-3-[[2'-[(butyloxycarbonyl)aminosulfonyl]-5'-benzyl-[1,1'-biphenyl]-4-yl]methyl]-3H-imidazo[4,5-b]pyridine, 5,7-dimethyl-2-ethyl-3-[[2'-[(butyloxycarbonyl)aminosulfonyl]-5'-phenyl-[1,1'-biphenyl]-4-yl]methyl]-3H-imidazo[4,5-b]pyridine, 2-butyl-3-[2'-[(N-butoxycarbonyl)aminosulfonyl][1,1'-biphenyl]-4-yl]methyl-6-[N-(n-pentanoyl)]-3H-imidazo[4,5-b]pyridine, 2-Butyl-3-[[2'-(N-benzyloxycarbonylaminosulfonyl)[1,1'-biphenyl]-4-yl]methyl]-6-[(1-oxopentyl)amino]-5-methyl-3H-imidazo[4,5-b]pyridine, 2-Butyl-3-[[2'-[(3-methylbutyl)oxyaminosulfonyl]][1,1'-biphenyl]-4-yl]methyl]-6-[(1-oxopentyl)amino]-5-methyl-3H-imidazo[4,5-b]pyridine, 7-methyl-2-propyl-3-[[2'-(N-butyloxycarbonylaminosulfonyl)[1,1'-biphenyl]-4-yl]methyl]-6-[(1-oxobutylamino)]-3H-imidazo[4,5-b]pyridine, 7-methyl-2-propyl-3-[[2'-(N-butyloxycarbonylaminosulfonyl)-5'-propyl-[1,1'-biphenyl]-4-yl]methyl]-6-[(1-oxobutylamino)]-3H-imidazo[4,5-b]pyridine, 7-methyl-2-propyl-3-[[2'-(N-butyloxycarbonylaminosulfonyl)-5'-butyl-[1,1'-biphenyl]-4-yl]methyl]-6-[(1-oxobutylamino)]-3H-imidazo[4,5-b]pyridine, 7-methyl-2-propyl-3-[[2'-(N-butyloxycarbonylaminosulfonyl)-5'-(2-methylpropyl)-[1,1'-biphenyl]-4-yl]methyl]-6-[(1-oxobutylamino)]-3H-imidazo[4,5-b]pyridine, 7-methyl-2-propyl-3-[[2'-(N-benzyloxycarbonylaminosulfonyl)[1,1'-biphenyl]-4-yl]methyl]-6-[(1-oxobutylamino)]-3H-imidazo[4,5-b]pyridine, 6-[Benzoylamino]-7-methyl-2-propyl-3-[[2'(N-butyloxycarbonylaminosulfonyl)[1,1'-biphenyl]-4-yl]methyl]-3H-imidazo[4,5-b]pyridine, 6-[(4-Chlorobenzoyl)amino]-7-methyl-2-propyl-3-[[2'(N-butyloxycarbonylaminosulfonyl)[1,1'-biphenyl]-4-yl]methyl]-3H-imidazo[4,5-b]pyridine, 6-[Benzoylamino]-7-methyl-2-propyl-3-[[2'-[N-(3-methylbutyl)oxycarbonylaminosulfonyl][1,1'-biphenyl]-4-yl]methyl]-3H-imidazo[4,5-b]pyridine, 6-[Benzoylamino]-7-methyl-2-ethyl-3-[[2'-(N-butyloxycarbonylaminosulfonyl)[1,1'-biphenyl]-4-yl]methyl]-3H-imidazo[4,5-b]pyridine, 6-[(Benzoylamino)]-7-methyl-2-propyl-3-[[2'-(N-benzyloxycarbonylaminosulfonyl)[1,1'-biphenyl]-4-yl]methyl]-3H-imidazo[4,5-b]pyridine, 7-methyl-2-propyl-3-[[2'-(N-benzyloxycarbonylaminosulfonyl)[1,1'-biphenyl]-4-yl]methyl]-6-[(N-isopropyl-N-methyl)aminocarbonylamino]-3H-imidazo[4,5-b]pyridine, 6-[Benzoylamino]-7-methyl-2-propyl-3-[[2'(N-butyloxycarbonylaminosulfonyl)-3-fluoro-[1,1'-biphenyl]-4-yl]methyl]-3H-imidazo[4,5-b]pyridine, or 5,7-dimethyl-2-ethyl-3-[[2'-[(N-butyloxycarbonyl)aminosulfonyl]-3-fluoro-5'-n-propyl-[1,1'-biphenyl]-4-yl]methyl]-3H-imidazo [4,5-b]pyridine.

9. The compound of claim 1 which is 6-[Benzoylamino]-7-methyl-2-propyl-3-[[2'(N-butyloxycarbonylaminosulfonyl)-3-fluoro-[1,1'-biphenyl]-4-yl]methyl]-3H-imidazo[4,5-b]pyridine.

10. The compound of claim 1 which is 6-[Benzoylamino]-7-methyl-2-propyl-3-[[2'(N-butyloxycarbonylaminosulfonyl)[1,1'-biphenyl]-4-yl]methyl]-3H-imidazo[4,5-b]pyridine.

11. The compound of claim 4 of the Formula II, wherein $R^{3a}$ is defined as a H or 3-F and all other substitutents are as defined in Table A below:

TABLE A

| Compound No. | $R^1$ | $R^6$ | $R^{7a}$ | $R^{7b}$ | $R^{2a}$ |
|---|---|---|---|---|---|
| A1 | —SO$_2$NHOH | Et | Me | Me | n-Pr |
| A2 | —SO$_2$NHSO$_2$Ph | Et | Me | Me | Et |
| A3 | —SO$_2$NHSO$_2$Me | Et | Me | Me | CH$_2$SCH$_3$ |
| A4 | —SO$_2$NHSO$_2$—⟨ | Pr | CO$_2$H | Me | OCH$_3$ |
| A5 | (isoxazole-N-S(=O)-NH-) | Et | Me | Me | Et |
| A6 | (N-Ph diazole-N-S(=O)-NH-) | Et | Me | Me | OEt |
| A7 | —NH—C(=O)—CO$_2$H | Et | CO$_2$H | Me | t-Bu |

TABLE A-continued

| Compound No. | $R^1$ | $R^6$ | $R^{7a}$ | $R^{7b}$ | $R^{2a}$ |
|---|---|---|---|---|---|
| A8 | —SO$_2$NHSO$_2$—$\prec$ | Et | Me | Me | i-Pr |
| A9 | —SO$_2$NHP(O—CH$_2$Ph)$_2$ (P=O) | Et | Me | Me | i-Bu |
| A10 | (cyclic sulfamide with glycyl N—H, S(=O)$_2$) | Et | Me | Me | CH$_2$N(CH$_3$)$_2$ |
| A11 | (isoxazoline with NHSO$_2$Ph) | Et | Me | Me | Et |
| A12 | (cyclic N–O–S(=O)$_2$–NH) | Et | Me | Me | n-Pr |
| A13 | —SO$_2$NHCOOC$_2$H$_5$ | Et | Me | Me | n-Pr |
| A14 | —SO$_2$NHCOOCH$_2$Ph | Et | Me | Me | Et |
| A15 | —SO$_2$NHCOOBu | Et | Me | Me | OEt |
| A16 | —SO$_2$NHCOOCH$_2$c-Pr | Et | Me | Me | CH$_2$SCH$_3$ |
| A17 | —SO$_2$NHOH | Pr | Me | CONH$_2$ | t-Bu |
| A18 | —SO$_2$NHCOO-tBu | Et | Me | COOH | CH$_2$N[CH$_2$CH$_2$]$_2$O |
| A19 | —SO$_2$NHCOO-tBu | Et | Me | Me | i-Bu |
| A20 | —SO$_2$NHCOO—Et | Et | Me | NMe$_2$ | Et |
| A21 | —SO$_2$NHCOO—Bu | Et | Me | COOH | n-Pr |
| A22 | —SO$_2$NHOH | Et | Me | NMe$_2$ | n-Pr |
| A23 | —SO$_2$NHCO2(CH$_2$)$_2$OEt | Et | Me | Me | n-Pr |
| A24 | —SO$_2$NHCO2(CH$_2$)$_2$OEt | Et | Me | Me | i-Bu |
| A25 | —SO$_2$NHCO2(CH$_2$)$_2$OEt | Et | Me | Me | OEt |
| A26 | —SO$_2$NHCO$_2$Bu | Et | Me | Me | OCH$_2$CF$_3$ |
| A27 | —SO$_2$NHCO$_2$CH$_2$Ph | Et | Me | Me | n-Pr |
| A28 | —SO$_2$NHCO$_2$CH$_2$Ph | Et | Me | Me | OEt |
| A29 | —SO$_2$NHCO$_2$CH$_2$Ph | Et | Me | Me | i-Bu |
| A30 | —SO$_2$NHCO$_2$CH$_2$Ph | Et | Me | Me | n-Bu |
| A31 | —SO$_2$NHCO$_2$Bu | Et | Me | Me | Et |
| A32 | —SO$_2$NHOH | Et | Me | Me | H |
| A33 | —SO$_2$NHSO$_2$Ph | Et | Me | Me | H |
| A34 | —SO$_2$NHSO$_2$Me | Et | Me | Me | H |
| A35 | —SO$_2$NHSO$_2$—$\prec$ | Pr | CO$_2$H | Me | H |
| A36 | (cyclic N–O–S(=O)–NH) | Et | Me | Me | H |
| A37 | (cyclic N–N(Ph)–S(=O)–NH) | Et | Me | Me | H |
| A38 | —NH—C(=O)—CO$_2$H | Et | CO$_2$H | Me | H |
| A39 | —SO$_2$NHSO$_2$—$\prec$ | Et | Me | Me | H |
| A40 | —SO$_2$NHP(O—CH$_2$Ph)$_2$ (P=O) | Et | Me | Me | H |

TABLE A-continued

| Compound No. | R[1] | R[6] | R[7a] | R[7b] | R[2a] |
|---|---|---|---|---|---|
| A41 | (structure: -N-CH2-C(=O)- with S(=O)2-NH ring) | Et | Me | Me | H |
| A42 | (structure: N—O ring with -NHSO2Ph) | Et | Me | Me | H |
| A43 | (structure: N-O-S(=O)2-NH ring) | Et | Me | Me | H |
| A44 | —SO2NHCO2Bu | Et | Me | Me | N—Bu |
| A45 | —SO2NHCO2Bu | Et | Me | Me | N—Pr. |

12. The compound of claim 6 of the Formula III:

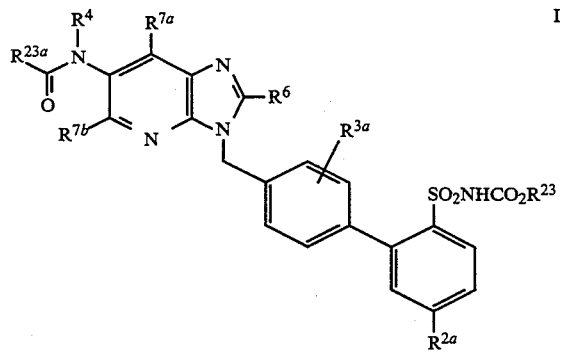

wherein: $R^{7a}$ is H, or Me; and $R^{7b}$ is H, Me, or $CO_2H$; and $R^6$ is Et, Pt, or Bu; and $R^{2a}$ is H, Et, Pr, n-Bu, or i-Bu; and $R^{3a}$ is H or 3-F; and $R^4$ is H, or $CH_3$ and $R^{23}$ and $R^{23a}$ are as defined below in Table B:

TABLE B

| R[23] | R[23a] |
|---|---|
| -n-Pr | -n-Bu |
| -n-Bu | -n-Bu |
| -n-Hexyl | -n-Bu |
| —CH2CH(CH3)2 | -n-Bu |
| —CH2CH2CH(CH3)2 | -n-Bu |
| —CH2CH(CH3)CH(CH3)2 | -n-Bu |
| —CH2(C5H9) | -n-Bu |
| —CH2CH2(C5H9) | -n-Bu |
| —CH2(C6H11) | -n-Bu |
| —CH2CH2(C6H11) | -n-Bu |
| —CH2(C6H5) | -n-Bu |
| —CH2CH2C6H5 | -n-Bu |
| —CH(CH3)CH2CH3 | -n-Bu |
| —CH(CH3)CH2CH2CH3 | -n-Bu |
| —C(CH3)2CH2CH3 | -n-Bu |
| —C(CH3)2CH2CH2CH3 | -n-Bu |
| —CHC(CH3)2 | -n-Bu |
| —CH2CH2OCH3 | -n-Bu |
| —CH2CH2OCH2CH3 | -n-Bu |
| —CH2CH2OCH(CH3)2 | -n-Bu |
| -cyclopropane | -n-Bu |
| 2,2-dimethylcyclopropane-1-yl | -n-Bu |
| -C5H9 | -n-Bu |
| -C6H5 | -n-Bu |
| -C6H11 | -n-Bu |
| —CH2-thiophene-2-yl | -n-Bu |
| —CH2-thiophene-3-yl | -n-Bu |
| —CH2-furan-2-yl | -n-Bu |
| —CH2-furan-3-yl | -n-Bu |
| -n-Pr | Pr |
| -n-Bu | Pr |
| -n-Hexyl | Pr |
| —CH2CH(CH3)2 | Pr |
| —CH2CH2CH(CH3)2 | Pr |
| —CH2(C5H9) | Pr |
| —CH2CH2(C5H9) | Pr |
| —CH2(C6H11) | Pr |
| —CH2CH2(C6H11) | Pr |
| —CH2(C6H5) | Pr |
| —CH2CH2(C6H5) | Pr |
| —CH2CH2OCH3 | Pr |
| -n-Pr | Et |
| -n-Bu | Et |
| -n-Hexyl | Et |
| —CH2CH(CH3)2 | Et |
| —CH2CH2CH(CH3)2 | Et |
| —CH2(C5H9) | Et |
| —CH2CH2(C5H9) | Et |
| —CH2(C6H11) | Et |
| —CH2CH2(C6H11) | Et |
| —CH2(C6H5) | Et |
| —CH2CH2(C6H5) | Et |
| —CH2CH2OCH3 | Et |
| -n-Pr | Ph |
| -n-Bu | Ph |
| -n-Hexyl | Ph |
| —CH2CH(CH3)2 | Ph |
| —CH2CH2CH(CH3)2 | Ph |
| —CH2(C5H9) | Ph |
| —CH2CH2(C5H9) | Ph |
| —CH2(C6H11) | Ph |
| —CH2CH2(C6H11) | Ph |
| —CH2(C6H5) | Ph |
| —CH2CH2(C6H5) | Ph |
| —CH2CH2OCH3 | Ph |
| -n-Bu | -2-pyridyl |
| —CH2(C5H9) | -2-pyridyl |
| -n-Bu | -3-pyridyl |
| —CH2(C5H9) | -3-pyridyl |
| -n-Bu | -4-pyridyl |
| —CH2(C5H9) | -4-pyridyl |
| -n-Bu | -2-thienyl |
| —CH2(C5H9) | -2-thienyl |
| -n-Bu | -2-furyl |
| —CH2(C5H9) | -2-furyl. |

13. The compound of claim 6 of the Formula III:

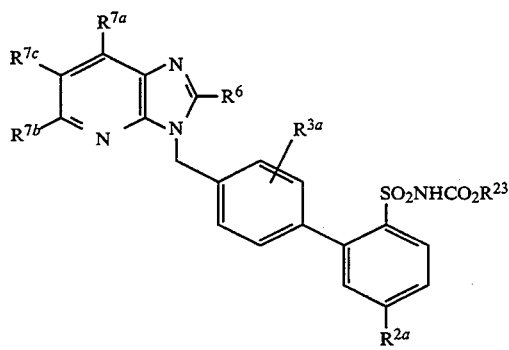

wherein $R^{7a}$ is H, or Me; and $R^{7b}$ is H, Me, or $CO_2H$; and $R^6$ is Et, Pr, or Bu; and $R^{2a}$ is H, Et, Pr, n-Bu, or i-Bu; and $R^{3a}$ is H or 3-F; and $R^4$ is H, or $CH_3$ and $R^{23}$ and $R^{23a}$ are as defined in the table below in Table C:

TABLE C

| $R^{23}$ | $R^{7c}$ |
|---|---|
| -n-Pr | $-NR^4CON(H)$-n-Pr |
| -n-Bu | $-NR^4CON(H)$-n-Pr |
| -n-Hexyl | $-NR^4CON(H)$-n-Pr |
| $-CH_2CH(CH_3)_2$ | $-NR^4CON(H)$-n-Pr |
| $-CH_2CH_2CH(CH_3)_2$ | $-NR^4CON(H)$-n-Pr |
| $-CH_2(C_5H_9)$ | $-NR^4CON(H)$-n-Pr |
| $-CH_2CH_2(C_5H_9)$ | $-NR^4CON(H)$-n-Pr |
| $-CH_2(C_6H_{11})$ | $-NR^4CON(H)$-n-Pr |
| $-CH_2CH_2(C_6H_{11})$ | $-NR^4CON(H)$-n-Pr |
| $-CH_2(C_6H_5)$ | $-NR^4CON(H)$-n-Pr |
| $-CH_2CH_2(C_6H_5)$ | $-NR^4CON(H)$-n-Pr |
| $-CH_2CH_2OCH_3$ | $-NR^4CON(H)$-n-Pr |
| -n-Pr | $-NR^4CON(H)$-i-Pr |
| -n-Bu | $-NR^4CON(H)$-i-Pr |
| -n-Hexyl | $-NR^4CON(H)$-i-Pr |
| $-CH_2CH(CH_3)_2$ | $-NR^4CON(H)$-i-Pr |
| $-CH_2CH_2CH(CH_3)_2$ | $-NR^4CON(H)$-i-Pr |
| $-CH_2(C_5H_9)$ | $-NR^4CON(H)$-i-Pr |
| $-CH_2CH_2(C_5H_9)$ | $-NR^4CON(H)$-i-Pr |
| $-CH_2(C_6H_{11})$ | $-NR^4CON(H)$-i-Pr |
| $-CH_2CH_2(C_6H_{11})$ | $-NR^4CON(H)$-i-Pr |
| $-CH_2(C_6H_5)$ | $-NR^4CON(H)$-i-Pr |
| $-CH_2CH_2(C_6H_5)$ | $-NR^4CON(H)$-i-Pr |
| $-CH_2CH_2OCH_3$ | $-NR^4CON(H)$-i-Pr |
| -n-Pr | $-NR^4CON(Me)$-i-Pr |
| -n-Bu | $-NR^4CON(Me)$-i-Pr |
| -n-Hexyl | $-NR^4CON(Me)$-i-Pr |
| $-CH_2CH(CH_3)_2$ | $-NR^4CON(Me)$-i-Pr |
| $-CH_2CH_2CH(CH_3)_2$ | $-NR^4CON(Me)$-i-Pr |
| $-CH_2(C_5H_9)$ | $-NR^4CON(Me)$-i-Pr |
| $-CH_2CH_2(C_5H_9)$ | $-NR^4CON(Me)$-i-Pr |
| $-CH_2(C_6H_{11})$ | $-NR^4CON(Me)$-i-Pr |
| $-CH_2CH_2(C_6H_{11})$ | $-NR^4CON(Me)$-i-Pr |
| $-CH_2(C_6H_5)$ | $-NR^4CON(Me)$-i-Pr |
| $-CH_2CH_2(C_6H_5)$ | $-NR^4(Me^4CO)$-i-Pr |
| $-CH_2CH_2OCH_3$ | $-NR^4CON(Me)$-i-Pr |
| -n-Bu | $-NR^4CONHMe$ |
| $-CH_2(C_5H_9)$ | $-NR^4CONHMe$ |
| -n-Bu | $-NR^4CONHEt$ |
| $-CH_2(C_5H_9)$ | $-NR^4CONHEt$ |
| -n-Bu | $-NR^4CONMe_2$ |
| $-CH_2(C_5H_9)$ | $-NR^4CONMe_2$ |
| -n-Bu | $-NR^4CONEt_2$ |
| $-CH_2(C_5H_9)$ | $-NR^4CONEt_2$ |
| $-CH_2CH_2OCH_3$ | $-NR^4CONEt_2$ |
| -n-Bu | $-NR^4CO$-morpholine-4-yl |
| $-CH_2(C_5H_9)$ | $-NR^4CO$-morpholine-4-yl |
| -n-Bu | $-NR^4CO$-pyrrolidine-1-yl |
| $-CH_2(C_5H_9)$ | $-NR^4CO$-pyrrolidine-1-yl. |

14. The compound of claim 6 of the Formula III:

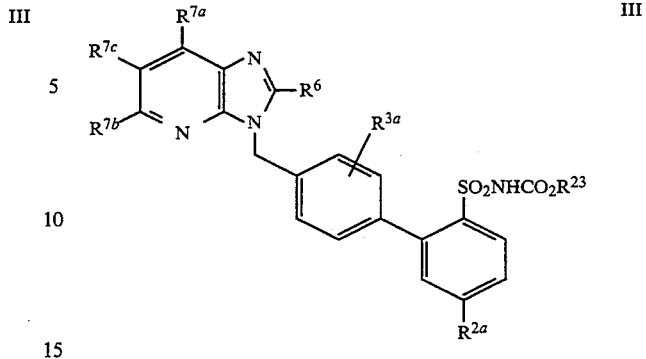

wherein $R^{7a}$ is H, or Me; and $R^{7b}$ is H, Me, or $CO_2H$; and $R^6$ is Et, Pr, or Bu; and $R^{2a}$ is H, Et, Pr, n-Bu, or i-Bu; and $R^{3a}$ is H or 3-F; and $R^{7c}$ and $R^{23}$ are as defined below in Table D:

TABLE D

| $R^{7c}$ | $R^{23}$ |
|---|---|
| $-NHSO_2Pr$ | -n-Bu |
| $-NHSO_2Pr$ | $-CH_2CH(CH_3)_2$ |
| $-NHSO_2Pr$ | $-CH_2(C_6H_5)$ |
| $-NHSO_2Bu$ | -n-Bu |
| $-NHSO_2Bu$ | $-CH_2CH(CH_3)_2$ |
| $-NHSO_2Bu$ | $-CH_2(C_6H_5)$ |
| $-NHSO_2$-morpholine-4-yl | -n-Bu |
| $-NHSO_2$-morpholine-4-yl | $-CH_2CH(CH_3)_2$ |
| $-NHSO_2$-morpholine-4-yl | $-CH_2(C_6H_5)$ |
| $-NHSO_2NHEt$ | -n-Bu |
| $-NHSO_2NHEt$ | $-CH_2CH(CH_3)_2$ |
| $-NHSO_2NHEt$ | $-CH_2(C_6H_5)$. |

15. The compound of claim 6 of the Formula III:

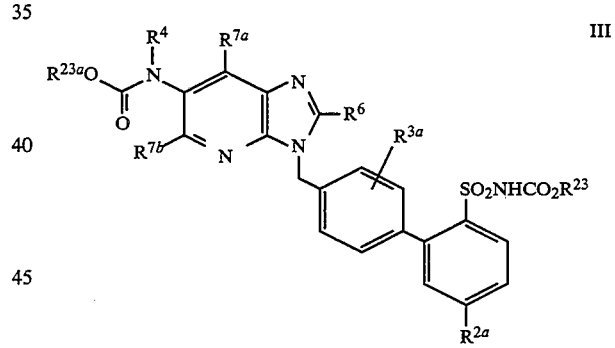

wherein $R^{7a}$ is H, or Me; and $R^{7b}$ is H, Me, or $CO_2H$; and $R^6$ is Et, Pr, or Bu; $R^{2a}$ is H, Et, Pr, n-Bu or i-Bu; and $R^{3a}$ is H or 3-F; and $R^4$ is H, or $CH_3$ and $R^{23}$ and $R^{23a}$ are as defined below in the Table E:

TABLE E

| $R^{23}$ | $R^{23a}$ |
|---|---|
| -n-Bu | Et |
| $-CH_2CH(CH_3)_2$ | Et |
| $-CH_2(C_6H_5)$ | Et |
| -n-Bu | Pr |
| $-CH_2CH(CH_3)_2$ | Pr |
| $-CH_2(C_6H_5)$ | Pr |
| -n-Bu | Ph |
| $-CH_2CH(CH_3)_2$ | Ph |
| $-CH_2(C_6H_5)$ | Ph |
| -n-Bu | -i-Pr |
| $-CH_2CH(CH_3)_2$ | -i-Pr |
| $-CH_2(C_6H_5)$ | -i-Pr |
| $-CH_2CH_2OCH_3$ | Ph |
| $-CH_2CH_2OCH_3$ | -i-Pr. |

* * * * *